US008283346B2

(12) United States Patent
Ganguly et al.

(10) Patent No.: US 8,283,346 B2
(45) Date of Patent: Oct. 9, 2012

(54) HUMAN IMMUNODEFICIENCY VIRUS PROTEASE INHIBITORS

(75) Inventors: A. K. Ganguly, Upper Montclair, NJ (US); Dipshikha Biswas, Woodbridge, NJ (US); Sesha Sridevi Alluri, Piscataway, NJ (US); Danielle Caroccia, Hasbrouck Heights, NJ (US); Chih-Hung Wang, New York, NY (US); Eun Hee Kang, Fort Lee, NJ (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 268 days.

(21) Appl. No.: 12/615,903

(22) Filed: Nov. 10, 2009

(65) Prior Publication Data
US 2011/0112068 A1    May 12, 2011

(51) Int. Cl.
*A61K 31/553* (2006.01)
*A61K 31/554* (2006.01)
*C07D 267/04* (2006.01)
*C07D 267/14* (2006.01)
(52) U.S. Cl. .................. 514/211.09; 514/552
(58) Field of Classification Search ............. 514/211.09; 540/552
See application file for complete search history.

(56) References Cited

OTHER PUBLICATIONS

Hornback JM. Organic Chemistry. 2006, Thomson BrooksCole, pp. 116-118 provided.*
Reddy et al., "Design and Synthesis of HIV-1 Protease Inhibitors Incorporating Oxazolidinones as P2/P2' Ligands in Pseudosymmetric Dipeptide Isosteres", J. Med. Chem. 2007, 50 pp. 4316-4328.
Ghosh et al., "Structure-Based Design: Synthesis and Biological Evaluation of a Series of Novel Cycloamide-Derived HIV-1 Protease Inhibitors", J. Med. Chem. 2005, 48, pp. 3576-3585.
Ali et al., "Discovery of HIV-1 Protease Inhibitors with Picomolar Affinities Incorporating N-Aryl-oxazolidinone-5-carboxamides as Novel P2 Ligands", J. Med. Chem. 2006 49, pp. 7342-7356.
Langer, "New Methods of Drug Delivery", Science, vol. 249, Sep. 28, 1990, pp. 1527-1533.
Rigaudy et al., "Nomenclature of Organic Chemistry, Sections A, B, C, D, E, F and H, 1979 Edition", International Union of Pure and Applied Chemistry Organic Chemistry Division Commission on Nomenclature of Organic Chemistry, pp. 473-490.
Panico et al., "A Guide to IUPAC Nomenclature of Organic Compounds, Recommendations 1993", International Union of Pure and Applied Chemistry Organic Chemistry Division, Commission on Nomenclature of Organic Chemistry (III.1), pp. 149-151.
Sawhney et al., "Bioerodible Hydrogels Based on Photopolymerized Poly(ethylene glycol)-co-poly(α-hydroxy acid) Diacrylate Macromers", Macromolecules, 1993 26, 581-587.
Lyle, "Ribonucleic Acid Viruses: Antivirals for Human Immunodeficiency Virus", Comprehensive Medical Chemistry II, vol. 7, pp. 329-371, 2007.

* cited by examiner

*Primary Examiner* — Paul Zarek
(74) *Attorney, Agent, or Firm* — Beverly W. Lubit; Greenberg Traurig, LLP

(57) ABSTRACT

The described invention relates to novel human immunodeficiency virus protease inhibitors, pharmaceutical compositions containing at least one such inhibitor, methods of preparing such inhibitors, and methods of utilizing such inhibitors to treat HIV and HIV-related disorders.

68 Claims, 1 Drawing Sheet

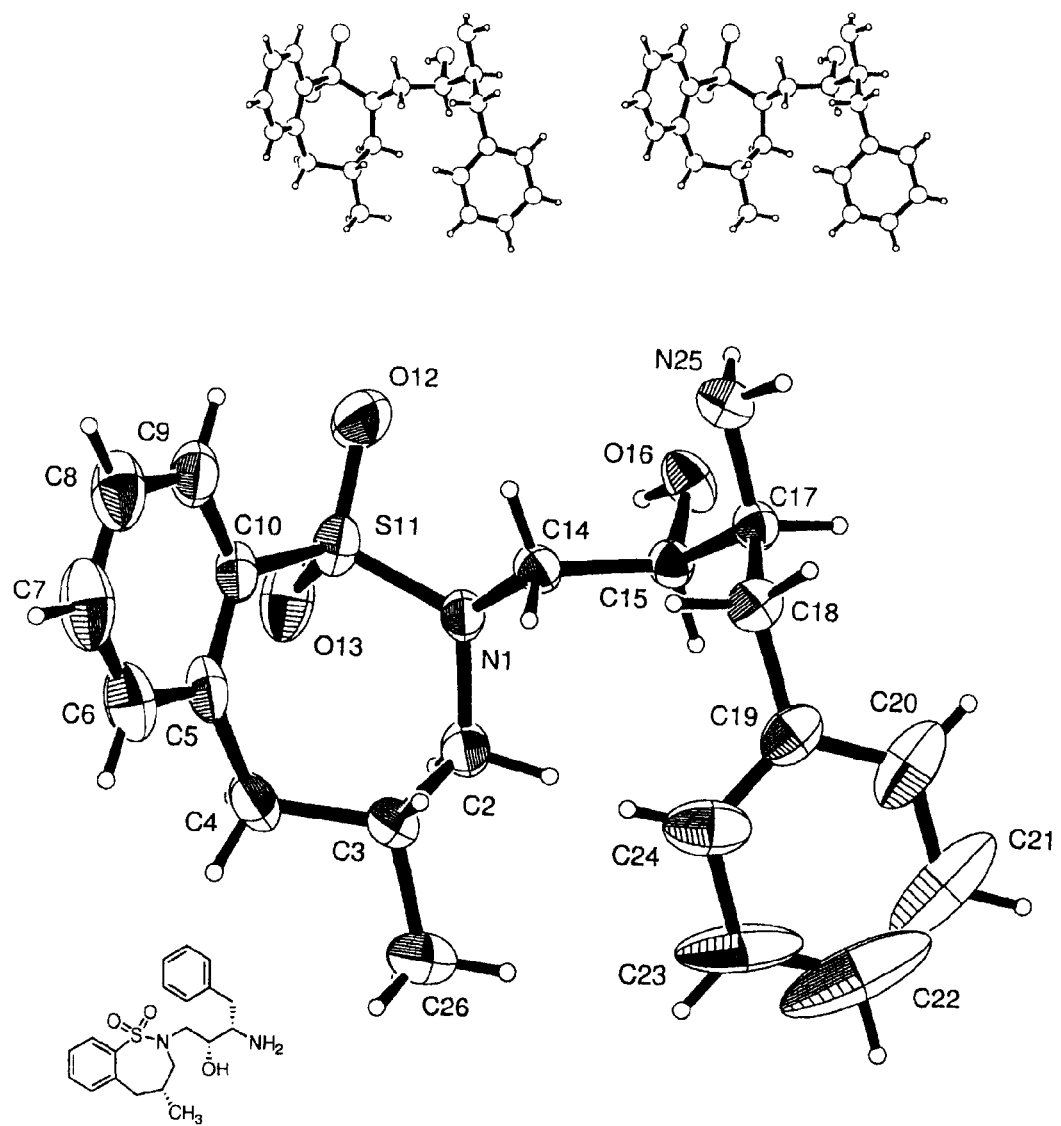

HUMAN IMMUNODEFICIENCY VIRUS PROTEASE INHIBITORS

FIELD OF INVENTION

The described invention relates to novel human immunodeficiency virus protease inhibitors, pharmaceutical compositions containing at least one such inhibitor, methods of preparing such inhibitors, and methods of utilizing such inhibitors to treat HIV and HIV-related disorders.

BACKGROUND OF THE INVENTION

Human immunodeficiency virus ("HIV") is a member of the genus Lentivirinae, which is part of the family of Retroviridae. Lentiviruses are transmitted as single-stranded, positive-sense, enveloped RNA viruses. Upon entry of the target cell, the viral RNA genome is converted to double-stranded DNA by a virally encoded reverse transcriptase. This viral DNA then is integrated into the cellular DNA by a virally encoded integrase, along with host cellular co-factors, so that the viral genome can be transcribed. After the virus has infected the cell, two pathways are possible: (1) the virus becomes latent and the infected cell continues to function, or (2) the virus becomes active and replicates.

There are two strains of HIV known to exist: HIV-1 and HIV-2.

In HIV-1, the HIV-1 protease is synthesized as part of a 165 kDa polyprotein (Gag-Pol). Gag-Pol comprises the matrix, capsid, P2, nucleocapsid, transframe, protease (PR), reverse transcriptase, and integrase domains. The protease mediates its own release and the processing of the viral polyproteins, Gag, and Gag-Pol, into the necessary structural and functional proteins. This spatio-temporally regulated process is crucial for the maturation and propagation of HIV.

The HIV-1 protease is composed of 99 amino acids and is a member of the family of aspartic acid proteases. Unlike the cellular aspartic proteases that are active as monomers, catalytic activity of retroviral proteases, including HIV-1 proteases, requires dimer formation. All aspartic proteases, including retroviral proteases, share the triplet DTG (Asp25, Thr26 and Gly27) critical for the active site geometry and catalytic function. These residues interact closely in the active, dimeric structure of HIV-1 proteases. The active site is formed along the dimer interface, and each subunit contributes one of the two catalytic aspartic acid residues. These residues are expected to be in opposite states of protonation for activity, and the water molecule involved in the hydrolysis of the peptide bond has been proposed to be hydrogen bonded to the aspartyl residues. The hydrolysis of the peptide bond mediated by the protease involves general base/general acid catalysis. Additionally, studies of the steps in the maturation of the Gag-Pol precursor and the mechanism of the autocatalytic maturation of the protease have revealed that upon its intramolecular maturation at its N-terminus, the protease forms a stable dimer concomitant with the formation of the terminal β-sheet structure and a very low equilibrium dimer dissociation constant ($K_d$<10 nM).

HIV protease inhibitors ("HIV-PIs"), which are designed to inhibit the HIV aspartyl protease, are key components of highly active antiretroviral therapy ("HAART"), but they have been associated with adverse side effects, including partial lipodystrophy and metabolic syndrome. The emergence of drug-resistant HIV proteases has coincided with the widespread use of HIV-PIs. In these drug-resistant HIV proteases, mutations have been found in at least 49 of the 99 amino acids of the coding sequence. The loss of responsiveness to HIV-PI treatment has been directly correlated to substitutions at 18 or more positions. Hence, there is a need for new HIV-PIs.

BRIEF DESCRIPTION OF THE DRAWINGS

FIG. 1 shows an ORTEP diagram (40% probability ellipsoids) showing the crystallographic atom numbering scheme and solid-state conformation; small circles represent hydrogen atoms.

SUMMARY

According to one aspect, the described invention provides a compound of formula

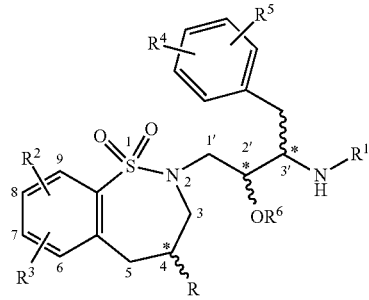

wherein R, $R^1$, $R^2$, $R^3$, $R^4$, $R^5$ and $R^6$ each independently are:

R=H, alkyl, aryl, aryl alkyl, heterocycles, and substitutions thereof,

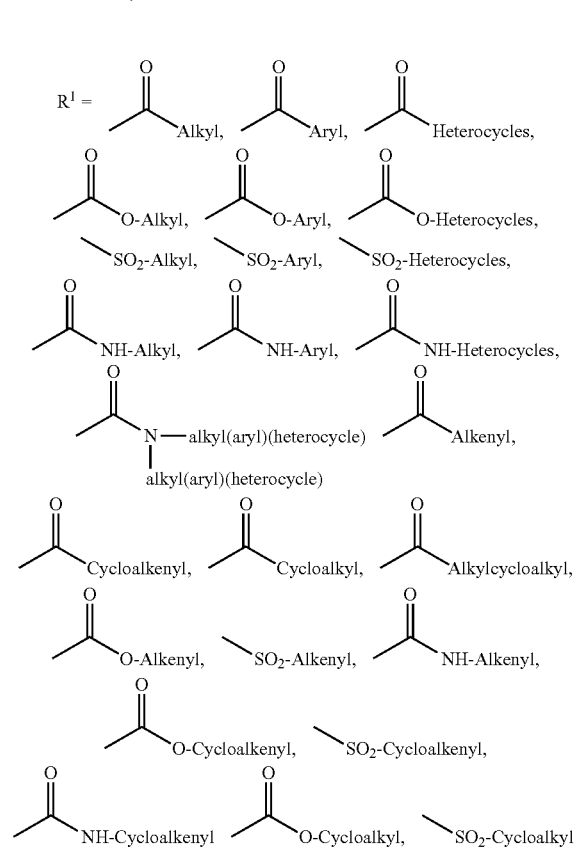

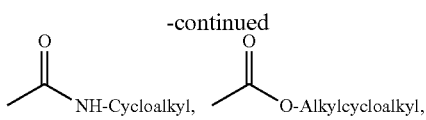

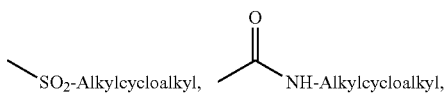

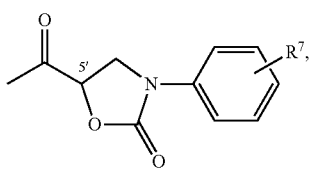

where $R^7$=H, an electron donating group, or an electron withdrawing group at some or all the positions on the aromatic ring;

$R^2$, $R^3$, $R^4$, and $R^5$ are each independently H, an electron donating group, or an electron withdrawing group at some or all the positions on the aromatic ring;

$R^6$ is H, a phosphate or amino acid ester(s) or salt(s) thereof;

and where "*" represents a chiral center. According to one embodiment, the C4 carbon is of a S absolute configuration. According to another embodiment, the C2' carbon is of a R absolute configuration. According to another embodiment, the C3' carbon is of a S absolute configuration. According to another embodiment, the compound is

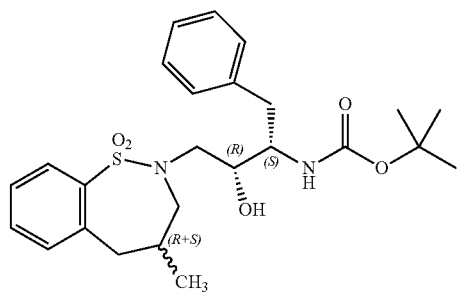

wherein the compound has stereochemistry of S(C3')-R(C2')-R+S(C4). According to another embodiment, the compound is

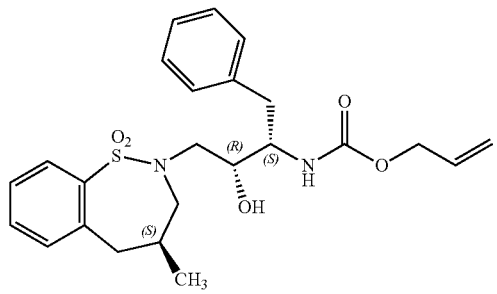

wherein the C3' carbon is of a S absolute configuration, the C2' carbon is of a R absolute configuration, and the C4 carbon is of a S absolute configuration. According to another embodiment, the compound is

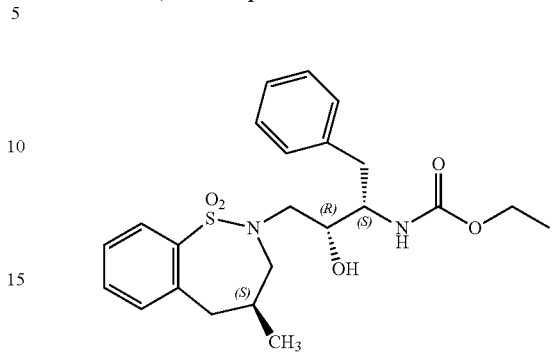

wherein the C3' carbon is of a S absolute configuration, the C2' carbon is of a R absolute configuration, and the C4 carbon is of a S absolute configuration. According to another embodiment, the compound is

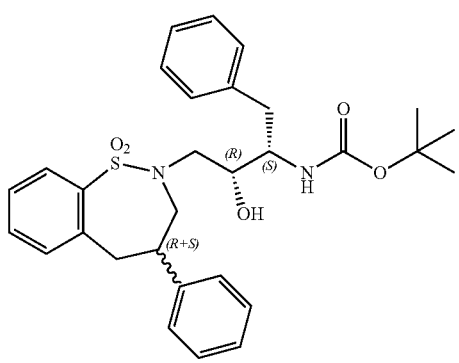

wherein the C3' carbon is of a S absolute configuration, the C2' carbon is of a R absolute configuration, and the C4 carbon is of a R absolute configuration or S absolute configuration. According to another embodiment, the compound is

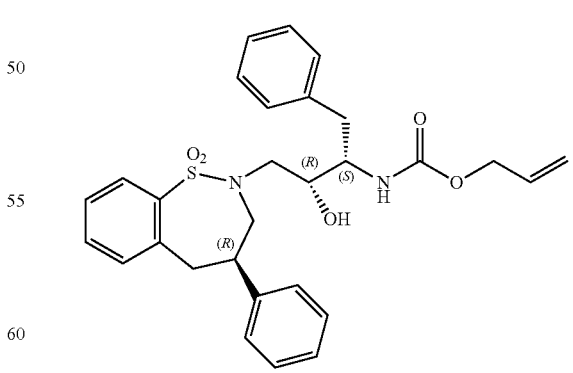

wherein the C3' carbon is of a S absolute configuration, the C2' carbon is of a R absolute configuration, and the C4 carbon is of a R absolute configuration. According to another embodiment, the compound is

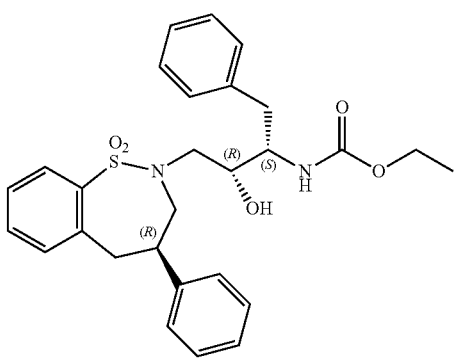

wherein the C3' carbon is of a S absolute configuration, the C2' carbon is of a R absolute configuration, and the C4 carbon is of a R absolute configuration. According to another embodiment, the compound is

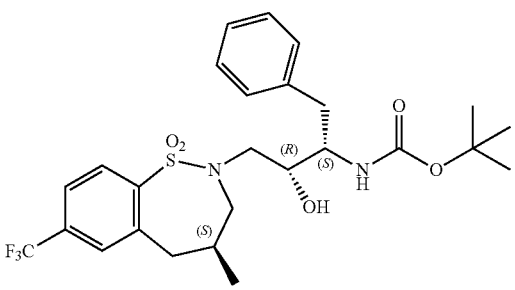

wherein the C3' carbon is of a S absolute configuration, the C2' carbon is of a R absolute configuration, and the C4 carbon is of a S absolute configuration. According to another embodiment, the compound is wherein the C3' carbon is of a S absolute configuration, the C2' carbon is of a R absolute configuration, and the C4 carbon is of a S absolute configuration. According to another embodiment, the compound is wherein the C3' carbon is of a S absolute configuration, the C2' carbon is of a R absolute configuration, and the C4 carbon is of a S absolute configuration. According to another embodiment, the compound is wherein the C3' carbon is of a S absolute configuration, the C2' carbon is of a R absolute configuration, and the C4 carbon is of a S absolute configuration. According to another embodiment, the compound is wherein the C3' carbon is of a S absolute configuration, the C2' carbon is of a R absolute configuration, and the C4 carbon is of a S absolute configuration. According to another embodiment, the compound is

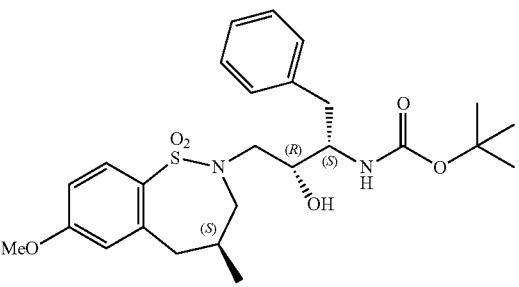

wherein the C3' carbon is of a S absolute configuration, the C2' carbon is of a R absolute configuration, and the C4 carbon is of a S absolute configuration. According to another embodiment, the compound is

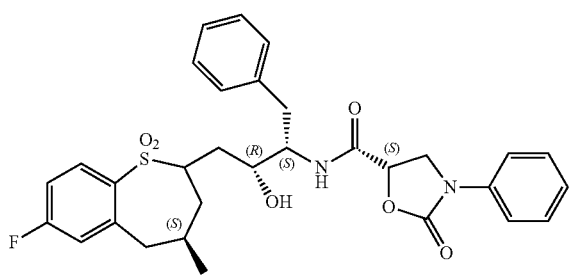

wherein the C3' carbon is of a S absolute configuration, the C2' carbon is of a R absolute configuration, the C4 carbon is of a S absolute configuration, and C5' carbon is of a S absolute configuration.

According to another aspect, the described invention provides a composition for inhibiting HIV protease, the composition comprising a compound of formula

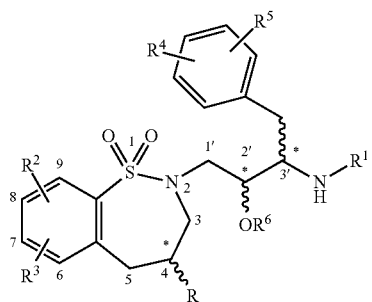

wherein R, $R^1$, $R^2$, $R^3$, $R^4$, $R^5$ and $R^6$ each independently are:

R=H, alkyl, aryl, aryl alkyl, heterocycles, and substitutions thereof,

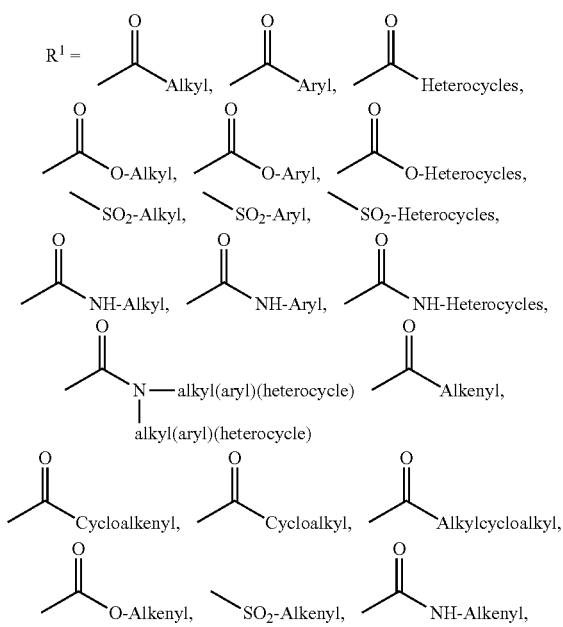

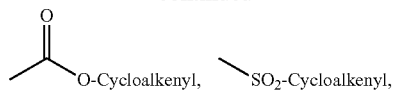

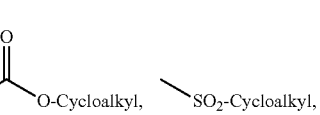

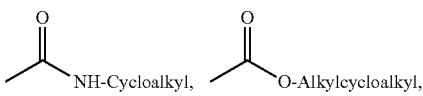

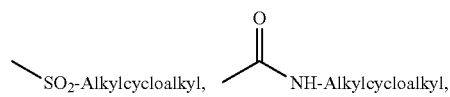

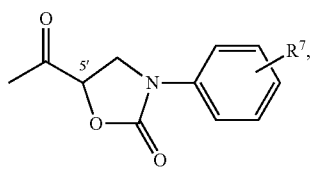

where $R^7$=H, an electron donating group, or an electron withdrawing group at some or all the positions on the aromatic ring;

$R^2$, $R^3$, $R^4$, and $R^5$ are each independently H, an electron donating group, or an electron withdrawing group at some or all the positions on the aromatic ring;

$R^6$ is H, a phosphate or amino acid ester(s) or salt(s) thereof;

wherein "*" represents a chiral center, and a pharmaceutically acceptable carrier. According to one embodiment, the C4 carbon is of a S absolute configuration. According to another embodiment, the C2' carbon is of a R absolute configuration. According to another embodiment, the C3' carbon is of a S absolute configuration. According to another embodiment, the compound is

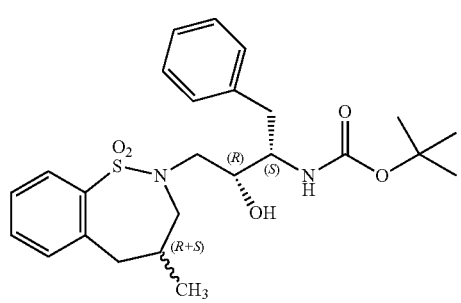

wherein the C3' carbon is of a S absolute configuration, the C2' carbon is of a R absolute configuration, and the C4 carbon is of a R absolute configuration or a S absolute configuration. According to another embodiment, the compound is

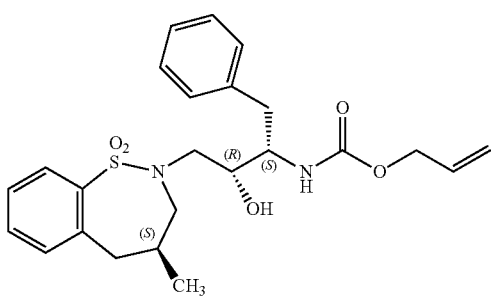

wherein the C3' carbon is of a S absolute configuration, the C2' carbon is of a R absolute configuration, and the C4 carbon is of a S absolute configuration. According to another embodiment, the compound is

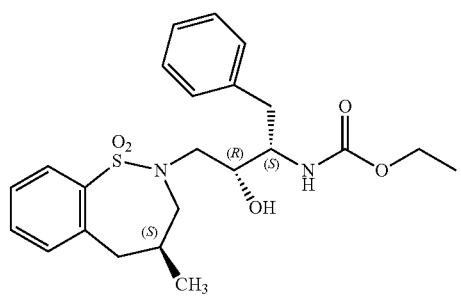

wherein the C3' carbon is of a S absolute configuration, the C2' carbon is of a R absolute configuration, and the C4 carbon is of a S absolute configuration. According to another embodiment, the compound is

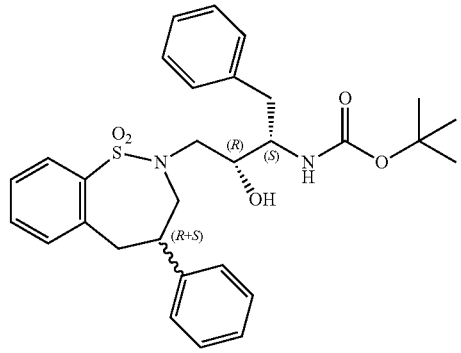

wherein the C3' carbon is of a S absolute configuration, the C2' carbon is of a R absolute configuration, and the C4 carbon is of a R absolute configuration or a S absolute configuration. According to another embodiment, the compound is

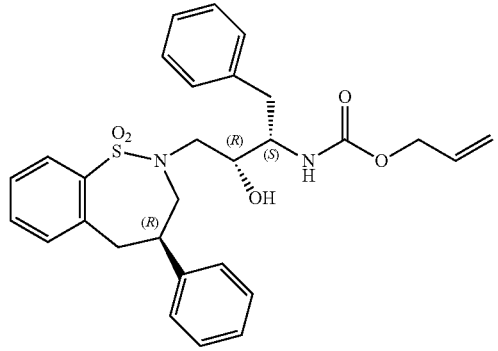

wherein the C3' carbon is of a S absolute configuration, the C2' carbon is of a R absolute configuration, and the C4 carbon is of a R absolute configuration. According to another embodiment, the compound is

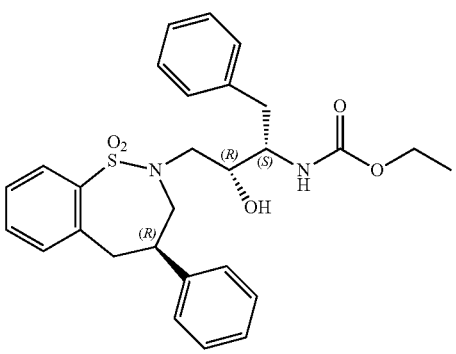

wherein the C3' carbon is of a S absolute configuration, the C2' carbon is of a R absolute configuration, and the C4 carbon is of a R absolute configuration. According to another embodiment, the compound is

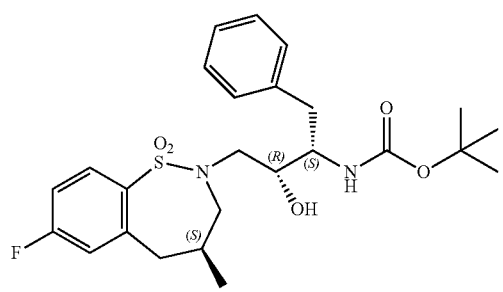

wherein the C3' carbon is of a S absolute configuration, the C2' carbon is of a R absolute configuration, and the C4 carbon is of a S absolute configuration. According to another embodiment, the compound is wherein the C3' carbon is of a S absolute configuration, the C2' carbon is of a R absolute configuration, and the C4 carbon is of a S absolute configuration. According to another embodiment, the compound is

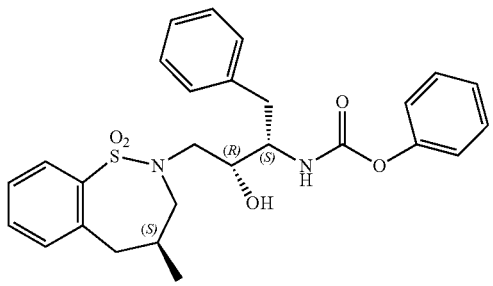

wherein the C3' carbon is of a S absolute configuration, the C2' carbon is of a R absolute configuration, and the C4 carbon is of a S absolute configuration. According to another embodiment, the compound is

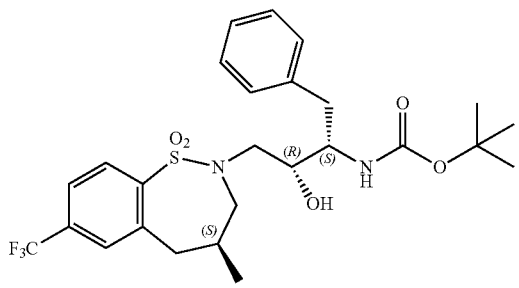

wherein the C3' carbon is of a S absolute configuration, the C2' carbon is of a R absolute configuration, and the C4 carbon is of a S absolute configuration. According to another embodiment, the compound is

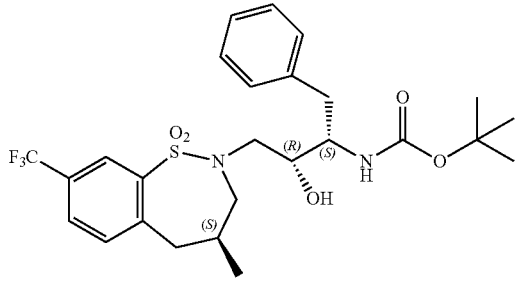

wherein the C3' carbon is of a S absolute configuration, the C2' carbon is of a R absolute configuration, and the C4 carbon is of a S absolute configuration. According to another embodiment, the compound is

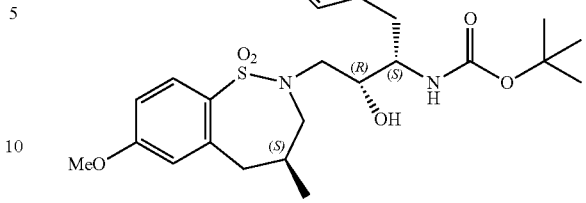

wherein the C3' carbon is of a S absolute configuration, the C2' carbon is of a R absolute configuration, and the C4 carbon is of a S absolute configuration. According to another embodiment, the compound is

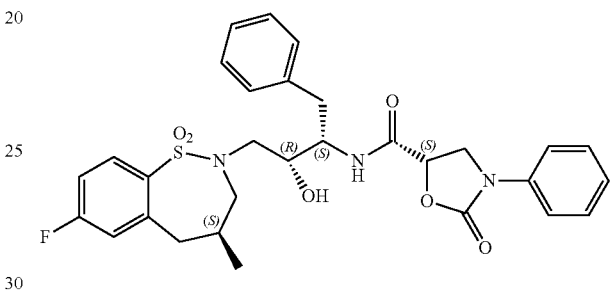

wherein the C3' carbon is of a S absolute configuration, the C2' carbon is of a R absolute configuration, the C4 carbon is of a S absolute configuration, and the C5' carbon is of a S absolute configuration.

According to another aspect, the described invention provides a method for inhibiting a HIV protease in a subject, the method comprising steps:

(a) administering to a subject in need thereof a pharmaceutical composition comprising (i) a therapeutically effective amount of a compound of formula:

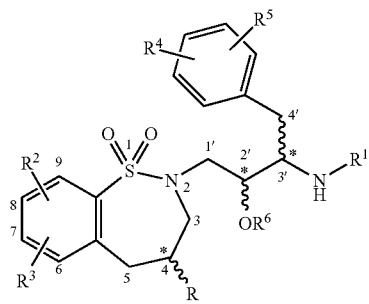

wherein R, $R^1$, $R^2$, $R^3$, $R^4$, $R^5$ and $R^6$ each independently are:

R=H, alkyl, aryl, aryl alkyl, heterocycles, and substitutions thereof,

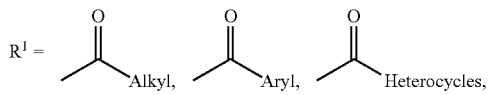

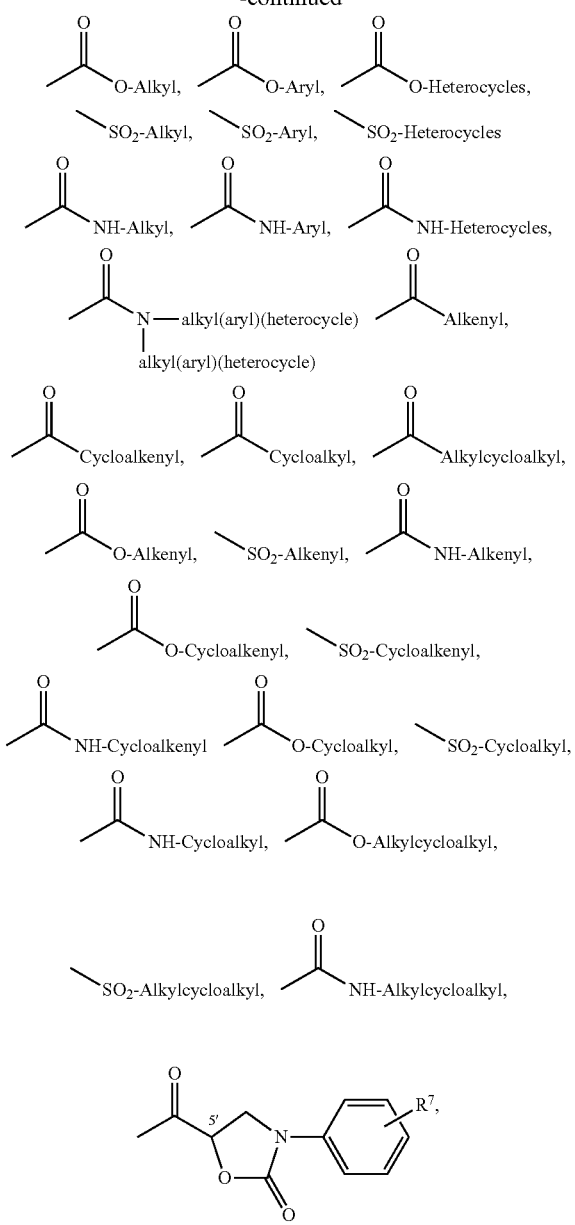

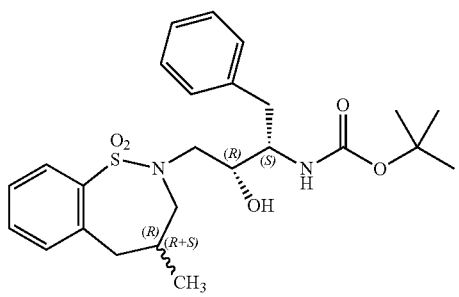

wherein the C3' carbon is of a S absolute configuration, the C2' carbon is of a R absolute configuration, and the C4 carbon is of a R absolute configuration or a S absolute configuration. According to another embodiment, the compound is

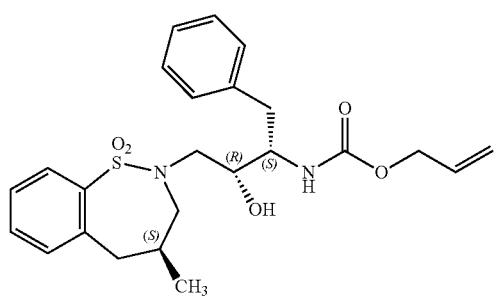

wherein the C3' carbon is of a S absolute configuration, the C2' carbon is of a R absolute configuration, and the C4 carbon is of a S absolute configuration. According to another embodiment, the compound is

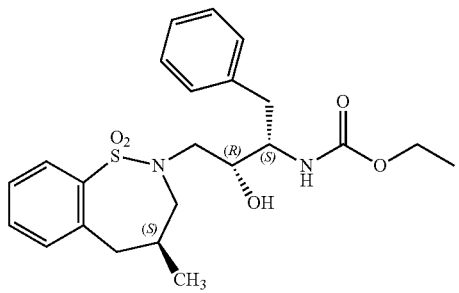

wherein the C3' carbon is of a S absolute configuration, the C2' carbon is of a R absolute configuration, and the C4 carbon is of a S absolute configuration. According to another embodiment, the compound is

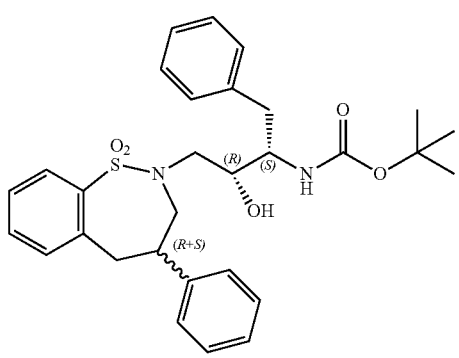

where $R^7$=H, an electron donating group, or art electron withdrawing group at some or all the positions on the aromatic ring;

$R^2$, $R^3$, $R^4$, and $R^5$ are each independently H, an electron donating group, or an electron withdrawing group at some or all the positions on the aromatic ring;

$R^6$ is H, a phosphate or amino acid ester(s) or salt(s) thereof;

wherein "*" represents a chiral center, and (ii) a pharmaceutically acceptable carrier;

thereby reducing the enzymatic activity of a HIV protease. According to one embodiment, the C4 carbon is of a S absolute configuration. According to another embodiment, the C2' carbon is of a R absolute configuration. According to another embodiment, the C3' carbon is of a S absolute configuration. According to another embodiment, the compound is wherein the C3' carbon is of a S absolute configuration, the C2' carbon is of a R absolute configuration, and the C4 carbon is of a R absolute configuration or S absolute configuration. According to another embodiment, the compound is

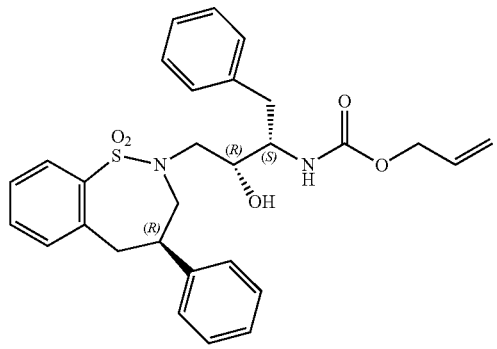

wherein the C3' carbon is of a S absolute configuration, the C2' carbon is of a R absolute configuration, and the C4 carbon is of a R absolute configuration. According to another embodiment, the compound is

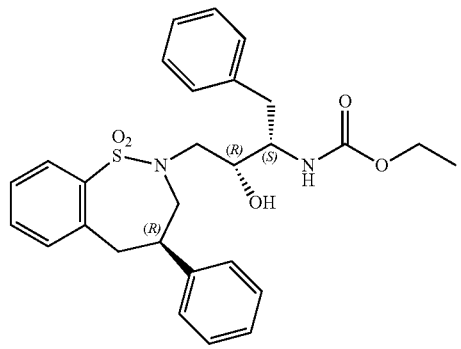

wherein the C3' carbon is of a S absolute configuration, the C2' carbon is of a R absolute configuration, and the C4 carbon is of a R absolute configuration. According to another embodiment, the compound is

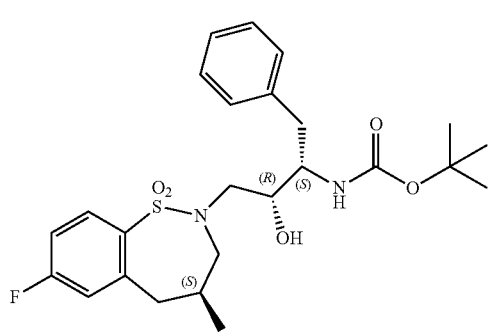

wherein the C3' carbon is of a S absolute configuration, the C2' carbon is of a R absolute configuration, and the C4 carbon is of a S absolute configuration. According to another embodiment, the compound is

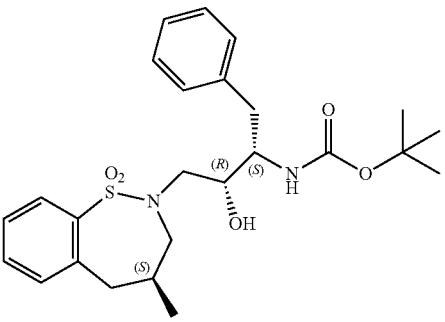

wherein the C3' carbon is of a S absolute configuration, the C2' carbon is of a R absolute configuration, and the C4 carbon is of a S absolute configuration. According to another embodiment, the compound is

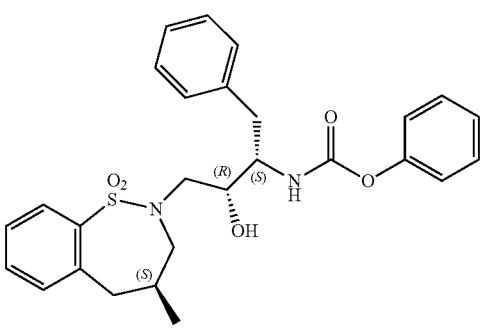

wherein the C3' carbon is of a S absolute configuration, the C2' carbon is of a R absolute configuration, and the C4 carbon is of a S absolute configuration. According to another embodiment, the compound is

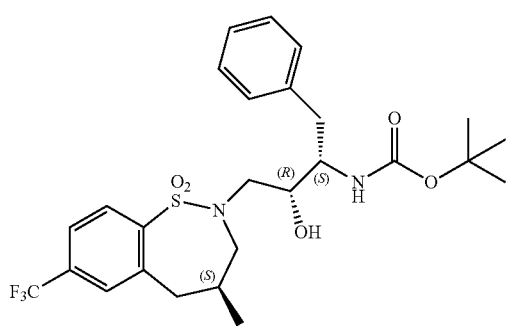

wherein the C3' carbon is of a S absolute configuration, the C2' carbon is of a R absolute configuration, and the C4 carbon is of a S absolute configuration. According to another embodiment, the compound is

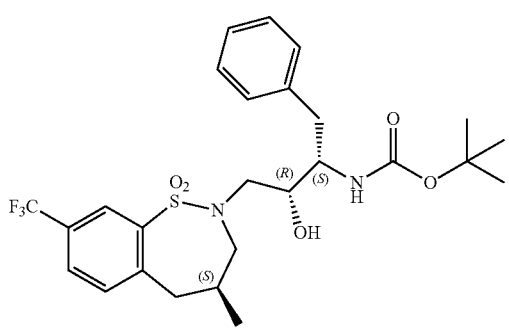

wherein the C3' carbon is of a S absolute configuration, the C2' carbon is of a R absolute configuration, and the C4 carbon is of a S absolute configuration. According to another embodiment, the compound is

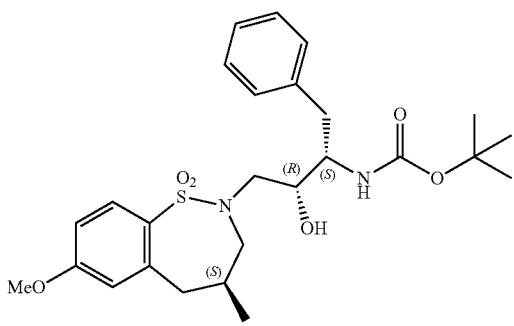

wherein the C3' carbon is of a S absolute configuration, the C2' carbon is of a R absolute configuration, and the C4 carbon is of a S absolute configuration. According to another embodiment, the compound is

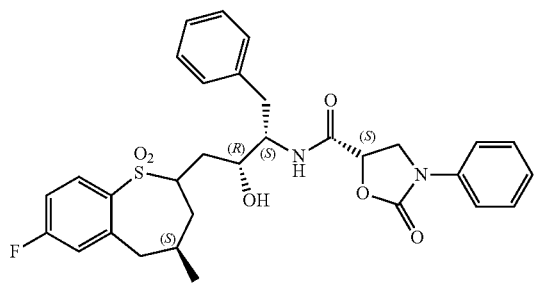

wherein the C3' carbon is of a S absolute configuration, the C2' carbon is of a R absolute configuration, the C4 carbon is of a S absolute configuration, and the C5' carbon is of a S absolute configuration. According to another embodiment, the HIV protease is HIV-1 protease. According to another embodiment, the HIV protease is HIV-2 protease. According to another embodiment, the therapeutically effective amount is from about 0.000001 mg/kg body weight to about 10 g/kg body weight. According to another embodiment, the composition further comprises a therapeutically effective amount of an additional therapeutic agent. According to another embodiment, the additional therapeutic agent is selected from the group consisting of an antibiotic agent, an antifungal agent, an antiviral agent, an antiprotozoal agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, or a hormone. According to another embodiment, the electron withdrawing group is a halogen. According to another embodiment, the electron withdrawing group is nitrile. According to another embodiment, the electron withdrawing group is a carboxylic acid. According to another embodiment, the electron withdrawing group is a carbonyl, alkyl sulphone, aryl sulphone, sulphonamides, amides and N-substituted amides. According to another embodiment, the electron withdrawing group is an aldehyde. According to another embodiment, the electron withdrawing group is an acetaldehyde. According to another embodiment, the electron withdrawing group is a nitro group. According to another embodiment, the electron withdrawing group is selected from the group consisting of a trifluoromethyl, a difluoromethyl, a nitrile, a nitro, a sulphone, a sulphonamide, an amide and an N-substituted amide. According to another embodiment, the electron donating group is an alkyl group. According to another embodiment, the electron donating group is an alcohol group. According to another embodiment, the electron donating group is selected from the group consisting of an alkoxy, a trifluoromethoxy, and a difluoromethoxy. According to another embodiment, the electron donating group is selected from the group consisting of an amino group, an amide, a substituted amide, an urea, a substituted urea, a sulphonamide and a substituted sulphonamide.

DETAILED DESCRIPTION

The described invention relates to novel human immunodeficiency virus protease inhibitors, pharmaceutical compositions containing at least one such inhibitor, methods of preparing such inhibitors, and methods of utilizing such inhibitors to treat HIV and HIV-related disorders.

HIV Protease Inhibitor Compositions

According to one aspect, the present invention provides compounds of formula I as inhibitors of HIV protease:

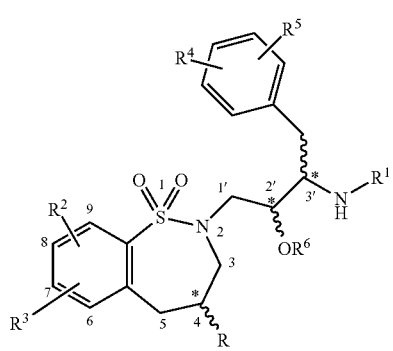

wherein R, $R^1$, $R^2$, $R^3$, $R^4$, $R^5$, and $R^6$ each independently are:

R=H, alkyl, aryl, arylalkyl, alkenyl, cycloalkyl, cycloalkenyl, alkylcycloalkyl 1, heterocycles, and substitutions thereof, $R^1$ =

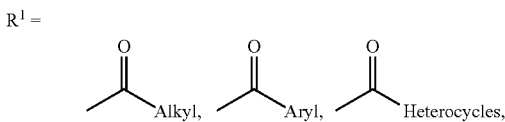

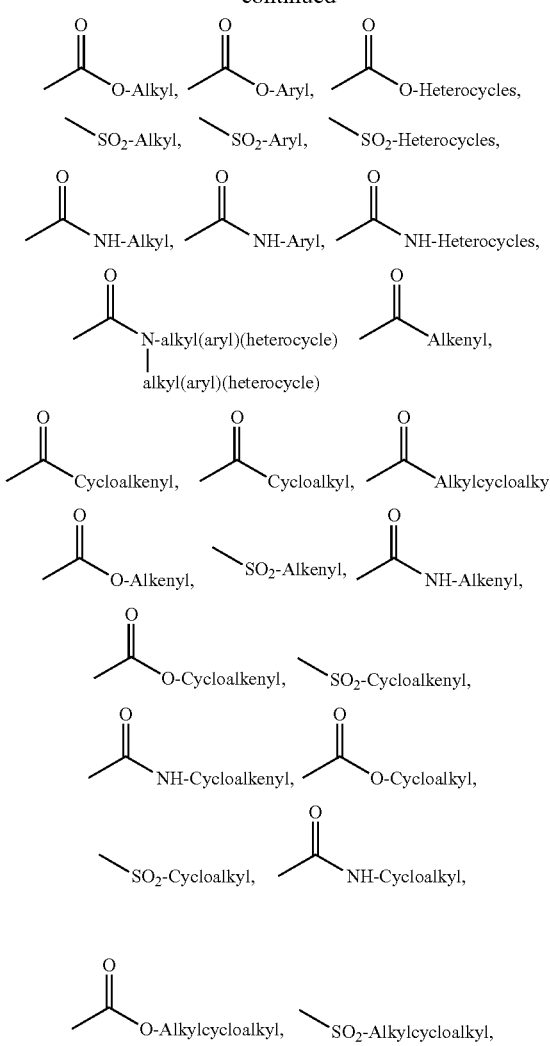

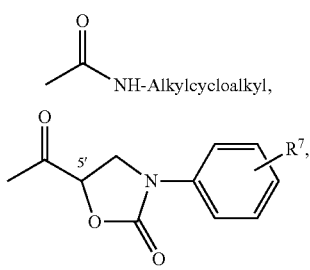

where $R^7$=H, an electron donating group, or an electron withdrawing group at some or all the positions on the aromatic ring;

$R^2$, $R^3$, $R^4$, and $R^5$ are each independently H, an electron donating group, or an electron withdrawing group at some or all the positions on the aromatic ring;

$R^6$ is H, a phosphate or amino acid ester(s) or salt(s) thereof;

and where "*" represents a chiral center.

According to some such embodiments, the compound has 3 chiral centers.

According to some such embodiments, when $R^1$=

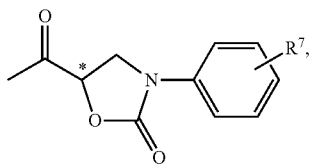

the compound has 4 chiral centers.

According to some such embodiments, $R^1$=

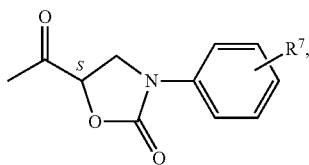

where C5' has S absolute configuration.

According to some such embodiments, $R^1$=

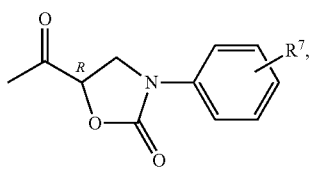

where C5' has R absolute configuration.

The stereochemistry marked by "*" may represent all possible combinations in terms of relative and absolute chemistry, i.e., diastereomers including racemic or pure enantiomers. It should be noted that the stereochemistry of all the compounds with C4 methyl substituents are rigidly established using X-ray data. Further, the stereochemistry of compounds with C4 phenyl substituents are based on their relative polarities and biological activity. When comparing the two diastereoisomers, the more active compounds in the C4 methyl and C4 phenyl series are consistently more polar than the corresponding diastereoisomer.

"Electronegativity" means a tendency to become negatively charged. The attractive force exerted by the nuclei of atoms that have orbital vacancies in their outer shells is a fundamental factor in the formation of chemical compounds. All atoms (except those of Helium) that have fewer than 8 electrons in their highest principal quantum level have low energy orbital vacancies capable of accommodating electrons from outside the atom. The most highly electronegative elements are the halogens, sulfur and oxygen.

The term "electron withdrawing group" as used herein refers to a group that draws electrons away from a reaction center. For example, electron withdrawing groups remove electron density from the π system of a benzene ring making it less nucleophilic. Examples of electron withdrawing groups include, but are not limited to, halogens (F, Cl, Br, or I); nitriles (CN); carboxylic acids (COOH); carbonyls (CO); carboxyl groups, -aldehydes (—CHO), acetaldehydes

COOH$_3$, nitro groups (NO$_2$), tetrafluoromethyl, amides and sulphonamides.

The term "electron donating group" refers to a group that releases electrons into a reaction center. Electron donating groups add electron density to the π system of a benzene ring making it more nucleophilic. Examples of electron donating groups include, but are not limited to, alkyl groups, alcohol groups alkoxy, and amino groups, phenolic group and its derivatives.

Substituents

The term "Aliphatic" as used herein, denotes a straight- or branched-chain arrangement of constituent carbon atoms, including, but not limited to paraffins (alkanes), which are saturated, olefins (alkenes or alkadienes), which are unsaturated, and acetylenes (alkynes), which contain a triple bond. In complex structures, the chains may be branched or crosslinked.

The term "lower" as used herein refers to a group having between one and six carbons.

As used herein, the term "alkyl" refers to a straight or branched chain hydrocarbon having from 1 to 25 carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may contain one or more O, S, S(O), or S(O)$_2$ atoms. Examples of "alkyl" as used herein include, but are not limited to, methyl, ethyl, propyl, decyl, undecyl, octadecyl, nonadecyl, eicosyl, heneicosyl, decosyl, tricosyl, tetracosyl, and pentacosyl, n-butyl, t-butyl, n-pentyl, isobutyl, and isopropyl, and the like.

The term "alkylene" as used herein refers to a straight or branched chain divalent hydrocarbon radical having from one to 25 carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may contain one or more O, S, S(O), or S(O)$_2$ atoms. Examples of "alkylene" as used herein include, but are not limited to, methylene, ethylene, and the like.

The term "Alkenyl," as used herein, denotes a monovalent, straight (unbranched) or branched hydrocarbon chain having one or more double bonds therein where the double bond can be unconjugated or conjugated to another unsaturated group (e.g., a polyunsaturated alkenyl) and can be unsubstituted or substituted, with multiple degrees of substitution being allowed. It may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may contain one or more O, S, S(O), or S(O)$_2$ atoms. For example, and without limitation, the alkenyl can be vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, decenyl, undecenyl, dodecenyl, heptadecenyl, octadecenyl, nonadecenyl, eicosenyl, heneicosenyl, docosenyl, tricosenyl, tetracisenyl, pentacosenyl, phytyl, the branched chain isomers thereof, and polyunsaturated alkenes including octadec-9,12,-dienyl, octadec-9,12,15-trienyl, and eicos-5,8,11,14-tetraenyl.

As used herein, the term "alkenylene" refers to a straight or branched chain divalent hydrocarbon radical having from 2 to 25 carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may contain one or more O, S, S(O), or S(O)$_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from 2 to 25 carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may contain one or more O, S, S(O), or S(O)$_2$ atoms.

As used herein, the term "alkynylene" refers to a straight or branched chain divalent hydrocarbon radical having from 2 to 25 carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may contain one or more O, S, S(O), or S(O)$_2$ atoms. Examples of "alkynylene" as used herein include, but are not limited to, ethyne-1,2-diyl, propyne-1,3-diyl, and the like.

The term "aryl" as used herein refers to a benzene ring or to an optionally substituted benzene ring system fused to one or more optionally substituted benzene rings, with multiple degrees of substitution being allowed. Substituents include, but are not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-napthyl, 1-naphthyl, 1-anthracenyl, and the like.

It should be understood that wherever the terms "alkyl" or "aryl" or either of their prefix roots appear in a name of a substituent, they are to be interpreted as including those limitations given above for alkyl and aryl. Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

The terms "carbamates" or "urethanes" as used herein refer to a group of organic compounds sharing a common functional group having the general structure —NH(CO)O—.

As used herein, "cycloalkyl" (used interchangeably with "aliphatic cyclic" herein) refers to a alicyclic hydrocarbon group optionally possessing one or more degrees of unsaturation, having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms and optionally possessing one or more degrees of unsaturation, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

The terms "heterocycle" and "heterocyclic" as used herein are used interchangeably to refer to a three to twelve-membered heterocyclic ring optionally possessing one or more degrees of unsaturation, containing one or more heteroatomic substitutions selected from —S—, —SO—, —SO$_2$—, —O—, or —N—, optionally substituted with substitutents, including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring optionally may be fused to one or more of another "heterocyclic" ring(s). Examples of "heterocyclic" include, but are not limited to, pyrrole, furan, thiophene, imidazole, oxazole, thiazole, pyrazole, 3-pyrroline, pyrrolidine, pyridine, pyrimidine, purine, quinoline, isoquinoline, carbazole, tetrahydrofuran, 1,4-dioxane, 1,3-dioxane, piperidine, pyrrolidine, morpholine, piperazine and the like.

The term "C-linked heterocycle" means a heterocycle that is bonded through a carbon atom, e.g. —(CH$_2$)$_n$-heterocycle where n is 1, 2 or 3 or —C<heterocycle where C<represents a carbon atom in a heterocycle ring. Similarly, R moieties that are N-linked heterocycles mean a heterocycle that is bonded through a heterocycle ring nitrogen atom, e.g. —N<heterocycle where N<represents a nitrogen atom in a heterocycle ring.

Examples of heterocycles include, but are not limited to, pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4αH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at the nitrogen atom or position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Typically, nitrogen bonded heterocycles include 1-aziridyl, 1-azetedyl, 1-pyrrolyl, 1-imidazolyl, 1-pyrazolyl, and 1-piperidinyl and tautomers of any of these.

As used herein, the term "heterocyclylene" refers to a three to twelve-membered heterocyclic ring diradical optionally having one or more degrees of unsaturation containing one or more heteroatoms selected from S, SO, SO$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-dyil, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include, but are not limited to, 5-indanyl, 5,6,7,8-tetrahydro-2-naphthyl,

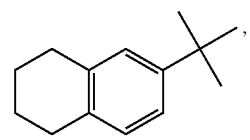

and the like.F

As used herein, the term "fused cycloalkylarylene" refers to a fused cycloalkylaryl, wherein the aryl group is divalent. Examples include, but are not limited to,

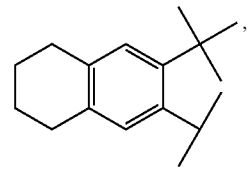

and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include, but are not limited to, 1-indanyl, 2-indanyl, 1-(1,2,3,4-tetrahydronaphthyl),

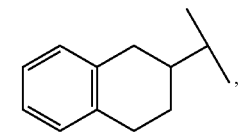

and the like.

As used herein, the term "fused arylcycloalkylene" refers to a fused arylcycloalkyl, wherein the cycloalkyl group is divalent. Examples include, but are not limited to,

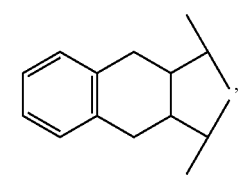

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include, but are not limited to, 3,4-methylenedioxy-1-phenyl,

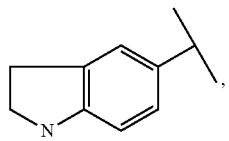

and the like

As used herein, the term "fused heterocyclylarylene" refers to a fused heterocyclylaryl, wherein the aryl group is divalent. Examples include, but are not limited to,

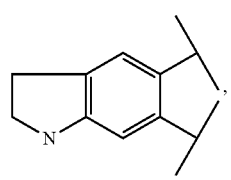

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include, but are not limited to, 2-(1,3-benzodioxolyl),

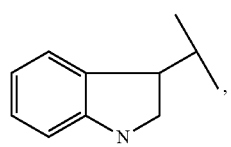

and the like.

As used herein, the term "fused arylheterocyclylene" refers to a fused arylheterocyclyl, wherein the heterocyclyl group is divalent. Examples include, but are not limited to,

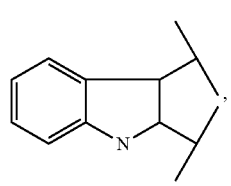

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include, but are not limited to, 5-aza-6-indanyl,

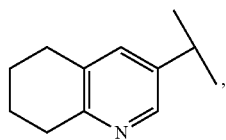

and the like.

As used herein, the term "fused cycloalkylheteroarylene" refers to a fused cycloalkylheteroaryl, wherein the heteroaryl group is divalent. Examples include, but are not limited to,

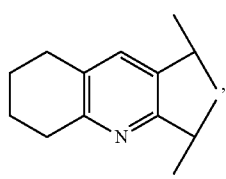

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include, but are not limited to, 5-aza-1-indanyl,

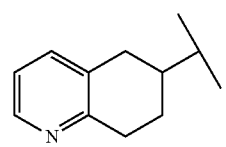

and the like.

As used herein, the term "fused heteroarylcycloalkylene" refers to a fused heteroarylcycloalkyl, wherein the cycloalkyl group is divalent. Examples include, but are not limited to,

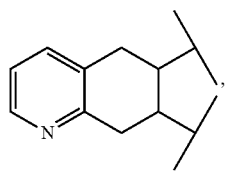

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include, but are not limited to, 1,2,3,4-tetrahydro-beta-carbolin-8-yl,

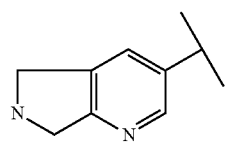

and the like.

As used herein, the term "fused heterocyclylheteroarylene" refers to a fused heterocyclylheteroaryl, wherein the heteroaryl group is divalent. Examples include, but are not limited to,

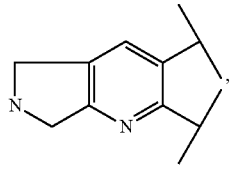

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include, but are not limited to, -5-aza-2,3-dihydrobenzofuran-2-yl,

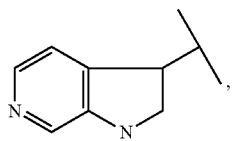

and the like.

As used herein, the term "fused heteroarylheterocyclylene" refers to a fused heteroarylheterocyclyl, wherein the heterocyclyl group is divalent. Examples include, but are not limited to,

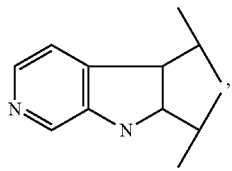

and the like.

As used herein, the term "acid isostere" refers to a substituent group which will ionize at physiological pH to bear a net negative charge. Examples of such "acid isosteres" include but are not limited to heteroaryl groups such as but not limited to isoxazol-3-ol-5-yl, 1H-tetrazole-5-yl or 2H-tetrazole-5-yl. Such acid isosteres include but are not limited to heterocyclyl groups such as but not limited to imidazolidine-2,4-dione-5-yl, imidazolidine-2,4-dione-1-yl, 1,3-thiazolidine-2,4-dione-5-yl, or 5-hydroxy-4H-pyran-4-on-2-yl.

As used herein, the term "direct bond", where part of a structural variable specification, refers to the direct joining of the substituents flanking (preceding and succeeding) the variable taken as a "direct bond".

The term "O-linked moiety" means a moiety that is bonded through an oxygen atom. Thus, when an R group is an O-linked moiety, that R is bonded through oxygen and it thus can be an ether, an ester (e.g., —O—C(O)-optionally substituted alkyl), a carbonate or a carbamate (e.g., —O—C(O)—NH$_2$ or —O—C(O)—NH-optionally substituted alkyl). Similarly, the term "S-linked moiety" means a moiety that is bonded through a sulfur atom. Thus, when an R group is an S-linked moiety, that R is bonded through sulfur and it thus can be a thioether (e.g., —S-optionally substituted alkyl), a thioester (—S—C(O)-optionally substituted alkyl) or a disulfide (e.g., —S—S-optionally substituted alkyl). The term "N-linked moiety" means a moiety that is bonded through a nitrogen atom. Thus, when an R group is an N-linked moiety, the R group is bonded through nitrogen and one or more of these can thus be an N-linked amino acid such as —NH—CH$_2$—COOH, a carbamate such as —NH—C(O)—O-optionally substituted alkyl, an amine such as —NH-optionally substituted alkyl, an amide such as —NH—C(O)-optionally substituted alkyl or —N$_3$. The term "C-linked moiety" means a moiety that is bonded through a carbon atom. When one or more R group is bonded through carbon, one or more of these thus can be—optionally substituted alkyl such as —CH$_2$—CH$_2$—O—CH$_3$, —C(O)-optionally substituted alkyl hydroxyalkyl, mercaptoalkyl, aminoalkyl or =CH-optionally substituted alkyl.

The term "alkoxy" as used herein refers to the group $R_aO$—, where $R_a$ is alkyl.

The term "alkenyloxy" as used herein refers to the group $R_aO$—, where $R_a$ is alkenyl.

The term "alkynyloxy" as used herein refers to the group $R_aO$—, where $R_a$ is alkynyl.

The term "alkylsulfanyl" as used herein refers to the group $R_aS$—, where $R_a$ is alkyl.

The term "alkenylsulfanyl" as used herein refers to the group $R_aS$—, where $R_a$ is alkenyl.

The term "alkynylsulfanyl" as used herein refers to the group $R_aS$—, where $R_a$ is alkynyl.

The term "alkylsulfenyl" as used herein refers to the group $R_aS(O)$—, where $R_a$ is alkyl.

The term "alkenylsulfenyl" as used herein refers to the group $R_aS(O)$—, where $R_a$ is alkenyl.

The term "alkynylsulfenyl" as used herein refers to the group $R_aS(O)$—, where $R_a$ is alkynyl.

The term "alkylsulfonyl" as used herein refers to the group $R_aSO_2$—, where $R_a$ is alkyl.

The term "alkenylsulfonyl" as used herein refers to the group $R_aSO_2$—, where $R_a$ is alkenyl.

The term "alkynylsulfonyl" as used herein refers to the group $R_aSO_2$—, where $R_a$ is alkynyl.

The term "acyl" as used herein refers to the group $R_aC(O)$—, where $R_a$ is alkyl, alkenyl, alkynyl, cycloalkyl, cycloalkenyl, or heterocyclyl.

The term "aroyl" as used herein refers to the group $R_aC(O)$—, where $R_a$ is aryl.

The term "heteroaroyl" as used herein refers to the group $R_aC(O)$—, where $R_a$ is heteroaryl.

The term "alkoxycarbonyl" as used herein refers to the group $R_aOC(O)$—, where $R_a$ is alkyl.

The term "acyloxy" as used herein refers to the group $R_aC(O)O$—, where $R_a$ is alkyl, alkenyl, alkynyl, cycloalkyl, cycloalkenyl, or heterocyclyl.

The term "aroyloxy" as used herein refers to the group $R_aC(O)O$—, where $R_a$ is aryl.

The term "heteroaroyloxy" as used herein refers to the group $R_aC(O)O$—, where $R_a$ is heteroaryl.

The term "substituted" as used herein refers to substitution with the named substituent or substituents, multiple degrees of substitution being allowed unless otherwise stated.

The terms "contain" or "containing" can as used herein refers to in-line substitutions at any position along the above defined alkyl, alkenyl, alkynyl or cycloalkyl substituents with one or more of any of O, S, SO, SO$_2$, N, or N-alkyl, including, for example —CH$_2$—O—CH$_2$—, —CH$_2$—SO$_2$—CH$_2$—, —CH$_2$—NH—CH$_3$ and so forth.

The term "oxo" as used herein refers to the substituent =O.

The term "halogen" or "halo" as used herein includes iodine, bromine, chlorine and fluorine.

The term "mercapto" as used herein refers to the substituent —SH.

The term "carboxy" as used herein refers to the substituent —COOH.

The term "cyano" as used herein refers to the substituent —CN.

The term "aminosulfonyl" as used herein refers to the substituent —SO$_2$NH$_2$.

The term "carbamoyl" as used herein refers to the substituent —C(O)NH$_2$.

The term "sulfanyl" as used herein refers to the substituent —S—.

The term "sulfenyl" as used herein refers to the substituent —S(O)—.

The term "sulfonyl" as used herein refers to the substituent —S(O)$_2$—.

The term "ethoxy" as used herein refers to the substituent —O—CH$_2$CH$_3$.

The term "methoxy" as used herein refers to the substituent —O—CH$_3$.

As used herein, the term "optionally" means that the subsequently described event(s) may or may not occur, and includes both event(s) which occur and events that do not occur.

Common amino acids include Alanine; Arginine; Asparagine; Aspartic acid; Cysteine; Glutamine; Glutamic acid; Glycine; Histidine; Isoleucine; Leucine; Lysine; Methionine; Phenyalanine; Proline; Serine; Threonine; Tryptophan; Tyrosine; and Valine. The amino acids may be L- or D-amino acids.

The term "configuration" refers to the three-dimensional shape of a molecule. In order to represent three-dimensional configurations on a two-dimensional surface, perspective drawings in which the direction of a bond is specified by the line connecting the bonded atoms are used. Formula III shows an illustrative perspective drawing:

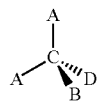

[Formula III]

In formula III, the focus of configuration is a carbon (C) atom so the lines specifying bond directions will originate there. A simple straight line represents a bond lying approximately in the surface plane, as shown by the two bonds to substituent "A." A wedge shaped bond is directed in front of this plane (thick end toward the viewer), as shown by the bond to substituent "B." A hatched bond is directed in back of the plane (away from the viewer), as shown by the bond to substituent "D." A dashed bond represents a single or double bond which can be in the cis or trans configuration.

Stereochemistry

According to some embodiments, the stereochemistry of the chiral centers (marked by "*") represents all possible combinations in terms of relative and absolute chemistry. Accordingly, it may represent either racemates or pure enantiomers.

The term "racemate" as used herein refers to an equimolar mixture of two optically active components that neutralize the optical effect of each other and is therefore optically inactive.

An "enantiomer" refers to one of a pair of optical isomers containing one or more asymmetric carbons (C*) whose molecular configurations have left- and right-hand (chiral) forms. Enantiomers have identical physical properties, except for the direction of rotation of the plane of polarized light. For example, the two 2-methyl-1-butanols have identical boiling points, densities, refractive indexes, and any other physical constant one might measure, except that one rotates the plane-polarized light to the right, the other to the left. Only the direction of rotation is different; the amount of rotation is the same. Enantiomers have identical chemical properties except toward optically active reagents. The atoms of each enantiomer that undergo attack in each enantiomer are influenced in their reactivity by exactly the same combination of substituents. The reagent approaching either kind of molecule encounters the same environment, except that one environment is the mirror image of the other. In the case of a reagent that is itself optically active, the influences exerted on the reagent are not identical in the attack on the two enantiomers, and reaction rates will be different; in some cases the reaction with one isomer does not take place at all. In biological systems, such stereochemical specificity is the rule rather than the exception, since enzymes, and most of the compounds they work on, are chiral. Enantiomers show different properties (physical or chemical) only in a chiral medium. Polarized light provides such a medium, and in it enantiomers differ in a physical property: direction of the rotation of the light. They also may differ in solubility in an optically active solvent, or in adsorption on an optically active surface. For enantiomers to react at different rates, the necessary chiral medium can be provided in a number of ways: by an optically active reagent; by a chiral solvent, or the chiral surface of a catalyst. The terms "optically active reagent" or "chiral reagent" refer to reaction under any chiral condition. The terms "optically inactive reagent" or "achiral reagent" refer to reaction in the absence of a chiral medium.

When named by the spatial configuration of its atoms, optical isomers conventionally are designated dextro (D) and levo (L) because they compare to each other structurally as do the right and left hand when the carbon atoms are lined up, i.e., they are mirror images of each other. Compounds in which an asymmetric carbon is present display optical rotation, meaning the change of direction of the plane of polarized light to either the right or the left as it passes through a molecule containing one or more asymmetric carbon atoms.

Each chiral center is labeled R or S according to a system by which its substituents are each designated a priority according to the Calm Ingold Prelog priority rules (CIP), based on atomic number. If the center is oriented so that the lowest priority of the four is pointed away from a viewer, the viewer will see two possibilities: if the priority of the remaining three substituents decreases in clockwise direction, it is labeled R (for Rectus), if it decreases in counterclockwise direction, it is S (for Sinister).

This system labels each chiral center in a molecule (and also has an extension to chiral molecules not involving chiral centers). Thus, it has greater generality than the D/L system, and can label, for example, an (R,R) isomer versus an (R,S)-diastereomers.

The R/S system has no fixed relation to the (+)/(−) system. An R isomer can be either dextrorotatory or levorotatory, depending on its exact substituents.

The R/S system also has no fixed relation to the D/L system. For example, the side-chain one of serine contains a hydroxyl group, —OH. If a thiol group, —SH, were swapped in for it, the D/L labeling would, by its definition, not be affected by the substitution. But this substitution would invert the molecule's R/S labeling, because the CIP priority of $CH_2OH$ is lower than that for $CO_2H$ but the CIP priority of $CH_2SH$ is higher than that for $CO_2H$.

For this reason, the D/L system remains in common use in certain areas of biochemistry, such as amino acid and carbohydrate chemistry, because it is convenient to have the same chiral label for all of the commonly occurring structures of a given type of structure in higher organisms. In the D/L system, they are nearly all consistent—naturally occurring amino acids are nearly all L, while naturally occurring carbohydrates are nearly all D. In the R/S system, they are mostly S, but there are some common exceptions.

An enantiomer can be named by the direction in which it rotates the plane of polarized light. If it rotates the light clockwise (as seen by a viewer towards whom the light is traveling), that enantiomer is labeled (+). Its mirror-image is labeled (−). The (+) and (−) isomers have also been termed d- and l-, respectively (for dextrorotatory and levorotatory).

An optical isomer can be named by the spatial configuration of its atoms. The D/L system does this by relating the molecule to glyceraldehyde. Glyceraldehyde is chiral itself, and its two isomers are labeled D and L (typically typeset in small caps in published work). Certain chemical manipulations can be performed on glyceraldehyde without affecting its configuration, and its historical use for this purpose (possibly combined with its convenience as one of the smallest commonly used chiral molecules) has resulted in its use for nomenclature. In this system, compounds are named by analogy to glyceraldehyde, which, in general, produces unambiguous designations, but is easiest to see in the small biomolecules similar to glyceraldehyde. One example is the amino acid alanine, which has two optical isomers, and they are labeled according to which isomer of glyceraldehyde they come from. On the other hand, glycine, the amino acid derived from glyceraldehyde, has no optical activity, as it is not chiral (achiral). Alanine, however, is chiral.

The D/L labeling is unrelated to (+)/(−); it does not indicate which enantiomer is dextrorotatory and which is levorotatory. Rather, it says that the compound's stereochemistry is related to that of the dextrorotatory or levorotatory enantiomer of glyceraldehyde—the dextrorotatory isomer of glyceraldehyde is, in fact, the D isomer. Nine of the nineteen L-amino acids commonly found in proteins are dextrorotatory (at a wavelength of 589 nm), and D-fructose is also referred to as levulose because it is levorotatory.

A rule of thumb for determining the D/L isomeric form of an amino acid is the "CORN" rule. The groups:

COOH, R, $NH_2$ and H (where R is a variant carbon chain) are arranged around the chiral center carbon atom. Sighting with the hydrogen atom away from the viewer, if these groups are arranged clockwise around the carbon atom, then it is the D-form. If counter-clockwise, it is the L-form.

The term "absolute configuration" refers to the spatial arrangement of the atoms of a chiral molecular entity (or group) and its stereochemical description, for example, R or S.

The term "relative configuration" refers to the configuration of any stereogenic (asymmetric) center with respect to any other stereogenic center contained within the same molecular entity. Unlike absolute configuration, relative configuration is reflection-invariant. Relative configuration, distinguishing diastereoisomers may be denoted by the configurational descriptors R*,R* (or l) and R*,S* (or u) meaning, respectively, that the two centers have identical or opposite configurations. For molecules with more than two asymmetric centers, the prefix rel- may be used in front of the name of one enantiomer where R and S have been used. If any centers have known absolute configuration then only R* and S* can be used for the relative configuration. For example, two different molecules Xabcd and Xabce may be said to have the same relative configurations if e takes the position of d in the tetrahedral arrangement of ligands around X (i.e., the pyramidal fragments Xabc are superposable). Similarly, the enantiomer of Xabce may be said to have the opposite relative configuration to Xabcd. The terms may be applied to chiral molecular entities with central atoms other than carbon but are limited to cases where the two related molecules differ in a single ligand. These definitions can be generalized to include stereogenic units other than asymmetric centers.

The term "stereogenic unit" (or "stereogen" or "stereoelement") refers to a grouping within a molecular entity that may be considered a focus of stereoisomerism. At least one of these must be present in every enantiomer (though the presence of stereogenic units does not conversely require the corresponding chemical species to be chiral). Three basic types are recognized for molecular entities involving atoms having not more than four substituents: (a) a grouping of atoms consisting of a central atom and distinguishable ligands, such that the interchange of any two of the substituents leads to a stereoisomer. An asymmetric atom (chirality center) is the traditional example of this stereogenic unit; (b) a chain of four non-coplanar atoms (or rigid groups) in a stable conformation, such that an imaginary or real (restricted) rotation (with a change of sign of the torsion angle) about the central bond leads to a stereoisomer; and (c) a grouping of atoms consisting of a double bond with substituents which give rise to cis-trans isomerism.

The term "chiral" is used to describe an object that is nonsuperposable on its mirror image and therefore has the property of chirality.

The term "chirality" refers to the geometric property of a rigid object (or spatial arrangement of points or atoms) of being non-superposable on its mirror image; such an object has no symmetry elements of the second kind (a mirror plane, $\sigma = S_1$, a center of inversion, $i = S_2$, a rotation-reflection axis, $S_{2n}$). If the object is superposable on its mirror image the object is described as being achiral.

The term "chirality axis" refers to an axis about which a set of ligands is held so that it results in a spatial arrangement which is not superposable on its mirror image. For example, with an allene abC=C=Ccd the chiral axis is defined by the C=C=C bonds; and with an ortho-substituted biphenyl C-1, C-1', C-4 and C-4' lie on the chiral axis.

The term "chirality center" refers to an atom holding a set of ligands in a spatial arrangement, which is not superposable on its mirror image. A chirality center may be considered a generalized extension of the concept of the asymmetric carbon atom to central atoms of any element.

The terms "chiroptic" or "chiroptical" refer to the optical techniques (using refraction, absorption or emission of anisotropic radiation) for investigating chiral substances (for example, measurements of optical rotation at a fixed wavelength, optical rotary dispersion (ORD), circular dichroism (CD) and circular polarization of luminescence (CPL).

The term "chirotopic" refers to the an atom (or point, group, face, etc. in a molecular model) that resides within a chiral environment. One that resides within an achiral environment has been called achirotopic.

The term "asymmetric" as used herein refers to lacking all symmetry elements (other than the trivial one of a one-fold axis of symmetry), i.e., belonging to the symmetry of point group $C_1$. The term has been used loosely (and incorrectly) to describe the absence of a rotation-reflection axis (alternating axis) in a molecule, i.e., as meaning chiral, and this usage persists in the traditional terms such as, but not limited to, asymmetric carbon atom, asymmetric synthesis, and asymmetric induction.

The terms "cis" and "trans" are descriptors which show the relationship between two ligands attached to separate atoms that are connected by a double bond or are contained in a ring. The two ligands are said to be located cis to each other if they lie on the same side of a plane. If they are on opposite sides, their relative position is described as trans. The appropriate reference plane of a double bond is perpendicular to that of the relevant σ-bonds and passes through the double bond. For a ring (the ring being in a conformation, real or assumed, without re-entrant angles at the two substituted atoms) it is the mean place of the ring(s). For alkenes the terms cis and trans may be ambiguous and have therefore generally have been replaced by the E, Z convention for the nomenclature of organic compounds. If there are more than two entities attached to the ring the use of cis and trans requires the definition of a reference substituent (see IUPAC, Nomenclature of Organic Chemistry, Sections A, B, C, D, E, F and H, Pergamon Press, 1979, p. 478, Rule E-2.3.3, E-2.3.4; IUPAC, *A Guide to IUPAC Nomenclature of Organic Chemistry*, Blackwell Scientific Publications, 1993, pp. 149-151, Rule R-7.1.1).

The terms "cis-trans isomers" refer to stereoisomeric olefins or cycloalkanes (or hetero-analogues) which differ in the positions of atoms (or groups) relative to a reference plane: in the cis-isomer the atoms are on the same side, in the trans-isomer they are on opposite sides. For example:

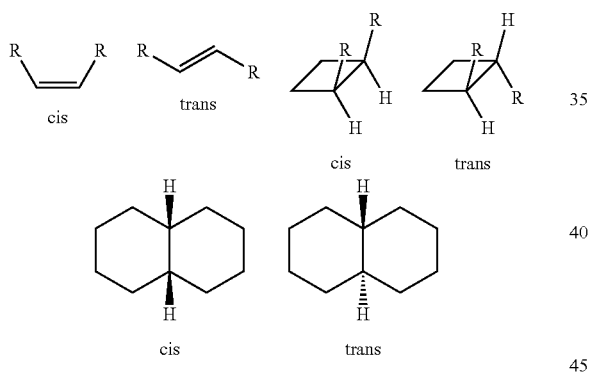

Superposability refers to the ability to bring two particular stereochemical formulae (or models) into coincidence (or to be exactly superposable in space, and for the corresponding molecular entities or objects to become exact replicas of each other) by no more than translation and rigid rotation.

The term "isomer" as used herein refers to one of two or more molecules having the same number and kind of atoms and hence the same molecular weight, but differing in respect to the arrangement or configuration of the atoms. Stereoisomers are isomers that are different from each other only in the way the atoms are oriented in space (but are like one another with respect to which atoms are joined to which other atoms).

The term "diastereoisomerism" refers to stereoisomerism other than enantiomerism. Diastereoisomers (or diastereomers) are stereoisomers not related as mirror images. Diastereoisomers are characterized by differences in physical properties, and by some differences in chemical behavior towards achiral as well as chiral reagents. Diastereomers have similar chemical properties, since they are members of the same family. Their chemical properties are not identical, however. Diastereomers have different physical properties: different melting points, boiling points, solubilities in a given solvent, densities, refractive indexes, and so on. Diastereomers also differ in specific rotation; they may have the same or opposite signs of rotation, or some may be inactive. The presence of two chiral centers can lead to the existence of as many as four stereoisomers. For compounds containing three chiral centers, there could be as many as eight stereoisomers; for compounds containing four chiral centers, there could be as many as sixteen stereoisomers, and so on. The maximum number of stereoisomers that can exist is equal to $2^n$, where n is the number of chiral centers. The term "diastereotopic" refers to constitutionally equivalent atoms or groups of a molecule which are not symmetry related. Replacement of one of two diastereotopic atoms or groups results in the formation of one of a pair of diastereoisomers. For example, the two hydrogen atoms of the methylene group C-3 are diastereotopic.

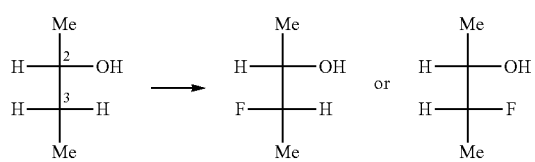

According to this definition, cis-trans isomerism is a form of diastereoisomerism.

According to one embodiment, the absolute stereochemistry for a compound of Formula I of the present invention may be as shown below:

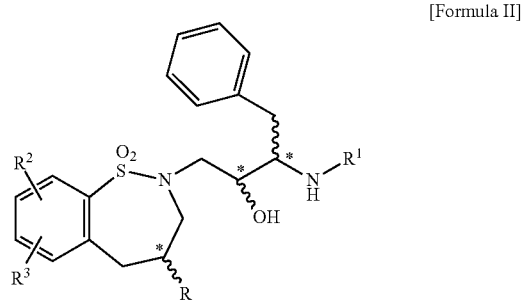

[Formula II]

wherein R, $R^1$, $R^2$ and $R^3$, each independently are:

R=H, alkyl, aryl, aryl alkyl, alkenyl, cycloalkyl, cycloalkenyl, alkylcycloalkyl, heterocycles, and substitutions thereof,

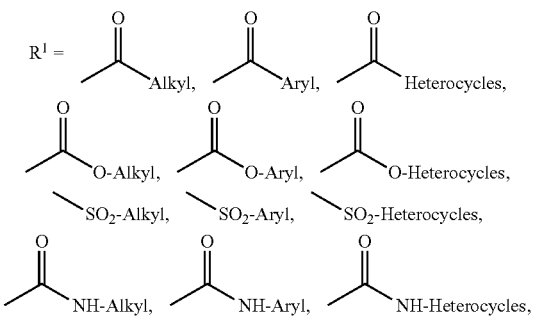

-continued

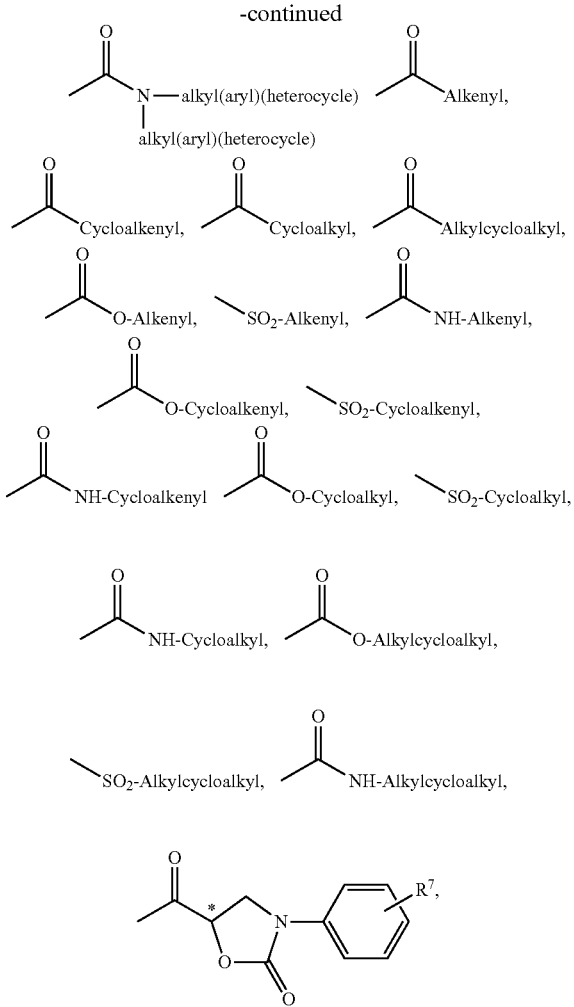

where R⁷=H, an electron donating group, or an electron withdrawing group at some or all the positions on the aromatic ring.

R² and R³ are each independently H, an electron donating group, or an electron withdrawing group at some or all the positions on the aromatic ring, and where "*" represents a chiral center. The stereochemistry marked by "*" may represent all possible combinations in terms of relative and absolute chemistry, i.e., diastereomers including racemic or pure enantiomers.

According to another embodiment, the compound of Formula I is a racemate. According to some such embodiments, the mixture of the two enantiomers is in a ratio of 90%:10%. According to some such embodiments, the mixture of the two enantiomers is in a ratio of 80%:20%. According to some such embodiments, the mixture of the two enantiomers is in a ratio of 70%:30%. According to some such embodiments, the mixture of the two enantiomers is in a ratio of 60%:40%. According to some such embodiments, the mixture of the two enantiomers is in a ratio of 50%:50%. According to some such embodiments, the mixture of the two enantiomers is in a ratio of 40%:60%. According to some such embodiments, the mixture of the two enantiomers is in a ratio of 30%:70%. According to some such embodiments, the mixture of the two enantiomers is in a ratio of 20%:80%. According to some such embodiments, the mixture of the two enantiomers is in a ratio of 10%:90%.

According to some embodiments, the compound of Formula I has a chiral center at the C3' atom. According to some embodiments, the compound of Formula I has a chiral center of R or S absolute configuration at the C3' atom. According to some embodiments, the compound of Formula I has a chiral center of R absolute configuration at the C3' atom. According to some embodiments, the compound of Formula I has a chiral center of S absolute configuration at the C3' atom.

According to some embodiments, the compound of Formula I has a chiral center at the C2' atom. According to some embodiments, the compound of Formula I has a chiral center of R or S absolute configuration at the C2' atom. According to some embodiments, the compound of Formula I has a chiral center of R absolute configuration at the C2' atom. According to some embodiments, the compound of Formula I has a chiral center of S absolute configuration at the C2' atom.

According to some embodiments, the compound of Formula I has a chiral center at the C4 atom. According to some embodiments, the compound of Formula I has a chiral center of R or S absolute configuration at the C4 atom. According to some embodiments, the compound of Formula I has a chiral center of R absolute configuration at the C4 atom. According to some embodiments, the compound of Formula I has a chiral center of S absolute configuration at the C4 atom.

According to another embodiment, the compound of Formula I has a chiral center at the C2' atom, the C3' atom and the C4 atom. According to some such embodiments, the compound of Formula I has a chiral center of S absolute configuration at the C3' atom. According to some such embodiments, the compound of Formula I has a chiral center of R absolute configuration at the C2' atom. According to some such embodiments, the compound of Formula I has a chiral center of S or R absolute configuration at the C4 atom. According to some such embodiments, the compound of Formula I has a chiral center of S absolute configuration at the C4 atom. According to some such embodiments, the compound of Formula I has a chiral center of R absolute configuration at the C4 atom.

According to another embodiment, the absolute stereochemistry for a compound of the present invention may be shown as below:

[Compound 1]

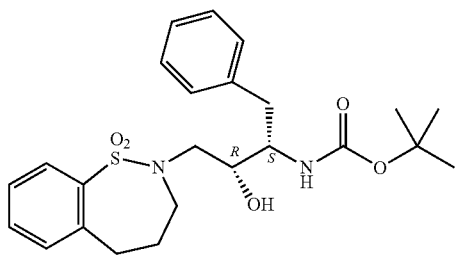

where the simple straight line represents a bond lying approximately in the surface plane; and the hatched bond is directed in the back of the surface plane, having stereochemistry of S(C3')-R(C2').

According to another embodiment, the absolute stereochemistry for a compound of the present invention may be shown as below:

[Compound 2]

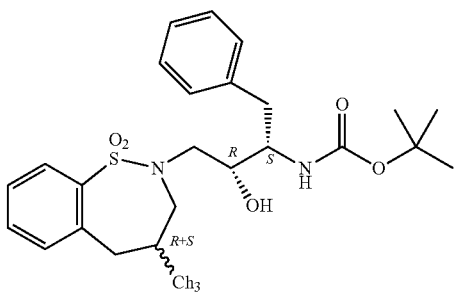

where the simple straight line represents a bond lying approximately in the surface plane; the wavy bond is a single bond that is stereochemically ambiguous or contain both R and S diasteroisomers and the hatched bond is directed in the back of the surface plane. According to some such embodiments, the compound has stereochemistry of S(C3')-R(C2')-S(C4). According to some such embodiments, the compound has stereochemistry of S(C3')-R (C2')-R(C4).

According to another embodiment, the absolute stereochemistry for a compound of the present invention may be shown as below:

[Compound 3]

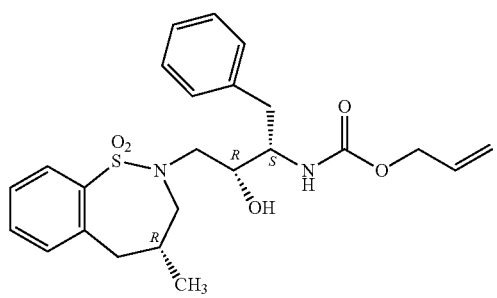

where the simple straight line represents a bond lying approximately in the surface plane; and the hatched bond is directed in the back of the surface plane. According to some such embodiments, the compound has stereochemistry of S(C3')-R(C2')-R(C4).

According to another embodiment, the absolute stereochemistry for a compound of the present invention may be as shown below:

[Compound 4]

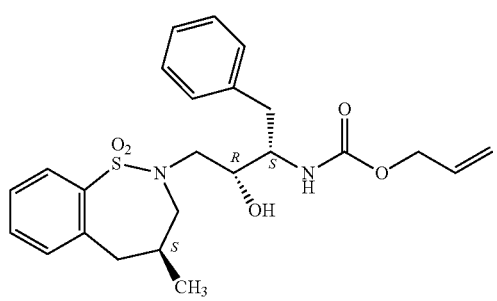

where the simple straight line represents a bond lying approximately in the surface plane; the wedge shaped bond is directed to the front of the surface plane; and the hatched bond is directed in the back of the surface plane. According to some such embodiments, the compound has stereochemistry of S(C3')-R(C2')-S(C4).

According to another embodiment, the absolute stereochemistry for a compound of the present invention may be shown as below:

[Compound 5]

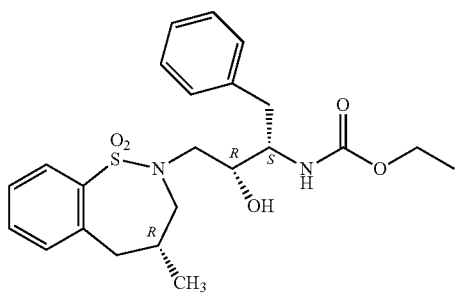

where the simple straight line represents a bond lying approximately in the surface plane; and the hatched bond is directed in the back of the surface plane. According to some such embodiments, the compound has stereochemistry of S(C3')-R(C2')-R(C4).

According to another embodiment, the absolute stereochemistry for a compound of the present invention may be as shown below:

[Compound 6]

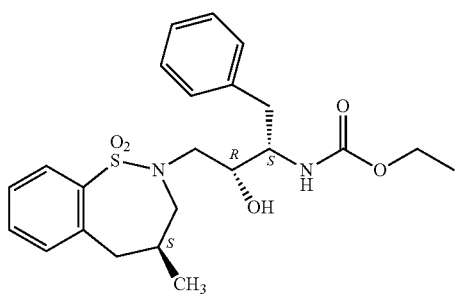

where the simple straight line represents a bond lying approximately in the surface plane; the wedge shaped bond is directed to the front of the surface plane; and the hatched bond is directed in the back of the surface plane. According to some such embodiments, the compound has stereochemistry of S(C3')-R(C2')-S(C4).

According to another embodiment, the absolute stereochemistry for a compound of the present invention may be as shown below:

[Compound 7]

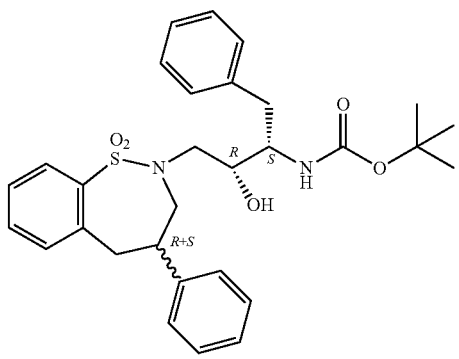

where the simple straight line represents a bond lying approximately in the surface plane; the wavy bond is a single bond that is stereochemically ambiguous; and the hatched bond is directed in the back of the surface plane. According to some such embodiments, the compound has stereochemistry of S(C3')-R(C2')-S(C4). According to some such embodiments, the compound has stereochemistry of S(C3')-R(C2')-R(C4). According to some such embodiments, the compound has stereochemistry of S(C3')-R(C2')- and R+S(C4).

According to another embodiment, the absolute stereochemistry for a compound of the present invention may be shown as below:

[Compound 8]

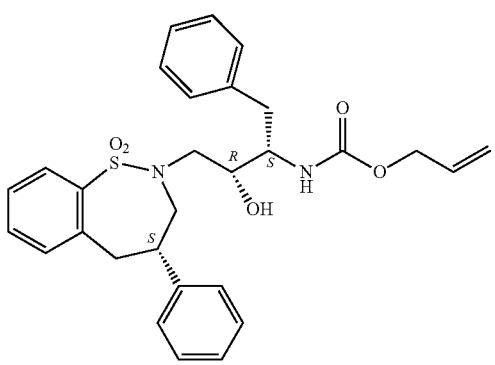

where the simple straight line represents a bond lying approximately in the surface plane; and the hatched bond is directed in the back of the surface plane. According to some such embodiments, the compound has stereochemistry of S(C3')-R(C2')-S(C4).

According to another embodiment, the absolute stereochemistry for a compound of the present invention may be as shown below:

[Compound 9]

where the simple straight line represents a bond lying approximately in the surface plane; the wedge shaped bond is directed to the front of the surface plane; and the hatched bond is directed in the back of the surface plane. According to some such embodiments, the compound has stereochemistry of S(C3')-R(C2')-R(C4).

According to another embodiment, the absolute stereochemistry for a compound of the present invention may be shown as below:

[Compound 10]

where the simple straight line represents a bond lying approximately in the surface plane; and the hatched bond is directed in the back of the surface plane. According to some such embodiments, the compound has stereochemistry of S(C3')-R(C2')-S(C4).

According to another embodiment, the absolute stereochemistry for a compound of the present invention may be as shown below:

[Compound 11]

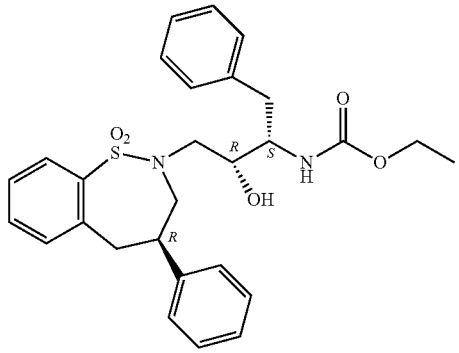

where the simple straight line represents a bond lying approximately in the surface plane; the wedge shaped bond is directed to the front of the surface plane; and the hatched bond is directed in the back of the surface plane. According to some such embodiments, the compound has stereochemistry of S(C3')-R(C2')-R(C4).

According to another embodiment, the absolute stereochemistry for a compound of the present invention may be shown as below:

[Compound 12]

where the simple straight line represents a bond lying approximately in the surface plane; and the hatched bond is directed in the back of the surface plane. According to some such embodiments, the compound has stereochemistry of S(C3')-R(C2')-R(C4).

According to another embodiment, the absolute stereochemistry for a compound of the present invention may be as shown below:

[Compound 13]

where the simple straight line represents a bond lying approximately in the surface plane; and the hatched bond is directed in the back of the surface plane. According to some such embodiments, the compound has stereochemistry of S(C3')-R(C2')-S(C4).

According to another embodiment, the absolute stereochemistry for a compound of the present invention may be

[Compound 14]

where the simple straight line represents a bond lying approximately in the surface plane; and the hatched bond is directed in the back of the surface plane. According to some such embodiments, the compound has stereochemistry of S(C3')-R(C2')-R(C4).

According to another embodiment, the absolute stereochemistry for a compound of the present invention may be as shown below:

[Compound 15]

where the simple straight line represents a bond lying approximately in the surface plane; the wedge shaped bond is directed to the front of the surface plane; and the hatched bond is directed in the back of the surface plane. According to some such embodiments, the compound has stereochemistry of S(C3')-R(C2')-S(C4).

According to another embodiment, the absolute stereochemistry for a compound of the present invention may be shown as below:

[Compound 16]

where the simple straight line represents a bond lying approximately in the surface plane; and the hatched bond is directed in the back of the surface plane. According to some such embodiments, the compound has stereochemistry of S(C3')-R(C2')-R(C4).

According to another embodiment, the absolute stereochemistry for a compound of the present invention may be shown as below:

[Compound 17]

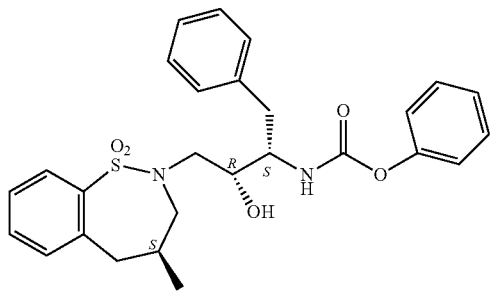

where the simple straight line represents a bond lying approximately in the surface plane; the wedge shaped bond is directed to the front of the surface plane; and the hatched bond is directed in the back of the surface plane. According to some such embodiments, the compound has stereochemistry of S(C3')-R(C2')-S(C4).

According to another embodiment, the absolute stereochemistry for a compound of the present invention may be shown as below:

[Compound 18]

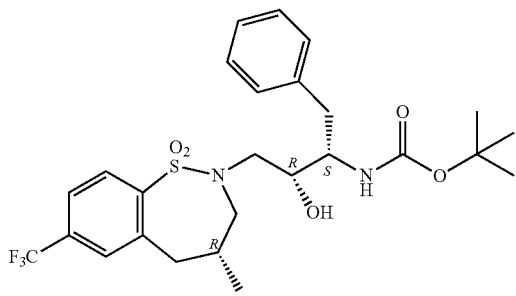

where the simple straight line represents a bond lying approximately in the surface plane; and the hatched bond is directed in the back of the surface plane. According to some such embodiments, the compound has stereochemistry of S(C3')-R(C2')-R(C4).

According to another embodiment, the absolute stereochemistry for a compound of the present invention may be shown as below:

[Compound 19]

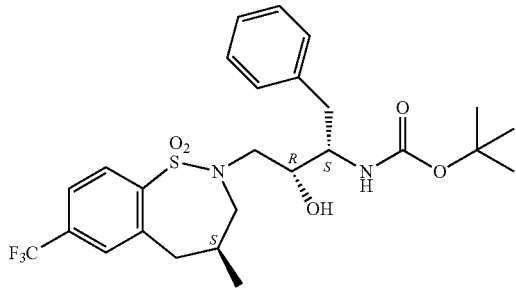

where the simple straight line represents a bond lying approximately in the surface plane; the wedge shaped bond is directed to the front of the surface plane; and the hatched bond is directed in the back of the surface plane. According to some such embodiments, the compound has stereochemistry of S(C3')-R(C2')-S(C4).

According to another embodiment, the absolute stereochemistry for a compound of the present invention may be shown as below:

[Compound 20]

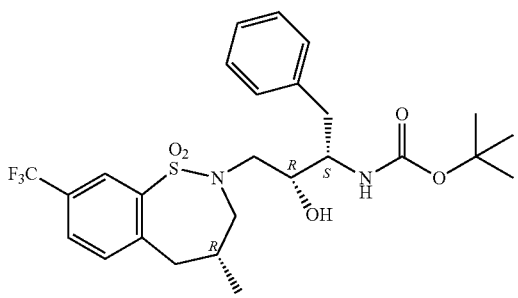

where the simple straight line represents a bond lying approximately in the surface plane; and the hatched bond is directed in the back of the surface plane. According to some such embodiments, the compound has stereochemistry of S(C3')-R(C2')-R(C4).

According to another embodiment, the absolute stereochemistry for a compound of the present invention may be as shown below:

[Compound 21]

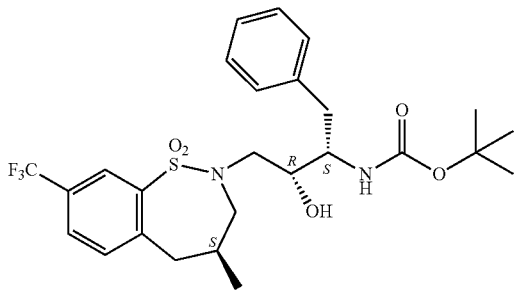

where the simple straight line represents a bond lying approximately in the surface plane; the wedge shaped bond is directed to the front of the surface plane; and the hatched bond is directed in the back of the surface plane. According to some such embodiments, the compound has stereochemistry of S(C3')-R(C2')-S(C4).

According to another embodiment, the absolute stereochemistry for a compound of the present invention may be shown as below:

[Compound 22]

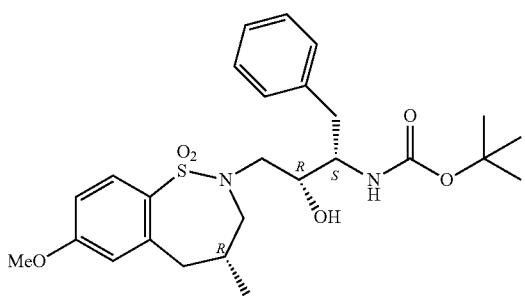

where the simple straight line represents a bond lying approximately in the surface plane; and the hatched bond is directed in the back of the surface plane. According to some such embodiments, the compound has stereochemistry of S(C3')-R(C2')-R(C4).

According to another embodiment, the absolute stereochemistry for a compound of the present invention may be as shown below:

[Compound 23]

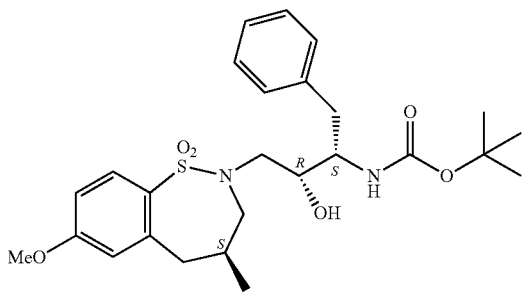

where the simple straight line represents a bond lying approximately in the surface plane; the wedge shaped bond is directed to the front of the surface plane; and the hatched bond is directed in the back of the surface plane. According to some such embodiments, the compound has stereochemistry of S(C3')-R(C2')-S(C4).

According to another embodiment, the absolute stereochemistry for a compound of the present invention may be as shown below:

[Compound 24]

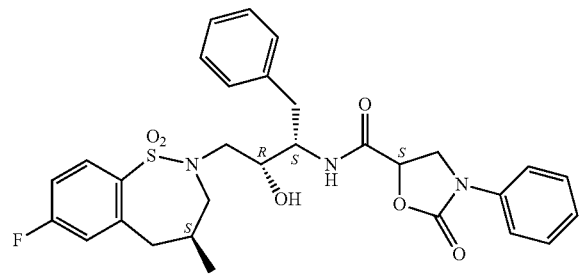

where the simple straight line represents a bond lying approximately in the surface plane; the wedge shaped bond is directed to the front of the surface plane; and the hatched bond is directed in the back of the surface plane. According to some such embodiments, the compound has 4 chiral centers. According to some such embodiments, the compound is a SRSS compound (stereochemistry of S(C3')-R(C2')-S(C4)-S(C5')).

Compositions

The present invention further provides compositions comprising at least one of the as-described inhibitors. The term "therapeutically effective amount" refers to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. The effective amount for any particular application may vary depending on such factors as the disease or condition being treated, the particular inventive compound, the size of the subject, or the severity of the disease or condition. One of ordinary skill in the art may determine empirically the therapeutically effective amount of a particular inventive compound and/or other therapeutic agent without necessitating undue experimentation. It is generally preferred that a maximum dose be used, that is, the highest safe dose according to some medical judgment. The terms "dose" and "dosage" are used interchangeably herein.

For any compound described herein the therapeutically effective amount may be initially determined from preliminary in vitro studies and/or animal models. A therapeutically effective dose also may be determined from human data for HIV-1 protease inhibitors. The applied dose may be adjusted based on the relative bioavailability and potency of the administered compound. Adjusting the dose to achieve maximal efficacy based on the methods described above and other methods are well-known in the art and is well within the capabilities of the ordinarily skilled artisan.

The formulations of inhibitors may be administered in pharmaceutically acceptable solutions, which may routinely contain pharmaceutically acceptable concentrations of salt, buffering agents, preservatives, compatible carriers, adjuvants, and optionally other therapeutic agents.

According to another embodiment, the compositions of the present invention can further include one or more additional compatible active ingredients. "Compatible" as used herein means that the components of such a composition are capable of being combined with each other in a manner such that there is no interaction that would substantially reduce the efficacy of the composition under ordinary use conditions.

In one embodiment, the compound of the inventive compositions is an active ingredient.

The term "active" as used herein refers to having pharmacological or biological activity or affect. The term "active ingredient" ("AI", "active pharmaceutical ingredient", "API", or "bulk active") is the substance in a drug that is pharmaceutically active. As used herein, the phrase "additional active ingredient" refers to an agent, other than a compound of the inventive composition, that exerts a pharmacological, or any other beneficial activity.

Additional active ingredients included in the compositions according to the present invention used to inhibit HIV protease include, without limitation, one or more, in any combination, of an antibiotic agent, an antifungal agent, an antiviral agent, an antiprotozoal agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, or a hormone.

The term "antibiotic agent" as used herein means any of a group of chemical substances having the capacity to inhibit the growth of, or to destroy bacteria, and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

The term "anti-fungal agent" as used herein means any of a group of chemical substances having the capacity to inhibit the growth of or to destroy fungi. Anti-fungal agents include but are not limited to Posaconazole, Amphotericin B, Candicidin, Dermostatin, Filipin, Fungichromin, Hachimycin, Hamycin, Lucensomycin, Mepartricin, Natamycin, Nystatin, Pecilocin, Perimycin, Azaserine, Griseofulvin, Oligomycins, Neomycin, Pyrrolnitrin, Siccanin, Tubercidin, Viridin, Butenafine, Naftifine, Terbinafine, Bifonazole, Butoconazole, Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole, Sertaconazole, Sulconazole, Tioconazole, Tolciclate, Tolindate, Tolnaftate, Fluconawle, Itraconazole, Saperconazole, Terconazole, Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, and Zinc Propionate.

The term "anti-viral agent" as used herein means any of a group of chemical substances having the capacity to inhibit the replication of or to destroy viruses used chiefly in the treatment of viral diseases. Anti-viral agents include, but are not limited to, Acyclovir, Cidofovir, Cytarabine, Dideoxyadenosine, Didanosine, Edoxudine, Famciclovir, Floxuridine, Ganciclovir, Idoxuridine, Inosine Pranobex, Lamivudine, MADU, Penciclovir, Sorivudine, Stavudine, Trifluridine, Valacyclovir, Vidarabine, Zalcitabine, Zidovudine, Acemannan, Acetylleucine, Amantadine, Amidinomycin, Delavirdine, Foscarnet, Indinavir, Interferons (e.g., IFN-alpha), Kethoxal, Lysozyme, Methisazone, Moroxydine, Nevirapine, Podophyllotoxin, Ribavirin, Rimantadine, Ritonavir2, Saquinavir, Stailimycin, Statolon, Tromantadine, Zidovudine (AZT) and Xenazoic Acid.

The term "anti-protozoal agent" as used herein means any of a group of chemical substances having the capacity to inhibit the growth of or to destroy protozoans used chiefly in the treatment of protozoal diseases. Examples of antiprotozoal agents, without limitation include pyrimethamine (Daraprim®) sulfadiazine, and Leucovorin.

"Anesthetic agents" refers to agents that result in a reduction or loss of sensation. Non-limiting examples of anesthetic drugs that are suitable for use in the context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

"Steroidal anti-inflammatory agent", as used herein, refer to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

"Non-steroidal anti-inflammatory agents" refers to a large group of agents that are aspirin-like in their action, including ibuprofen (Advil)®, naproxen sodium (Aleve)®, and acetaminophen (Tylenol®). Additional examples of non-steroidal anti-inflammatory agents that are usable in the context of the present invention include, without limitation, oxicams, such as piroxicam, isoxicam, tenoxicam, sudoxicam, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents also may be employed, as well as the dermatologically acceptable salts and esters of these agents. For example, etofenamate, a flufenamic acid derivative, is particularly useful for topical application.

"Antipruritic agents" as used herein refers to those substances that reduce, eliminate or prevent itching. Suitable antipruritic agents include, without limitation, pharmaceutically acceptable salts of methdilazine and trimeprazine.

An "anti-oxidant agent" as used herein refers to a substance that inhibits oxidation or reactions promoted by oxygen or peroxides. Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename TroloxR), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, glycine pidolate, arginine pilorate, nordihydroguaiaretic acid, bioflavonoids, curcumin, lysine, methionine, proline, superoxide dismutase, silymarin, tea extracts, grape skin/seed extracts, melanin, and rosemary extracts.

"Chemotherapetic agent" refers to chemicals useful in the treatment or control of a disease. Non-limiting examples of chemotherapeutic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

"Antihistamine agent" as used herein refers to any of various compounds that counteract histamine in the body and that are used for treating allergic reactions (such as hay fever) and cold symptoms. Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

"Vitamin" as used herein, refers to any of various organic substances essential in minute quantities to the nutrition of most animals that act especially as coenzymes and precursors of coenzymes in the regulation of metabolic processes. Non-limiting examples of vitamins usable in context of the present invention include vitamin A and its analogs and derivatives: retinol, retinal, retinyl palmitate, retinoic acid, tretinoin, isotretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

"Hormone" as used herein refers to natural substances produced by organs of the body that travel by blood to trigger activity in other locations or their synthetic analogs. Suitable hormones for use in the context of the present invention include, but are not limited to, calciferol (Vitamin D3) and its products, androgens, estrogens and progesterones.

As used herein the term "treating" includes abrogating, substantially inhibiting, slowing or reversing the progression of a condition, substantially ameliorating clinical or aesthetical symptoms of a condition, or substantially preventing the appearance of clinical or aesthetical symptoms of a condition.

The term "condition" includes a variety of conditions related to HIV protease. This term is meant to include disorders or diseases, associated with HIV-1 protease or HIV-2 protease.

A subject in need thereof is a patient having, or at risk of having a disorder related to HIV, HIV-1, HIV-2 and/or a HIV protease, or HIV protease thereof.

Adiministration

For use in therapy, a therapeutically effective amount of the protease inhibitor may be administered to a subject by any mode. Administering the pharmaceutical composition may be accomplished by any means known to the skilled artisan. Routes of administration include, but are not limited to, intrathecal, intra-arterial, parenteral (e.g. intravenous), intramuscular, oral, buccal, topical, by inhalation or insufflation (i.e., through the mouth or through the nose), or rectal.

Parenteral Administration

The protease inhibitor, when it is desirable to deliver it locally, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension also may contain suitable stabilizers or agents, which increase the solubility of the compounds to allow for the preparation of highly concentrated solutions. Alternatively, the active compounds may be in powder form for constitution with a suitable vehicle, e.g., sterile pyrogen-free water, before use.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer 1990 Science 249, 1527-1533, which is incorporated herein by reference.

Pharmaceutically Acceptable Salts

Depending upon the structure, at least one inhibitor of the described invention, and optionally at least one other therapeutic agent, may be administered per se (neat) or, depending upon the structure of the inhibitor, in the form of a pharmaceutically acceptable salt. The inhibitors of the described invention may form pharmaceutically acceptable salts with organic or inorganic acids, or organic or inorganic bases. When used in medicine the salts should be pharmaceutically acceptable, but non-pharmaceutically acceptable salts conveniently may be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group.

By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002), incorporated herein by reference in its entirety.

The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides, such as methyl, ethyl, propyl, and butyl chlorides, bromides and iodides; dialkyl sulfates like dimethyl, diethyl, dibutyl and diamyl sulfates; long chain halides, such as decyl, lauryl, myristyl and stearyl chlorides, bromides and iodides; arylalkyl halides, such as benzyl and phenethyl bromides, and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts may be also obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids also may be made.

The formulations may be presented conveniently in unit dosage form and may be prepared by any of the methods well known in the art of pharmacy. All methods include the step of bringing into association a protease inhibitor, or a pharmaceutically acceptable salt or solvate thereof ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The pharmaceutical agent or a pharmaceutically acceptable ester, salt, solvate or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parental preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms are made by forming microencapsulated matrices of a described inhibitor in biodegradable polymers such as polylactide-polyglycolide. Depending upon the ratio of inhibitor to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly(orthoesters) and poly(anhydrides). Depot injectable formulations also are prepared by entrapping the inhibitor of the described invention in liposomes or microemulsions, which are compatible with body tissues.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Oral Administration

For oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents also may be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives also may be included where appropriate.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations also may include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides, such as cocoa butter, is first melted, and the active ingredient is dispersed homogeneously therein by stirring or similar mixing. The molten homogeneous mixture is then poured into convenient sized molds, allowed to cool and thereby solidify.

Also included are solid form preparations, which are intended to be converted, shortly before use, to liquid form preparations for either oral or parenteral administration. Such liquid forms include solutions, suspensions and emulsions.

The compounds of the described invention also may be deliverable transdermally. The transdermal compositions may take the form of creams, lotions, aerosols and/or emulsions and can be included in a transdermal patch of the matrix or reservoir type as are conventional in the art for this purpose.

The term "capsule" refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

The term "tablet" refers to a compressed or molded solid dosage form containing the active ingredients with suitable diluents. The tablet can be prepared by compression of mixtures or granulations obtained by wet granulation, dry granulation or by compaction.

The term "oral gel" refers to the active ingredients dispersed or solubilized in a hydrophillic semi-solid matrix.

The phrase "powder for constitution" refers to powder blends containing the active ingredients and suitable diluents which can be suspended in water or juices.

The term "diluent" refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10% by weight to about 90% by weight of the total composition, from about 25% by weight to about 75% by weight, from about 30% by weight to about 60% by weight, and from about 12% by weight to about 60% by weight.

The term "disintegrant" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2% by weight to about 15% by weight of the composition, and/or from about 4% by weight to about 10% by weight.

The term "binder" refers to substances that bind or "glue" powders together and make them cohesive by forming granules, thus serving as the "adhesive" in the formulation. Binders add cohesive strength already available in the diluent or bulking agent. Suitable binders include, but are not limited to, sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2% by weight to about 20% by weight of the composition, from about 3% by weight to about 10% by weight, and/or from about 3% by weight to about 6% by weight.

The term "lubricant" refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants usually are added at the very last step before compression, since they must be present on the surfaces of the granules and in between them and the parts of the tablet press. The amount of lubricant in the composition can range from about 0.2% by weight to about 5% by weight of the composition, from about 0.5% by weight to about 2% by weight, and/or from about 0.3% by weight to about 1.5% by weight.

The term "glident" refers to material that prevents caking and improve the flow characteristics of granulations, so that flow is smooth and uniform. Suitable glidents include, but are not limited to, silicon dioxide and talc. The amount of glident in the composition can range from about 0.1% by weight to about 5% by weight of the total composition, and/or from about 0.5% by weight to about 2% by weight.

The term "coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1% by weight to about 5% by weight of the composition, and/or from about 0.1% by weight to about 1% by weight.

The term "bioavailability" refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like also are well known.

Pharmaceutically Acceptable Carrier

The pharmaceutical compositions within the described invention contain a therapeutically effective amount of an HIV protease inhibitor and optionally other therapeutic agents included in a pharmaceutically-acceptable carrier. The term "pharmaceutically-acceptable carrier" as used herein refers to one or more compatible solid or liquid filler, diluents or encapsulating substances which are suitable for administration to a human or other vertebrate animal. The term "carrier" as used herein refers to an organic or inorganic ingredient, natural or synthetic, with which the active ingredient is combined to facilitate the application. The components of the pharmaceutical compositions also are capable of being commingled in a manner such that there is no interaction which would substantially impair the desired pharmaceutical efficiency.

The therapeutic agent(s), including the protease inhibitor(s) of the described invention may be provided in particles. The term "particles" as used herein refers to nano or microparticles (or in some instances larger) that may contain in whole or in part the protease inhibitor or the other therapeutic agent(s) as described herein. The particles may contain the therapeutic agent(s) in a core surrounded by a coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the protease inhibitor in a solution or in a semi-solid state. The particles may be of virtually any shape.

Both non-biodegradable and biodegradable polymeric materials may be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels as described by Sawhney et al in Macromolecules (1993) 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. The term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period. Alternatively, delayed absorption of a parenterally administered drug form is accomplished by dissolving or suspending the drug in an oil vehicle. The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. The term "long-term" release, as used herein, means that the implant is constructed and arranged to deliver therapeutic levels of the active ingredient for at least 7 days, and preferably about 30 to about 60 days. Long-term sustained release implants are well-known to those of ordinary skill in the art and include some of the release systems described above.

Methods for Inhibiting HIV Protease

According to another aspect, the described disclosure provides methods for inhibiting a HIV protease in a subject, the method comprising administering a pharmaceutical composition comprising a therapeutically effective amount of a compound of formula:

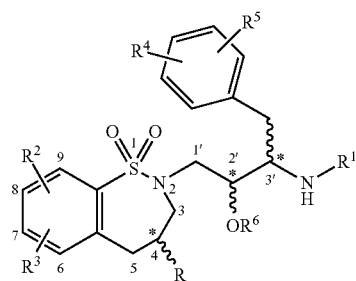

wherein R, $R^1$, $R^2$, $R^3$, $R^4$, $R^5$ and $R^6$ each independently are: R=H, alkyl, aryl, aryl alkyl, heterocycles, and substitutions thereof,

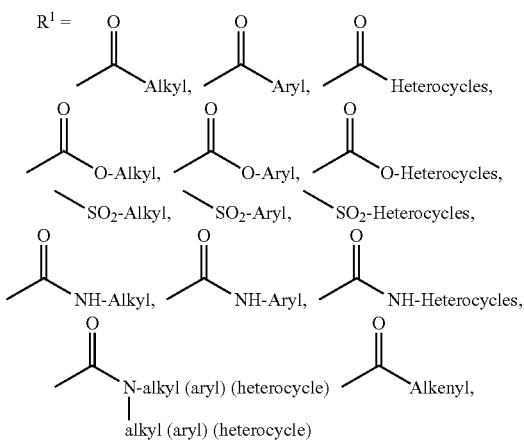

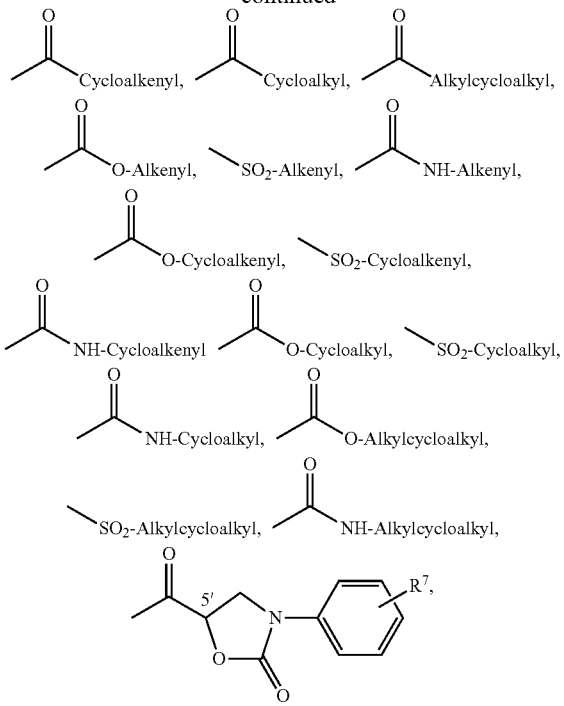

where $R^7$ is H, an electron donating group, an electron withdrawing group at some or all the positions on the aromatic ring, $R^2$, $R^3$, $R^4$, and $R^5$ are each independently H, an electron donating group, or an electron withdrawing group at some or all the positions on the aromatic ring;

$R^6$ is H, a phosphate or amino acid ester(s) or salt thereof;

wherein * is a chiral center, and a pharmaceutically acceptable carrier, thereby reducing the enzymatic activity of the HIV protease.

The term "inhibiting" as used herein refers to reducing or modulating the chemical or biological activity of a substance or compound.

The term "therapeutic agent" as used herein refers to a drug, molecule, nucleic acid, protein, metabolite, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably herein. The active agent may be, for example, but not limited to, at least one of a compound of formula I, or a pharmaceutically acceptable salt thereof.

The term "modify" as used herein means to change, vary, adjust, temper, alter, affect or regulate to a certain measure or proportion in one or more particulars.

The term "modifying agent" as used herein refers to a substance, composition, extract, botanical ingredient, botanical extract, botanical constituent, therapeutic component, active constituent, therapeutic agent, drug, metabolite, active agent, protein, non-therapeutic component, non-active constituent, non-therapeutic agent, or non-active agent that reduces, lessens in degree or extent, or moderates the form, symptoms, signs, qualities, character or properties of a condition, state, disorder, disease, symptom or syndrome.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50, which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "drug" as used herein refers to a therapeutic agent or any substance used in the prevention, diagnosis, alleviation, treatment, or cure of disease.

The term "treat" or "treating" as used herein refers to accomplishing one or more of the following: (a) reducing the severity of a disorder; (b) limiting development of symptoms characteristic of the disorder(s) being treated; (c) limiting worsening of symptoms characteristic of the disorder(s) being treated; (d) limiting recurrence of the disorder(s) in subjects that have previously had the disorder(s); and (e) limiting recurrence of symptoms in subjects that were previously symptomatic for the disorder(s).

The term "reduce" or "reducing" as used herein refers to limit occurrence of a disorder in individuals at risk of developing the disorder.

The term "administering" as used herein includes in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be locally administered by means such as, but not limited to, injection, implantation, grafting, topical application, or parenterally.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

The term "topical" refers to administration of a composition at, or immediately beneath, the point of application. The phrase "topically applying" describes application onto one or more surfaces(s) including epithelial surfaces. Although topical administration, in contrast to transdermal administration, generally provides a local rather than a systemic effect, the terms "topical administration" and "transdermal administration" as used herein, unless otherwise stated or implied, are used interchangeably.

The term "disease" or "disorder", as used herein, refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition", as used herein, refers to a variety of health states and is meant to include disorders or diseases caused by any underlying mechanism or disorder, injury, and the promotion of healthy tissues and organs. Diseases associated with HIV protease include, but are not limited to, acquired immune deficiency syndrome.

The term "symptom" as used herein refers to a phenomenon that arises from and accompanies a particular disease or disorder and serves as an indication of it.

The term "modulate" as used herein means to regulate, alter, adapt, or adjust to a certain measure or proportion.

The terms "subject" or "individual" or "patient" are used interchangeably to refer to a member of an animal species of mammalian origin, including humans.

The term "pharmaceutical composition" as used herein refers to a preparation comprising a pharmaceutical product, drug, metabolite, or active ingredient.

As used herein, the term "enzymatic activity" refers to the amount of substrate consumed (or product formed) in a given time under given conditions. Enzymatic activity also may be referred to as "turnover number."

According to one embodiment, the electron withdrawing group is a halogen. According to some embodiments, the electron donating group is a nitrile. According to some embodiments, the electron withdrawing group is a carboxylic acid. According to some embodiments, the electron withdrawing group is a carbonyl. According to some embodiments, the electron withdrawing group is an aldehyde. According to some embodiments, the electron withdrawing group is an acetaldehyde. According to some embodiments, the electron withdrawing group is a nitro group. According to some embodiments, the electron withdrawing group is a tetrafluoromethyl.

According to another embodiment, the electron donating group is an alkyl group. According to some embodiments, the electron donating group is an alcohol group. According to some embodiments, the electron donating group is a methoxy. According to some embodiments, the electron donating group is an amino group.

According to another embodiment, the HIV protease is HIV-1 protease. According to another embodiment, the HIV protease is HIV-2 protease.

According to another embodiment, the therapeutically effective amount of the HIV protease inhibitor is from about 1 pg/day to about 15 g/day.

According to another embodiment, the therapeutically effective amount of the HIV protease inhibitor is from about 0.000001 mg/kg body weight to about 10 g/kg body weight. According to another embodiment, the therapeutically effective amount of the HIV protease inhibitor is from about 0.000002 mg/kg body weight to about 10 g/kg body weight. According to another embodiment, the therapeutically effective amount of the HIV protease inhibitor is from about 0.000003 mg/kg body weight to about 10 g/kg body weight. According to another embodiment, the therapeutically effective amount of the HIV protease inhibitor is from about 0.000004 mg/kg body weight to about 10 g/kg body weight. According to another embodiment, the therapeutically effective amount of the HIV protease inhibitor is from about 0.000005 mg/kg body weight to about 10 g/kg body weight. According to another embodiment, the therapeutically effective amount of the HIV protease inhibitor is from about 0.000006 mg/kg body weight to about 10 g/kg body weight. According to another embodiment, the therapeutically effective amount of the HIV protease inhibitor is from about 0.000007 mg/kg body weight to about 10 g/kg body weight. According to another embodiment, the therapeutically effective amount of the HIV protease inhibitor is from about 0.000008 mg/kg body weight to about 10 g/kg body weight. According to another embodiment, the therapeutically effective amount of the HIV protease inhibitor is from about 0.000009 mg/kg body weight to about 10 g/kg body weight. According to another embodiment, the therapeutically effective amount of the HIV protease inhibitor is from about 0.00001 mg/kg body weight to about 10 g/kg body weight. According to another embodiment, the therapeutically effective amount of the HIV protease inhibitor is from about 0.00002 mg/kg body weight to about 10 g/kg body weight. According to another embodiment, the therapeutically effective amount of the HIV protease inhibitor is from about 0.0003 mg/kg body weight to about 10 g/kg body weight. According to another embodiment, the therapeutically effective amount of the HIV protease inhibitor is from about 0.00004 mg/kg body weight to about 10 g/kg body weight. According to another embodiment, the therapeutically effective amount of the HIV protease inhibitor is from about 0.00005 mg/kg body weight to about 10 g/kg body weight. According to another embodiment, the therapeutically effective amount of the HIV protease inhibitor is from about 0.00006 mg/kg body weight to about 10 g/kg body weight. According to another embodiment, the therapeutically effective amount of the HIV protease inhibitor is from about 0.00007 mg/kg body weight to about 10 g/kg body weight. According to another embodiment, the therapeutically effective amount of the HIV protease inhibitor is from about 0.00008 mg/kg body weight to about 10 g/kg body weight. According to another embodiment, the therapeutically effective amount of the HIV protease inhibitor is from about 0.00009 mg/kg body weight to about 10 g/kg body weight. According to another embodiment, the therapeutically effective amount of the HIV protease inhibitor is from about 0.0001 mg/kg body weight to about 10 g/kg body weight. According to some such embodiments, the therapeutically effective amount of the HIV protease inhibitor is about 0.0005 mg/kg body weight. According to some such embodiments, the therapeutically effective amount of the HIV protease inhibitor is about 0.001 mg/kg body weight. According to some such embodiments, the therapeutically effective amount of the HIV protease inhibitor is about 0.005 mg/kg body weight. According to some such embodiments, the therapeutically effective amount of the HIV protease inhibitor is about 0.01 mg/kg body weight. According to some such embodiment, the therapeutically effective amount is about 0.1 mg/kg body weight. According to some such embodiments, the therapeutically effective amount of the HIV protease inhibitor is about 1 mg/kg body weight. According to some such embodiments, the therapeutically effective amount of the HIV protease inhibitor is about 10 mg/kg body weight. According to some such embodiments, the therapeutically effective amount of the HIV protease inhibitor is about 20 mg/kg body weight. According to some such embodiments, the therapeutically effective amount of the HIV protease inhibitor is about 30 mg/kg body weight. According to some such embodiments, the therapeutically effective amount of the HIV protease inhibitor is about 40 mg/kg body weight. According to some such embodiments, the therapeutically effective amount of the HIV protease inhibitor is about 50 mg/kg body weight. According to some such embodiments, the therapeutically effective amount of the HIV protease inhibitor is about 60 mg/kg body weight. According to some such embodiments, the therapeutically effective amount of the HIV protease inhibitor is about 70 mg/kg body weight. According to some such embodiments, the therapeutically effective amount of the HIV protease inhibitor is about 80 mg/kg body weight. According to some such embodiments, the therapeutically effective amount of the HIV protease inhibitor is about 90 mg/kg body weight. According to some such embodiments, the therapeutically effective amount of the HIV protease inhibitor is about 100 mg/kg body weight. According to some such embodiments, the therapeutically effective amount of the HIV protease inhibitor is about 110 mg/kg body weight. According to some such embodiments, the therapeutically effective amount of the HIV protease inhibitor is about 120 mg/kg body weight. According to some such embodiments, the therapeutically effective amount of the HIV protease inhibitor is about 130 mg/kg body weight. According to some such embodiments, the therapeutically effective amount of the HIV protease inhibitor is about 140 mg/kg body weight. According to some such embodiments, the therapeutically effective amount of the HIV protease inhibitor is about 150 mg/kg body weight. According to some such embodiments, the therapeutically effective amount of the HIV protease inhibitor is about 160 mg/kg body weight. According to some such embodiments, the therapeutically effective amount of the HIV protease inhibitor is about 170 mg/kg body weight. According to some such embodiments, the therapeutically effective amount of the HIV protease inhibitor is about 180 mg/kg body weight. According to some such embodiments, the therapeutically effective amount of the HIV protease inhibitor is about 190 mg/kg body weight. According to some such embodiments, the therapeutically effective amount of the HIV protease inhibitor is about 200 mg/kg body weight. According to some such embodiments, the therapeutically effective amount of the HIV protease inhibitor is about 250 mg/kg body weight. According to some such embodiments, the therapeutically effective amount of the HIV protease inhibitor is about 500 mg/kg body weight.

The term "derivative" as used herein refers to a compound obtained from, or regarded as derived from, or produced by modification of, another and containing essential elements of the parent substance. The term "variant" as used herein refers to a compound or substance that deviates or differs from a standard. Generally, variants are slightly different from standards.

According to another embodiment, the composition is a pharmaceutical composition.

According to another embodiment, the composition further comprises at least one therapeutic agent. According to another embodiment, the additional therapeutic agent is of a therapeutically effective amount.

Methods for Synthesis of HIV Protease Inhibitors

The present disclosure further provides methods of synthesis of HIV protease inhibitor compounds according to the described invention. The compounds can be prepared using conventional organic syntheses. Abbreviations which are used in the descriptions of the schemes, preparations and the examples that follow are:

THF: Tetrahydrofuran;
DMF: N,N-Dimethylformamide;
EtOAc: Ethyl acetate;
AcOH: Acetic acid;
HOBt: 3-Hydroxy-1,2,3-benzotriazin-4(3H)-one;
EDCl: 1-(3-dimethylaminopropyl)-3-ethylcarbodiimide hydrochloride;
NMM: N-Methylmorpholine;
ADDP: 1,1'-(Azodicarbobyl)dipiperidine;
DEAD: Diethylazodicarboxylate;
MeOH: Methanol;

EtOH: Ethanol;
Et$_2$O: Diethyl ether;
Bn: Benzyl;
Boc: tert-Butyloxycarbonyl;
Cbz: Benzyloxycarbonyl;
Cp: Cylcopentyldienyl;
Ts: p-toluenesulfonyl;
Me: Methyl;
HATU: O-(7-Azabenzotriazol-1-yl)-N,N,N',N'-tetramethyluronium hexafluorophosphate;
Chg: Cyclohexylglycine;
G: Glycerol;
TG: Thioglycerol;
alloc: allyloxycarbonyl;
FMOC: 9-Fluorenyl methyloxycarbonyl;
Dde: N-1-(4,4-dimethyl-2,6-dioxocyclohex-1-ylidene) ethyl;
tBu: tert-butyl;
equiv: equivalent;
rel. int.: relative intensity;
aq: aqueous;
rt: room temperature;
satd: saturated;
Hex: hexane(s);
NBA: Nitrobenzoic acid;
PyBrOP: Tris(pyrrolidino)bromophosphonium hexafluorophosphate;
DMSO: Dimethyl sulfoxide;
TFA: Trifluoroacetic acid;
HOBt: Hydroxybezotriazole;
Hunigs base: Diisopropylethyl amine;
BOP: Benzotrizaol-1-yloxytris(dimethylamino)phosphonium hexafluorophosphate;
LDA: Lithium diisopropyl amide;
Ph$_3$P: Triphenyl phosphine;
LAH: Lithium Aluminum Hydride;
DMAP: 4-Dimethyl aminopyridine;
DCC: Dicyclohexylcarbodiimide;
MCPBA: meta-Chloroperbenzoic acid;
BINAP: 2,2'-Bis(diphenylphosphino)-1,1'-binaphtol;
MeCN: acetonitrile;
Pr: Propyl;
Ac: Acetyl;
Ph: Phenyl.

The described invention provides a method of making the HIV protease inhibitor compounds disclosed herein. The compounds may be prepared by several techniques known in the art. Representative illustrative procedures are outlined in the following reactions. It is to be understood that while the following illustrative schemes describe the preparation of protease inhibitor compounds predominantly by opening an epoxide side chain intermolecularly, other suitable substituents may be utilized to prepare protease inhibitor compounds and compounds with other biological activities. Syntheses can be carried out using reaction schemes 1, 2, 3 and 4. Scheme 1 describes a general reaction scheme for making compounds of the instant disclosure wherein the R of [Formula I] is a methyl group. Scheme 2 describes a general reaction scheme for making compounds of the instant disclosure wherein R of [Formula I] is an aromatic ring. Scheme 3 describes a general reaction scheme for making compounds of the instant disclosure wherein R$^1$ of [Formula I] is an amide group. Scheme 4 describes a general reaction scheme for making compounds of the instant disclosure wherein R$^2$ and R$^3$ of [Formula I] are substitutions on the aromatic ring.

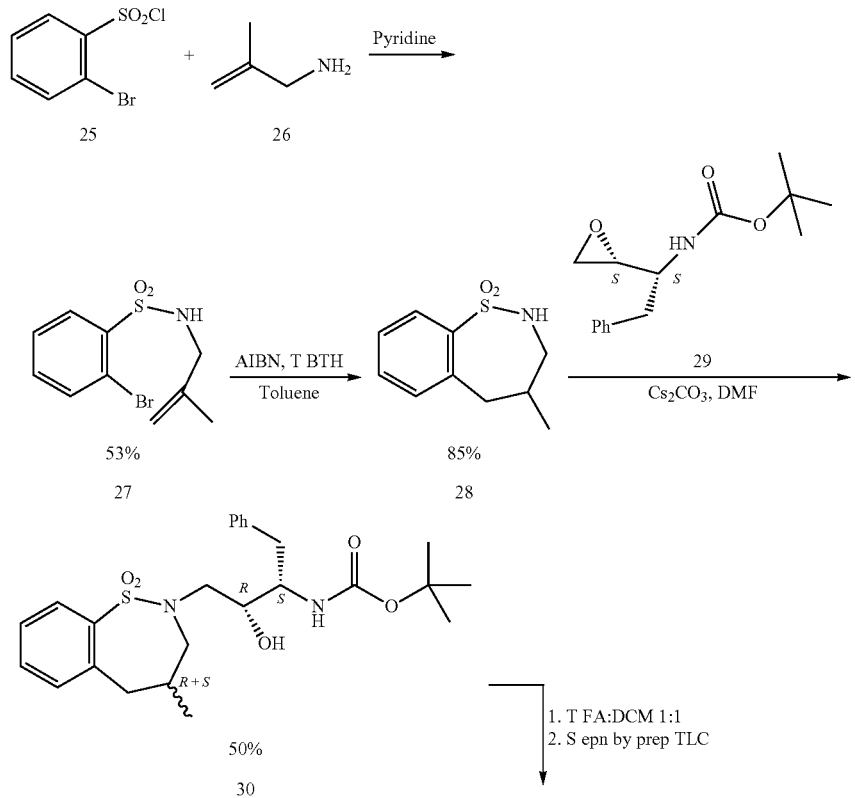

-continued

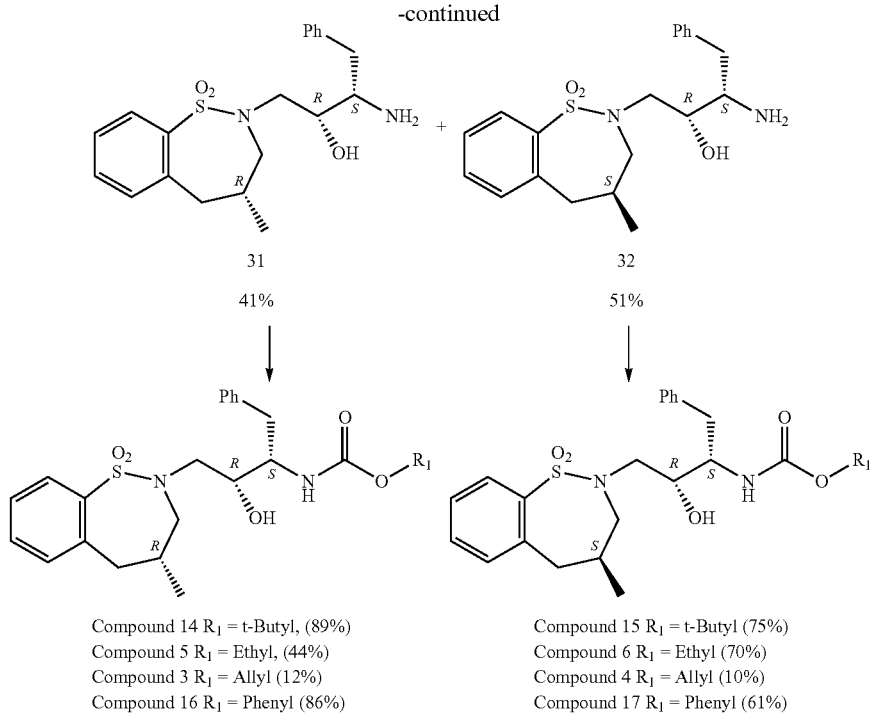

Compound 14 R₁ = t-Butyl, (89%)
Compound 5 R₁ = Ethyl, (44%)
Compound 3 R₁ = Allyl (12%)
Compound 16 R₁ = Phenyl (86%)

Compound 15 R₁ = t-Butyl (75%)
Compound 6 R₁ = Ethyl (70%)
Compound 4 R₁ = Allyl (10%)
Compound 17 R₁ = Phenyl (61%)

1.1. Scheme 1 Summary

In Scheme 1, 2-bromobenzenesulfonyl chloride (25) and 2-methyl-allylamine (26) are reacted in a pyridine solution to generate an intermediate (27) which, upon treatment with TBTH and AIBN in toluene give the radical adduct (28), which when reacted with (2S,3S)-1,2-epoxy-3-(boc-amino)-4-phenylbutane (29) in the presence of $Cs_2CO_3$ gives compound (30), as a mixture of two diastereomers. The two diastereomers are treated with TFA:DCM (1:1) and separated by preparative TLC into the diastereomer having the stereochemistry S—R—R (31) and the diastereomer having the stereochemistry S—R—S (32). The resulting diastereomers may then be converted to carbamates.

The diastereomer 32 may be converted to the carbamates 15, 6, 4 and 17 by treatment with di-tert-butyl-dicarbonate, ethyl chloroformate, allyl chloroformate and phenyl chloroformate, respectively, in the presence of di-isopropyl-N-ethylamine.

Similarly, diastereomer 31 may be converted to the carbamates 14, 5, 3 and 16 by treatment with di-tert-butyl-dicarbonate, ethyl chloroformate, allyl chloroformate and phenyl chloroformate, respectively, in the presence of di-isopropyl-N-ethylamine.

The structure and absolute stereochemistry of 31 were confirmed by X-ray crystallography. FIG. 1 shows an ORTEP diagram (40% probability ellipsoids) showing the crystallographic atom numbering scheme and solid-state conformation; small circles represent hydrogen atoms. The X-ray crystallographic data is presented in Tables 1-4.

It should be noted that the stereochemistry of all the compounds with C4 methyl substituents are rigidly established using X-ray data. The stereochemistry of compounds with C4 phenyl substituents are based on their relative polarities and biological activity. When comparing the two diastereoisomers, the more active compounds in the C4 methyl and C4 phenyl series were consistently more polar than the corresponding diastereoisomer.

Table 1 shows the crystallographic data of the samples.

TABLE 1

| Crystallographic Data | |
|---|---|
| Molecular Formula | $C_{20}H_{26}N_2O_3S$ |
| Formula Weight | 374.49 |
| Color | colorless |
| Crystal System | orthorhombic |
| Space Group | $P2_12_12_1$ |
| a(A) | 8.7817(1) |
| b(A) | 9.5441(2) |
| c(A) | 23.4720(4) |
| α(°) | 90.00 |
| β(°) | 90.00 |
| γ(°) | 90.000 |
| V(A³) | 1967.27(6) |
| Z | 4 |
| $D_{calcd.}$ (g cm⁻³) | 1.264 |
| Radiation (λ, A) | Mo-Kα (0.71073) |
| Temp. (K) | 294(2) |
| Crystal dimensions (mm) | 0.40 × 0.10 × 0.06 |
| Absorption coefficient, μ(mm⁻¹) | 0.186 |
| F(000) | 800 |
| Diffractometer | Bruker Kappa Apex II |
| Theta range for data collection | 1.74 to 27.55 |
| Index ranges | −11 < h, 0, 12 < k < 12, −30 < l < 30 |
| Reflections collected | 37118 |
| Independent reflections | 4513 [R(int) = 0.0625] |
| Observed reflections [I > 2sigma(I)] | 3182 |
| Completeness to theta = 27.55 | 99.2% |
| Absorption correction | SADBS 2.10 (Sheldrick, 2004) |
| Max. and min. transmission | 0.9889 and 0.9293 |
| Solution method | SHELXS-97 (Sheldrick, 1990) |
| Refinement method | SHELXL-97 (Sheldrick, 1997) |
| Data/restraints/parameters | 4513/0/248 |
| Absolute structure parameter (Flack) | 0.995 |
| Final R indices [I > 2sigma(I)] | R1 = 0.0421, wR2 = 0.1048 |
| R indices (all data) | R1 = 0.0765, wR2 = 0.1304 |
| Largest diff. peak and hole | 0.22 and −0.26 e.A⁻³ |

Table 2 shows the Fractional Atomic Coordinates and Thermal Parameters.

TABLE 2

Fractional Atomic Coordinates and Thermal Parameters

| Atom | x | y | z | Ueq or Usio(A$^2$) |
|---|---|---|---|---|
| N1 | 0.4209(2) | 0.6098(2) | 0.09853(8) | 0.0397(5) |
| C2 | 0.3712(3) | 0.4704(3) | 0.11795(11) | 0.0494(7) |
| C3 | 0.4898(4) | 0.3842(3) | 0.14926(11) | 0.0544(7) |
| C4 | 0.5361(4) | 0.4470(3) | 0.20704(11)1 | 0.0620(8) |
| C5 | 0.6521(3) | 0.5640(3) | 0.20475(10) | 0.0527(7) |
| C6 | 0.7939(4) | 0.5447(4) | 0.22869(13) | 0.0733(10) |
| C7 | 0.9061(4) | 0.6446(5) | 0.22628(15) | 0.0870(12) |
| C8 | 0.8787(4) | 0.7701(5) | 0.20027(14) | 0.0804(11) |
| C9 | 0.7367(3) | 0.7952(4) | 0.17637(12) | 0.0628(8) |
| C10 | 0.6259(3) | 0.6930(3) | 0.17913(10) | 0.0470(6) |
| S11 | 0.44789(8) | 0.72943(7) | 0.41653(3) | 0.0500(2) |
| O12 | 0.4606(3) | 0.8617(2) | 0.11845(10) | 0.0719(6) |
| O13 | 0.3308(2) | 0.7119(3) | 0.18808(8) | 0.0728(7) |
| C14 | 0.5196(3) | 0.6134(3) | 0.04783(10) | 0.0393(5) |
| C15 | 0.4263(3) | 0.5928(2) | −0.00608(9) | 0.0370(5) |
| O16 | 03238(2) | 0.7053(2) | −0.01457(8) | 0.0520(5) |
| C17 | 0.5211(3) | 0.5843(3) | −0.05993(10) | 0.0391(5) |
| C18 | 0.6384(3) | 0.4667(3) | −0.06153(12) | 0.0463(6) |
| C19 | 0.5739(3) | 0.3217(3) | −0.05682(13) | 0.0532(7) |
| C20 | 0.4899(4) | 0.2649(4) | −0.10041(19) | 0.0904(12) |
| C21 | 0.4301(6) | 0.1294(7) | −0.0955(4) | 0.145(3) |
| C22 | 0.4567(8) | 0.0557(6) | −0.0468(5) | 0.180(5) |
| C23 | 0.5399(6) | 0.1074(4) | −0.0034(3) | 0.128(2) |
| C24 | 0.5993(4) | 0.2412(4) | −0.00868(18) | 0.0786(10) |
| N25 | 0.6004(3) | 0.7178(3) | −0.06839(10) | 0.0475(5) |
| C26 | 0.4262(5) | 0.2364(3) | 0.15780(16) | 0.0897(12) |
| H2A | 0.3374 | 0.4175 | 0.0850 | 0.059 |
| H2B | 0.2840 | 0.4823 | 0.1428 | 0.059 |
| H3 | 0.5808 | 0.3778 | 0.1253 | 0.065 |
| H4A | 0.4452 | 0.4822 | 0.2257 | 0.074 |
| H4B | 0.5767 | 0.3724 | 0.2306 | 0.074 |
| H6 | 0.8143 | 0.4606 | 0.2472 | 0.088 |
| H7 | 1.0009 | 0.6268 | 0.2424 | 0.104 |
| H8 | 0.9544 | 0.8381 | 0.1986 | 0.096 |
| H9 | 0.7165 | 0.8803 | 0.1586 | 0.075 |
| H14A | 0.5957 | 0.5401 | 0.0506 | 0.047 |
| H14B | 0.5720 | 0.7028 | 0.0461 | 0.047 |
| H15 | 0.3675 | 0.5060 | −0.0023 | 0.044 |
| H16 | 0.273(3) | 0.714(3) | 0.0146(12) | 0.047(8) |
| H17 | 0.4514 | 0.5709 | −0.0921 | 0.047 |
| H18A | 0.6949 | 0.4734 | −0.0969 | 0.056 |
| H18B | 0.7100 | 0.4807 | −0.0306 | 0.056 |
| H20 | 0.4727 | 0.3166 | −0.1334 | 0.108 |
| H21 | 0.3733 | 0.0905 | −0.1249 | 0.174 |
| H22 | 0.4158 | −0.0338 | −0.0434 | 0.216 |
| H23 | 0.5570 | 0.0546 | 0.0293 | 0.153 |
| H24 | 0.6576 | 0.2778 | 0.0208 | 0.094 |
| H25A | 0.643(4) | 0.710(3) | −0.1022(14) | 0.062(9) |
| H25B | 0.538(4) | 0.783(3) | −0.0709(13) | 0.066(10) |
| H26A | 03340 | 0.2412 | 0.1797 | 0.135 |
| H26B | 0.4997 | 0.1802 | 0.1777 | 0.135 |
| H26C | 0.4051 | 0.1950 | 0.1214 | 0.135 |

Table 3 shows anisotropic temperature factor parameters in the form: $\exp[-2\pi^2(U_{11}h^2a^{*2}+U_{22}k^2b^{*2}+U_{33}l^2*c^2+2U_{12}hka*b*+2U_{13}hla*c*+2U_{23}klb*c*)$.

TABLE 3

Anisotropic Temperature Factor Parameters

| Atom | U$_{11}$ | U$_{22}$ | U$_{33}$ | U$_{23}$ | U$_{13}$ | U$_{12}$ |
|---|---|---|---|---|---|---|
| N1 | 0.0412(11) | 0.0460(11) | 0.0320(10) | −0.0011(8) | −0.0033(9) | −0.0036(9) |
| C2 | 0.0487(14) | 0.0616(18) | 0.0380(13) | 0.0043(12) | −0.0023(11) | −0.0199(13) |
| C3 | 0.0691(17) | 0.0509(15) | 0.0432(14) | 0.0099(12) | −0.0056(14) | −0.0143(13) |
| C4 | 0.077(2) | 0.0715(19) | 0.0378(13) | 0.0148(13) | −0.0114(14) | −0.0137(17) |
| C5 | 0.0546(15) | 0.0727(19) | 0.0310(12) | −0.0011(13) | −0.0111(11) | −0.0027(14) |
| C6 | 0.070(2) | 0.099(3) | 0.0515(18) | 0.0012(18) | −0.0224(15) | 0.0083(19) |
| C7 | 0.053(3) | 0.145(4) | 0.064(2) | −0.012(2) | −0.0225(16) | 0.000(2) |
| C8 | 0.0602(18) | 0.126(3) | 0.0550(18) | −0.003(2) | −0.0092(15) | −0.036(2) |
| C9 | 0.0660(18) | 0.079(2) | 0.0434(15) | −0.0052(15) | −0.0074(13) | −0.0208(17) |
| C10 | 0.0446(13) | 0.0652(18) | 0.0312(12) | −0.0057(12) | −0.0038(10) | −0.0066(13) |
| S11 | 0.0487(3) | 0.0570(4) | 0.0443(3) | −0.0126(3) | −0.0096(3) | 0.0038(3) |
| O12 | 0.0924(15) | 0.0455(11) | 0.0779(14) | −0.0069(10) | −0.0302(13) | 0.0063(12) |
| O13 | 0.0529(12) | 0.1094(19) | 0.0561(12) | −0.0303(13) | 0.0034(9) | 0.0033(12) |
| C14 | 0.0380(12) | 0.0433(14) | 0.0365(12) | 0.0051(10) | −0.0032(10) | −0.0027(10) |
| C15 | 0.0358(12) | 0.0389(12) | 0.0363(11) | 0.0013(9) | −0.0044(10) | 0.0034(10) |
| O16 | 0.0488(10) | 0.0673(13) | 0.0398(10) | 0.0088(9) | 0.0023(8) | 0.0213(9) |
| C17 | 0.0373(12) | 0.0450(14) | 0.0349(11) | 0.0006(10) | −0.0031(9) | −0.0015(10) |
| C18 | 0.0415(13) | 0.0470(15) | 0.0503(15) | −0.0044(12) | 0.0045(11) | 0.0012(11) |
| C19 | 0.0456(14) | 0.0471(15) | 0.0669(17) | −0.0181(13) | 0.0124(14) | 0.0030(12) |
| C20 | 0.0643(19) | 0.094(3) | 0.113(3) | −0.057(2) | 0.002(2) | −0.0048(19) |
| C21 | 0.067(3) | 0.120(5) | 0.248(8) | −0.121(5) | 0.026(4) | −0.023(4) |
| C22 | 0.092(4) | 0.064(4) | 0384(15) | −0.084(5) | 0.124(7) | −0.020(3) |
| C23 | 0.108(4) | 0.053(2) | 0.222(7) | 0.028(3) | 0.098(4) | 0.020(3) |
| C24 | 0.077(2) | 0.0502(18) | 0.109(3) | 0.0110(19) | 0.032(2) | 0.0147(16) |
| N25 | 0.0483(13) | 0.0467(13) | 0.0475(13) | 0.0090(11) | 0.0039(10) | 0.0007(11) |
| C26 | 0.125(3) | 0.0599(19) | 0.084(2) | 0.0247(18) | −0.021(2) | −0.027(2) |

Table 4 shows interatomic distances (Å) and angles (degree).

TABLE 4

Interatomic distances (Å) and angles (degree)

(a) Bond lengths

| | | | |
|---|---|---|---|
| N1—C2 | 1.473(3) | S11—O12 | 1.429(2) |
| N1—S11 | 1.621(2) | S11—O13 | 1.427(2) |
| N1—C14 | 1.472(3) | C14—C15 | 1.520(3) |
| C2—C3 | 1.517(4) | C15—O16 | 1.415(3) |
| C3—C4 | 1.537(4) | C15—C17 | 1.516(3) |
| C3—C26 | 1.531(4) | C17—C18 | 1.525(4) |
| C4—C5 | 1.513(4) | C17—N25 | 1.465(3) |
| C5—C6 | 1.378(4) | C18—C19 | 1.499(4) |
| C5—C10 | 1.389(4) | C19—C20 | 1.373(5) |
| C6—C7 | 1.372(5) | C19—C24 | 1.385(5) |
| C7—C8 | 1366(6) | C20—C21 | 1.401(7) |
| C8—C9 | 1.388(5) | C21—C22 | 1.361(11) |
| C9—C10 | 1.380(4) | C22—C23 | 1.348(11) |
| C10—C11 | 1.775(3) | C23—C24 | 1.385(6) |
| C2—H2A | 0.97 | C17—H17 | 0.98 |
| C2—H2B | 0.97 | C18—H18A | 0.97 |
| C3—H3 | 0.98 | C18—H18B | 0.97 |
| C4—H4A | 0.97 | C20—H20 | 0.93 |
| C4—H4B | 0.97 | C21—H21 | 0.93 |
| C6—H6 | 0.93 | C22—H22 | 0.93 |
| C7—H7 | 0.93 | C23—H23 | 0.93 |
| C8—H8 | 0.93 | C24—H24 | 0.93 |
| C9—H9 | 0.93 | N25—H25A | 0.88(3) |
| C14—H14A | 0.97 | N25—H25B | 0.83(3) |
| C14—H14B | 0.97 | C26—H26A | 0.96 |
| C15—H15 | 0.98 | C26—H26B | 0.96 |
| O16—H16 | 0.82(3) | C26—H26C | 0.96 |

(b) Bond Angles

| | | | |
|---|---|---|---|
| C2—N1—S11 | 117.7(2) | NI—S11-O13 | 106.7(1) |
| C2—N1—C14 | 116.5(2) | C10—S11-O12 | 107.7(1) |
| S11—N1—C14 | 117.4(2) | C10—S11-O13 | 108.5(1) |
| N1—C2—C3 | 115.9(2) | O12—S11-O13 | 118.4(2) |
| C2—C3—C4 | 113.4(2) | N1—C14—C15 | 110.7(2) |
| C2—C3—C26 | 108.2(3) | C14—C15-O16 | 111.2(2) |
| C4—C3—C26 | 109.9(2) | C14—C15—C17 | 113.9(2) |
| C3—C4—C5 | 115.8(2) | O16—C15—C17 | 105.8(2) |
| C4—C5—C6 | 119.7(3) | C15—C17—C18 | 115.5(2) |
| C4—C5—C10 | 123.9(2) | C15—C17—N25 | 109.1(2) |
| C6—C5—C10 | 116.4(3) | C18—C17—N25 | 108.4(2) |
| C5—C6—C7 | 122.6(3) | C17—C18—C19 | 115.0(2) |
| C6—C7—C8 | 120.1(3) | C18—C19—C20 | 120.8(3) |
| C7—C8—C9 | 119.4(3) | C18—C19—C24 | 120.8(3) |
| C8—C9—C10 | 119.5(3) | C20—C19—C24 | 118.4(3) |
| C5—C10—C9 | 122.0(3) | C19—C20—C21 | 120.3(5) |
| C5—C10—S11 | 120.4(2) | C20—C21—C22 | 118.8(7) |
| C9—C10—S11 | 117.6(2) | C21—C22—C23 | 122.5(6) |
| N1—S11—C10 | 106.9(1) | C22—C23—C24 | 118.3(6) |
| N1—S11—O12 | 108.2(1) | C19—C24—C23 | 121.6(5) |
| N1—C2—H2A | 108.3 | C15—O16—816 | 108(2) |
| N1—C2—H2B | 108.3 | C15—C17—H17 | 107.8 |
| C3—C2—H2A | 108.3 | C18—C17—H17 | 107.8 |
| C3—C2—H2B | 108.3 | N25—C17—H17 | 107.8 |
| H2A—C2—H2B | 107.4 | C17—C18—H18A | 108.5 |
| C2—C3—H3 | 108.4 | C17—C18—H18B | 108.5 |
| C4—C3—H3 | 108.4 | C19—C18—H18A | 108.5 |
| C26—C3—H3 | 108.4 | C19—C18—H1813 | 108.5 |
| C3—C4—H4A | 108.3 | H18A—C18—H18B | 107.5 |
| C3—C4—H4B | 108.3 | C19—C20—H20 | 119.8 |
| C5—C4—H4A | 108.3 | C21—C20—H20 | 119.8 |
| C5—C4—H4B | 108.3 | C20—C21—H21 | 120.6 |
| H4A—C4—H4B | 107.4 | C22—C21—H21 | 120.6 |
| C5—C6—H6 | 118.7 | C21—C22—H22 | 118.7 |
| C7—C6—H6 | 118.7 | C23—C22—H22 | 118.7 |
| C6—C7—H7 | 120.0 | C22—C23—H23 | 120.9 |
| C8C7—H7 | 120.0 | C24—C23—H23 | 120.9 |
| C7—C8—H8 | 120.3 | C19—C24—H24 | 119.2 |
| C9—C8—H8 | 120.3 | C23—C24—H24 | 119.2 |
| C8—C9—H9 | 120.2 | C17—N25—H25A | 105(2) |
| C10—C9—H9 | 120.2 | C17—N25—H25B | 110(2) |
| N1—C14—H14A | 109.5 | H25A—N25—H25B | 106(3) |
| N1—C14—H14B | 109.5 | C3—C26—H26A | 109.5 |
| C15—C14—H14A | 109.5 | C3—C26—H26B | 109.5 |
| C15—C14—H14B | 109.5 | C3—C26—H26C | 109.5 |
| H14A—C14—H14B | 108.1 | H26A—C26—H26B | 109.5 |
| C14—C15—H15 | 108.6 | H26A—C26—H26B | 109.5 |
| O16—C15—H15 | 108.6 | H26A—C26—H26B | 109.5 |
| C17—C15—H15 | 108.6 | | |

(c) Torsion Angles

| | | | |
|---|---|---|---|
| S11—N1—C2—C3 | −71.1(3) | C8—C9—C10—S11 | −178.7(2) |
| C14—N1—C2—C3 | 76.1(3) | C5—C10—S11—N1 | −57.3(2) |
| C2—N1—S11—C10 | 77.4(2) | C5—C10—S11—C12 | −173.4(2) |
| C2—N1—S11—C12 | −166.8(2) | C5—C10—S11-O13 | 57.4(3) |
| C2—N1—S11—C13 | −38.5(2) | C9—C10—S11—N1 | 120.8(2) |
| C14—N1—S11—C10 | −69.5(3) | C9—C10—S11-O12 | 4.7(3) |
| C14—N1—S11—C12 | 46.3(2) | C9—C10—S11-O13 | −124.5(2) |
| C14—N1—S11—C13 | 174.3(2) | N1—C14—C15—C16 | 64.9(3) |
| C2—N1—C14—C15 | 77.8(2) | N1—C14—C15—C17 | −175.7(2) |
| S11—N1—C14—C15 | −134.9(2) | C14—C15—C17—C18 | 59.2(3) |
| N1—C2—C3—C4 | 66.3(3) | C14—C15—C17—N25 | −63.2(3) |
| N1—C2—C3—C26 | −171.4(3) | C16—C15—C17—C18 | −178.4(2) |
| C2—C3—C4—C5 | −81.1(3) | C16—C15—C17—N25 | 59.2(2) |
| C26—C3—C4—C5 | 157.6(3) | C15—C17—C18—C19 | 60.6(3) |
| C3—C4—C5—C6 | −115.0(3) | N25—C17—C18—C19 | −176.6(2) |
| C3—C4—C5—C10 | 64.4(4) | C17—C18—C19—C20 | 69.7(3) |
| C4—C5—C6—C7 | 177.6(3) | C17—C18—C19—C24 | −111.2(3) |
| C10—C5—C6—C7 | −1.9(5) | C18—C19—C20—C21 | −179.9(3) |
| C4—C5—C10—C9 | −177.8(3) | C24—C19—C20—C21 | 0.9(5) |
| C4—C5—C10—S11 | 0.2(4) | C18—C19—C24—C23 | 179.6(3) |
| C6—C5—C10—C9 | 1.6(4) | C20—C19—C24—C23 | −1.2(5) |
| C6—C5—C10—S11 | 179.6(2) | C19—C20—C21—C22 | 0.1(8) |
| C5—C6—C7—C8 | 1.2(6) | C20—C21—C22—C23 | −0.8(10) |
| C6—C7—C8—C9 | −0.1(5) | C21—C22—C23—C24 | 0.5(9) |
| C7—C8—C9—C10 | −0.2(5) | C22—C23—C24—C19 | 0.6(6) |
| C8—C9—C10-O5 | −0.6(4) | | |

(d) Hydrogen-bonded Distances (Donor . . . Acceptor)

| | | | |
|---|---|---|---|
| O16 . . . N25[I] | 2.860(3) | N25 . . . O16 | 2.741(3) |

Roman numeral superscript refers to the following transformations of the fractional atomic coordinates listed in Table 2. −1/2 + x, 3/2 − y. − z Repeating the above synthesis in Scheme 1 and using allylamine in place of methylallylamine, compound 1 was obtained as a single entity as it lacks substitution at C4. Compound 1 was much less active when compared to Compound 4.

1.2 Synthesis Protocols

Compound 27

To a solution of 2-methylallylamine (500 mg, 7.03 mmol) in pyridine (5 mL) was added 2-bromobenzenesulfonyl chloride (1.63 g, 6.39 mmol) dissolved in pyridine (5 mL). The reaction was stirred at room temperature for 8-10 hours under nitrogen. TLC (Thin Layer Chromatography) was monitored to check the progress of the reaction. After the reaction was complete, the reaction mixture was neutralized with 30% HCl (100 mL) and then extracted with dichloromethane (DCM) (4×30 mL). The combined organic layers were dried over anhydrous sodium sulfate and evaporated to dryness to yield the crude compound. The crude compound was purified by column chromatography using 15% ethyl acetate in hexane to yield the pure compound 27 (1.08 g, 53%).

Compound 28

Compound 27 (1.0 g, 3.45 mmol) was dissolved in toluene (15 mL) and to it was added azobisisobutyronitrile (AIBN) (113 mg, 0.689 mmol). The above solution was heated to about 60-70° C. and then tributyltin hydride (TBTH) (1.1 g, 3.79 mmol) was added slowly under nitrogen. After the addition was complete, the reaction mixture was refluxed for 4-6 hours. TLC was checked. After the reaction was complete, the reaction mixture was evaporated to dryness. The residue was washed with water (20 mL) and extracted with DCM (3×50 mL). The organic layers were combined, dried over sodium sulfate, and concentrated to yield the crude compound. The crude compound was purified by column chromatography using 25% ethyl acetate in hexane to yield to compound 28 (620 mg, 85%) as white crystals.

Compound 30

To a solution of compound 28 (187 mg, 0.71 mmol) in dimethylformamide (DMF) (3 mL) was added (2S,3S)-1,2-epoxy-3-(bocamino)-4-phenylbutane (150 mg, 0.71 mmol) (compound 29), followed by the addition of cesium carbonate (462 mg, 1.42 mmol). The reaction was stirred for 10-12 hours at room temperature under nitrogen. TLC was monitored. The reaction mixture was filtered through cotton to remove excess cesium carbonate. Water (15 mL) was added to the reaction mixture and then it was extracted using ethyl acetate (3×15 mL). The combined organic layers were dried over anhydrous sodium sulfate and concentrated to yield the crude compound. The crude compound was purified by column chromatography using 25% ethyl acetate in hexane to yield compound 30 (170 mg, 50%) as an oil.

Compound 31 and 32

Compound 30 (125 mg, 0.263 mmol) was taken in 1:1 mixture of DCM and TFA (1.5 mL:1.5 mL) and stirred at room temperature under nitrogen for 3-4 hours. After the reaction was complete, the reaction mixture was basified with sodium hydroxide solution (50%) and extracted with ethyl acetate (4×25 mL). The combined organic layers were dried with anhydrous sodium sulfate and evaporated to yield the crude compound. Compounds 31 (40 mg, 41%) and 32 (50 mg, 51%) were separated by preparatory TLC (6% methanol in chloroform). Compounds 31 and 32 were recrystallized from DCM/hexane.

Compounds 14 and 15

Compound 31 (16 mg, 0.042 mmol) was dissolved in THF (1 mL) and cooled on ice. Diisopropylethylamine (DIPEA) (5.5 mg, 0.042 mmol) was added to the reaction mixture followed by the addition of di-tert-butyl dicarbonate (9.33 mg, 0.042 mmol) in THF (1 mL). The reaction mixture was slowly allowed to reach room temperature and stirred for 10-12 hours under nitrogen. When the reaction was complete, the reaction mixture was diluted with water (10 mL) and washed with chloroform (3×15 mL). The combined organic layers were dried over anhydrous sodium sulfate and evaporated to yield the crude compound. The crude compound was purified by column chromatography using 25% ethyl acetate in hexane to yield Compound 14 (18 mg, 89%).

Compound 32 (22 mg, 0.059 mmol) was dissolved in THF (1 mL) and cooled on ice. DIPEA (7.6 mg, 0.059 mmol) was added to the reaction mixture followed by the addition of di-tert-butyl dicarbonate (12.8 mg, 0.059 mmol) in THF (1 mL). The reaction mixture was slowly allowed to reach room temperature and stirred for 10-12 hours under nitrogen. When the reaction was complete, the reaction mixture was diluted with water (10 mL) and extracted with chloroform (3×15 mL). The combined organic layers were dried over anhydrous sodium sulfate and evaporated to yield the crude compound. The crude compound was purified by column chromatography using 25% ethyl acetate in hexane to yield Compound 15 (21 mg, 75%).

Compound 5 and 6

Compound 31 (29 mg, 0.077 mmol) was dissolved in THF (1 mL) and cooled on ice. DIPEA (10 mg, 0.077 mmol) was added to the reaction mixture followed by the addition of ethyl chloroformate (8.4 mg, 0.077 mmol) in THF (1 mL). The reaction mixture was slowly allowed to reach room temperature and stirred for 10-12 hours under nitrogen. The progress of the reaction was monitored by TLC. The reaction mixture was diluted with water (10 mL) and extracted with chloroform (3×15 mL). The combined organic layers were dried over anhydrous sodium sulfate and evaporated to yield the crude compound. The crude compound was purified by column chromatography using 3% methanol in chloroform to yield Compound 5 (15 mg, 44%).

Compound 32 (48 mg, 0.128 mmol) was dissolved in THF (1 mL) and cooled on ice. DIPEA (16.5 mg, 0.128 mmol) was added to the reaction mixture followed by the addition of ethyl chloroformate (13.9 mg, 0.128 mmol) in THF (1 mL). The reaction mixture was slowly allowed to reach room temperature and stirred for 10-12 hours under nitrogen. The progress of the reaction was monitored by TLC. When the reaction was complete, the reaction mixture was diluted with water (10 mL) and washed with chloroform (3×15 mL). The combined organic layers were dried over anhydrous sodium sulfate and evaporated to yield the crude compound. The crude compound was purified by column chromatography using 3% methanol in chloroform to yield Compound 6 (40 mg, 70%).

Compounds 3 and 4

Compound 30 (125 mg, 0.263 mmol) was taken in a 1:1 mixture of DCM and TFA (1.5 mL:1.5 mL) and stirred at room temperature under nitrogen for 3-4 hours. TLC was checked to monitor the progress of the reaction. After the reaction was complete, the reaction mixture was basified with sodium hydroxide solution (50%) and extracted with ethyl acetate (4×25 mL) and DCM (3×20 mL). The combined organic layers were dried with anhydrous sodium sulfate and evaporated to dry to yield a mixture of diastereomers (Compounds 31 and 32). The mixture of Compounds 31 and 32 was dissolved in THF (2 mL) and cooled on ice. DIPEA (34 mg, 0.263 mmol) was added to the reaction mixture followed by the addition of allyl chloroformate (32 mg, 0.263 mmol) in THF (1 mL). The reaction mixture was slowly allowed to reach room temperature and stirred for 10-12 hours under nitrogen. The progress of the reaction was monitored by TLC. When the reaction was complete, the reaction mixture was diluted with water (10 mL) and extracted with DCM (4×20 mL). The combined organic layers were dried over anhydrous sodium sulfate and evaporated to yield the crude compound. Compounds 3 (15 mg, 12%) and 4 (12 mg, 10%) were separated by preparatory TLC (3% ethyl acetate in chloroform).

Compounds 16 and 17

Compound 31 (22 mg, 0.059 mmol) was dissolved in THF (1 mL) and cooled on ice. DIPEA (7.6 mg, 0.059 mmol) was added to the reaction mixture followed by the addition of phenyl chloroformate (9.21 mg, 0.059 mmol) in THF (1 mL). The reaction mixture was slowly allowed to reach room temperature and stirred for 10-12 hours under nitrogen. The progress of the reaction was monitored by TLC. When the reaction was complete, the reaction mixture was diluted with water (10 mL) and extracted with chloroform (3×15 mL). The combined organic layers were dried over anhydrous sodium sulfate and evaporated to yield the crude compound. The crude compound was purified by column chromatography using 25% ethyl acetate in hexane to yield Compound 16 (25 mg, 86%). Compound 32 (15 mg, 0.040 mmol) was dissolved in THF (1 mL) and cooled on ice. DIPEA (5.18 mg, 0.040 mmol) was added to the reaction mixture followed by the addition of phenyl chloroformate (6.3 mg, 0.040 mmol) in THF (1 mL). The reaction mixture was slowly allowed to reach room temperature and stirred for 10-12 hours under nitrogen. The progress of the reaction was monitored by TLC. When the reaction was complete, the reaction mixture was diluted with water (10 mL) and extracted with chloroform (3×15 mL). The combined organic layers were dried over anhydrous sodium sulfate and evaporated to yield the crude compound. The crude compound was purified by column chromatography using 25% ethyl acetate in hexane to yield Compound 17 (12 mg, 61%).

2.1. Scheme 2 Summary

In Scheme 2, 2-bromobenzenesulfonyl chloride (25) and 2-phenyl allyl amine (33) are reacted in the presence of pyridine to generate intermediate (34) which, upon treatment with TBTH and AIBN in toluene gives the radical derived adduct (35) which, when reacted with (2S,3S)-1,2-epoxy-3-(boc-amino)-4-phenylbutane (29) in the presence of $Cs_2CO_3$ gives compound (36), as mixture of two diastereomers. The mixture of two diastereomers is treated with TFA:DCM (1:1) to produce compound (37) as a mixture of diastereomers. Treatment of (37) with substituted chloroformates for example ethyl chloroformate in the presence of di-isopropyl-N-ethylamine yielded a mixture of diastereomers which could be separated into pure diastereomers (10) and (11) using preparative TLC. Similarly, compound (37) on treatment with allyl chloroformate in the presence of di-isopropyl-N-ethylamine yielded a mixture of diastereomers which could be separated by preparative TLC into pure diastereomers (8) and (9).

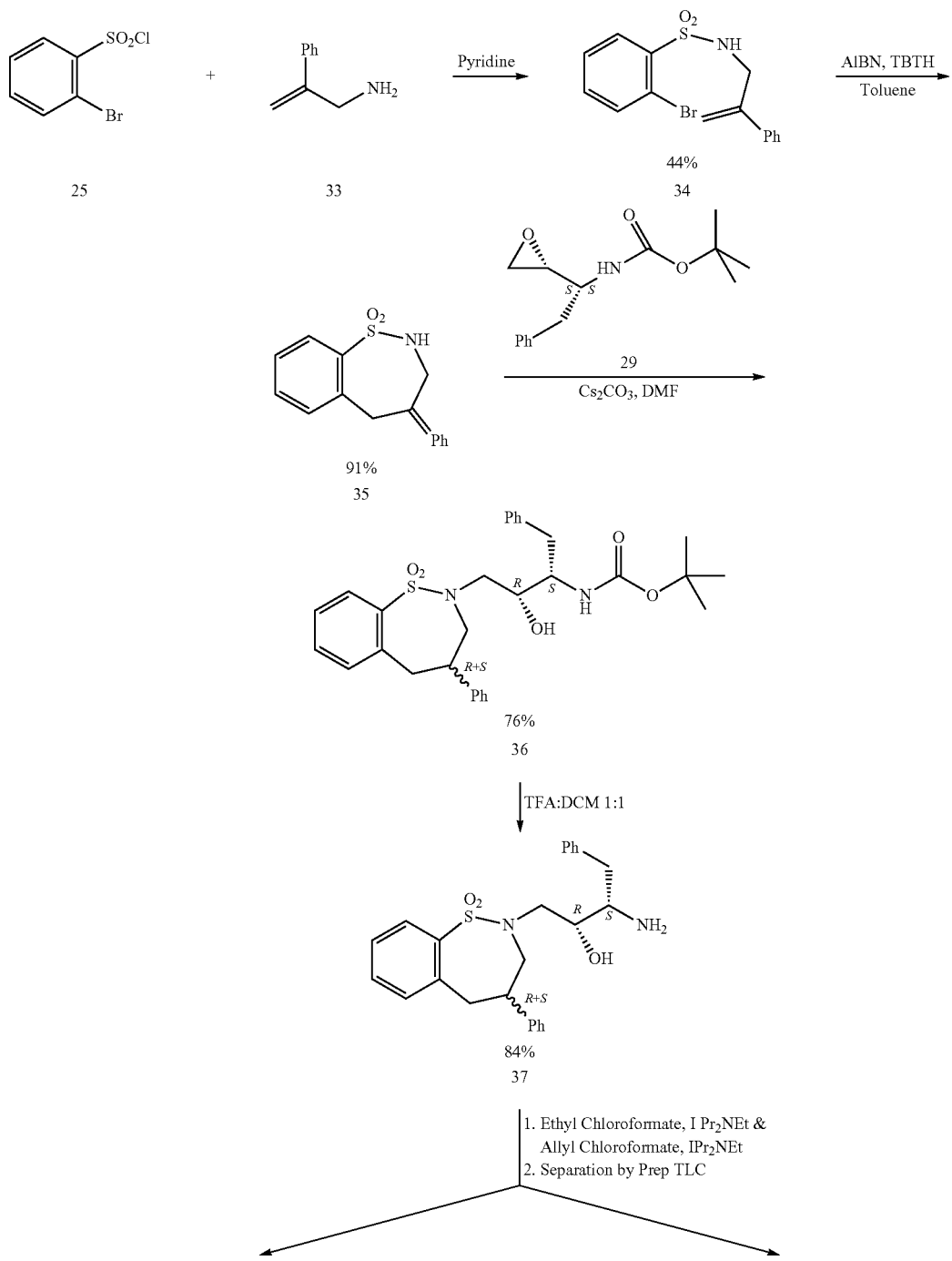

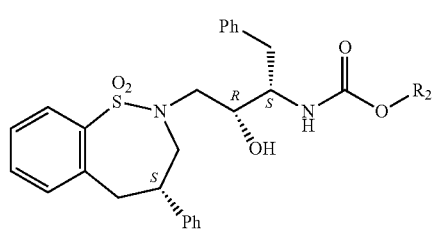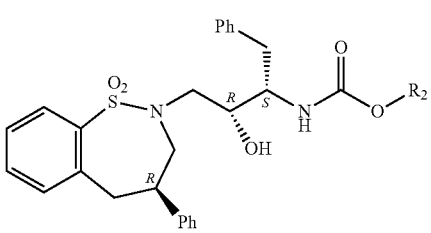

Compound 10 R$_2$ = Ethyl (32.1%)
Compound 8 R$_2$ = Allyl (16.7%)

Compound 11 R$_2$ = Ethyl (45%)
Compound 9 R$_2$ = Allyl (20.9%)

2.2. Synthesis Protocols

Compound 34

To a solution of 2-phenyl allylamine (600 mg, 4.5 mmol) (33) in DCM (15 mL) was added, pyridine (0.78 mL, 9.9 mmol) followed by 2-bromo benzene sulfonyl chloride (1.14 g, 4.5 mmol)(25). The reaction was stirred at room temperature for 8-10 hours under nitrogen. TLC was monitored to check the progress of the reaction. After the reaction was complete, the reaction mixture was diluted with DCM (60 mL) and washed with 1% HCl solution. The organic layer was dried over anhydrous sodium sulfate and evaporated to dryness to yield the crude compound. The crude compound was purified by column chromatography using 10% ethyl acetate in hexane to yield the crystalline compound 32 (700 mg, 44%). Recrystallization of compound 34 in DCM and hexane produced white crystals.

Compound 35

Compound 34 (100 mg, 0.28 mmol) was dissolved in toluene (10 mL) and to it was added azobisisobutyronitrile (AIBN) (9.32 mg, 0.05 mmol). The above solution was heated to about 60-70° C. and then tributyltin hydride (TBTH) (0.1 mL, 0.31 mmol) was added slowly under nitrogen. After the addition was complete, the reaction mixture was refluxed for 4-6 hours. TLC was checked to monitor the progress of the reaction. The reaction mixture was evaporated to dryness, the residue was washed with water (20 mL) and extracted with DCM (3×50 mL). The organic layers were combined, dried over sodium sulfate, and concentrated to yield the crude compound. The crude compound was purified by column chromatography using 15% ethyl acetate in hexane to yield white solid, compound 35 (70 mg, 91%)

Compound 36

To a solution of compound 35 (100 mg, 0.36 mmol) in dimethylformamide (DMF) (3 mL) was added (2S,3S)-1,2-epoxy-3-(bocamino)-4-phenylbutane (96.3 mg, 0.36 mmol) (29), followed by the addition of cesium carbonate (238 mg, 0.73 mmol). The reaction was stirred for 10-12 hours at room temperature under nitrogen. TLC was checked. The reaction mixture was filtered through cotton to remove excess cesium carbonate. Water (15 mL) was added to the reaction mixture and then it was extracted using ethyl acetate (3×15 mL). The combined organic layers were dried over anhydrous sodium sulfate and concentrated. The crude compound was purified by column chromatography using 25% ethyl acetate in hexane to yield compound 36 (150 mg, 76%) as mixture of diastereoisomers.

Compound 37

Compound 36 (125 mg, 0.23 mmol) was taken in a 1:1 mixture of DCM and TFA (1.5 mL:1.5 mL) and stirred at room temperature under nitrogen for 3-4 hours. After the reaction was complete, the reaction mixture was basified with sodium hydroxide solution (50%) and extracted with ethyl acetate (4×25 mL). The combined organic layers were dried over anhydrous sodium sulfate and concentrated to yield Compound 37 as mixture of diastereoisomers.

Compounds 8 and 9

Compound 37 (40 mg, 0.09 mmol) was dissolved in THF (2 mL) and cooled on ice. DIPEA (0.015 mL, 0.09 mmol) was added to the reaction mixture followed by the addition of allyl chloroformate (0.0097 mL, 0.09 mmol) in THF (1 mL). The reaction mixture was slowly allowed to reach room temperature and stirred for 10-12 hours under nitrogen. The progress of the reaction was monitored by TLC. The reaction mixture was then diluted with water (10 mL) and extracted with DCM (4×20 mL). The organic layers were dried over anhydrous sodium sulfate and evaporated to yield the crude compound. The crude product was purified by column chromatography to yield mixture of separable diastereoisomers. Compound 8 (8 mg, 17%) and Compound 9 (10 mg, 21%) were separated by preparatory TLC method using 25% ethyl acetate in Hexane.

Compounds 10 and 11

Compound 37 (40 mg, 0.09 mmol) was dissolved in THF (2 mL) and cooled on ice. DIPEA (0.015 mL, 0.09 mmol) was added to the reaction mixture followed by the addition of ethyl chloroformate (0.008 mL, 0.09 mmol) in THF (1 mL). The reaction mixture was slowly allowed to reach room temperature and stirred for 10-12 hours under nitrogen. TLC was checked. The reaction mixture was then diluted with water (10 mL) and extracted with DCM (4×20 mL). The organic layers were combined, dried over anhydrous sodium sulfate and evaporated to yield the crude compound. The crude product was purified by column chromatography to yield mixture of separable diastereoisomers. Compound 10 (15 mg, 32%) and Compound 11 (21 mg, 45%) were separated by preparatory TLC method using 25% ethyl acetate in Hexane.

3.1. Scheme 3 Summary

In Scheme 3, substituted 2-bromo-benzene sulfonyl chlorides 38, 39, 40, and 41 were treated with 2-methyl allyl amine 26 in pyridine solution to yield 42, 43, 44 and 45, respectively. Radical reactions using TBTH and AIBN of 42, 43, 44, and 45 yielded radical derived products 46, 47, 48, and 49, respectively. Reactions of 46, 47, 48 and 49 with (2S,3S)-1,2-epoxy-3-(boc-amino)-4-phenylbutane (29) in DMF solution and Cs$_2$CO$_3$ yielded 50, 51, 52 and 53 as a mixture of diastereomers, respectively. Upon treatment with TFA:DCM (1:1) and separation using preparative TLC yielded two sets of pure diastereomers represented by structures 54, 55, 56 and 57 possessing S—R—R absolute stereochemistry and 58, 59, 60 and 61 possessing S—R—S absolute stereochemistry. Reaction of 54, 55, 56 and 57 with di-tert-butyl carbonate and di-isopropyl-N-ethylamine yielded 12, 18, 20 and 22, respectively. Similarly 58, 59, 60 and 61 yielded 13, 19, 21 and 23, respectively.

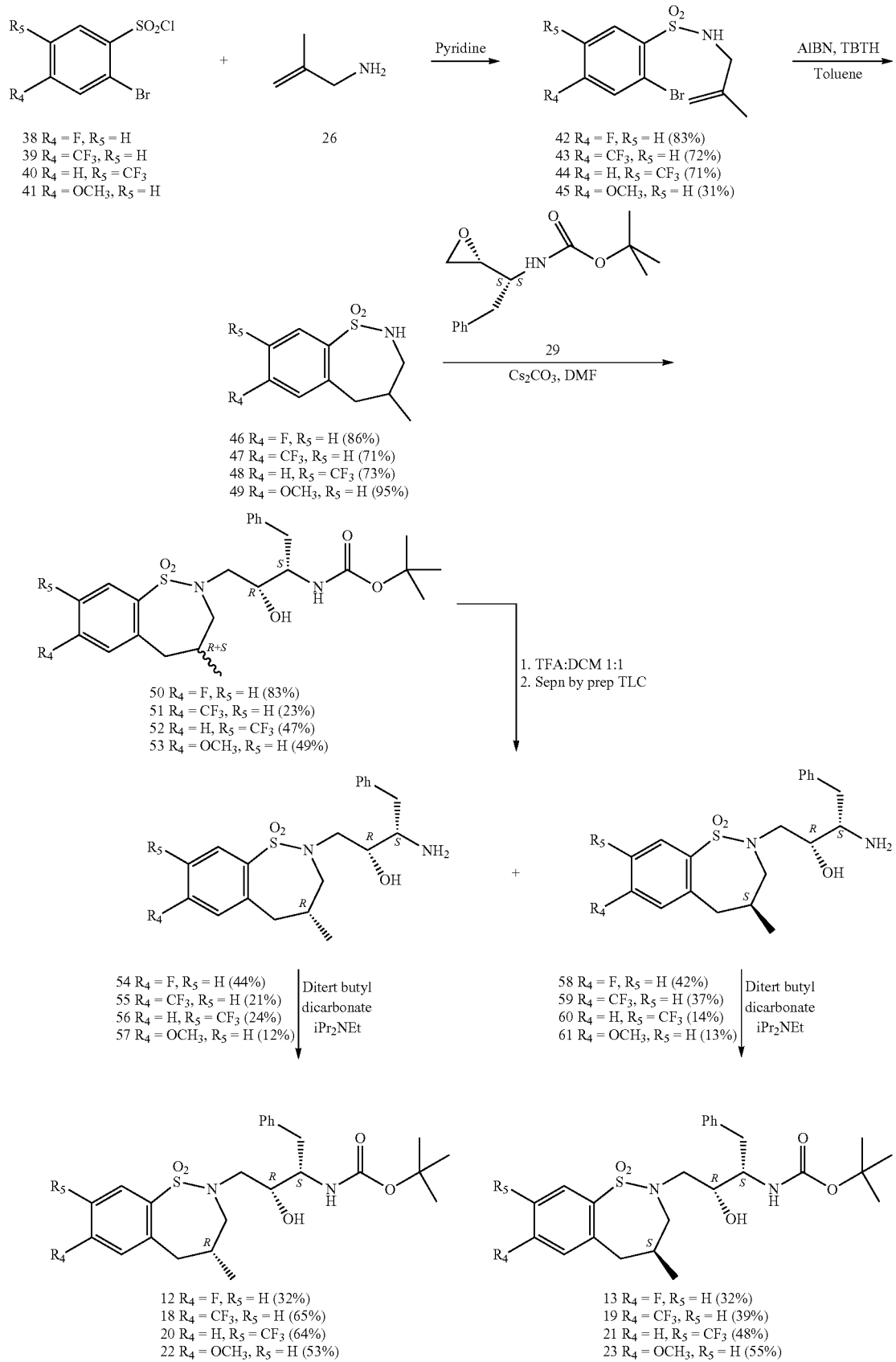

3.1. Synthesis Protocols

Compounds 42, 46, 50, 54/58, 12, and 13 were synthesized according to the procedures of compounds 27, 28, 30, 31/32, 14 and 15 substituting 2-bromobenzenesulfonyl chloride for 2-bromo-4-fluorobenzenesulfonyl chloride.

Compounds 43, 47, 51, 55/59, 18 and 19 were synthesized according to the procedures of compounds 27, 28, 30, 31/32, 14 and 15 substituting 2-bromobenzenesulfonyl chloride for 2-bromo-4-(trifluoromethyl)benzenesulfonyl chloride.

Compounds 44, 48, 52, 56/60, 20 and 21 were synthesized according to the procedures of compounds 27, 28, 30, 31/32, 14 and 15 substituting 2-bromobenzenesulfonyl chloride for 2-bromo-5-(trifluoromethyl)benzenesulfonyl chloride.

Compounds 45, 49, 53, 57/61, 22 and 23 were synthesized according to the procedures of compounds 27, 28, 30, 31/32, 14 and 15 substituting 2-bromobenzenesulfonyl chloride for 2-bromo-4-methoxybenzenesulfonyl chloride.

Scheme 4.

Scheme 4 describes a general reaction scheme for making compounds represented by structure 24 and analogs.

4.1. Scheme 4 Summary

In Scheme 4, aniline (62) and benzyl chloroformate (63) are reacted in the presence of $NaHCO_3$ and acetone:water (2:1) to generate benzyl N-phenylcarbamate (64), which when reacted with $Cs_2CO_3$ and (S)-(+)-glycidyl butyrate (65), in DMF solution gives the 5-(hydroxymethyl)-3-phenyloxazolidin-2-one (66), which upon treatment with $NaIO_4$, $RuCl_3$, $H_2O$ generates (67).

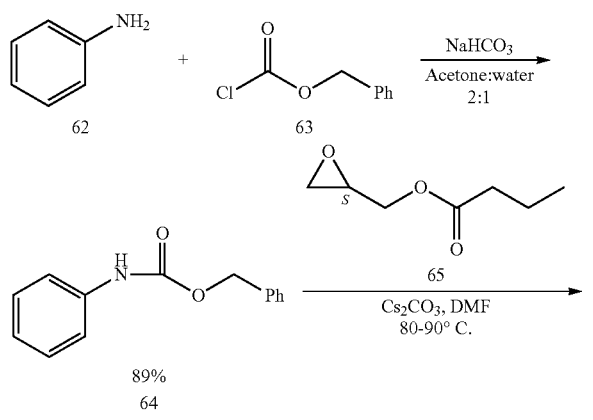

Reaction of 58 with 67 in DCM and in the presence of dicyclohexyl carbodiimide yielded 24

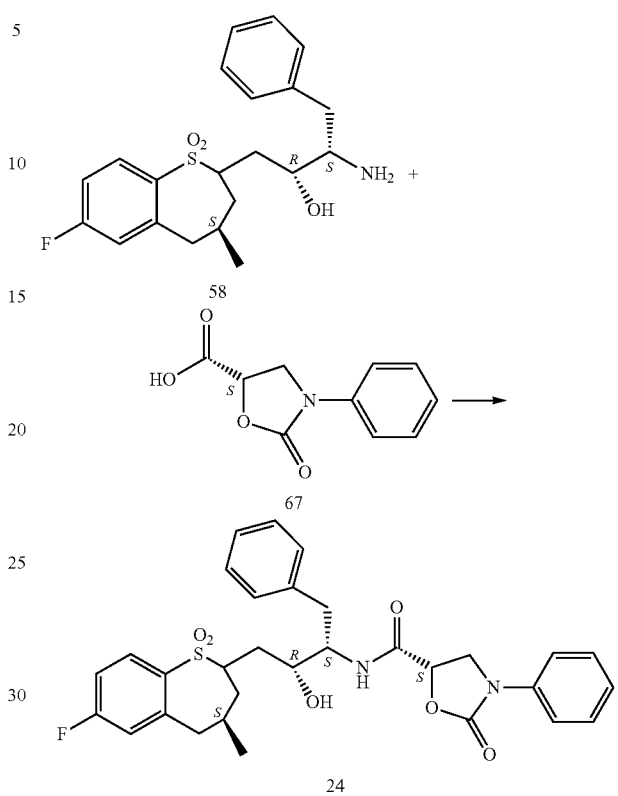

4.2. Synthesis Protocols

Compound 64

Aniline (1.00 g, 10.74 mmol)(62) was dissolved in a 2:1 mixture of acetone (6 mL) and water (3 mL). The solution was stirred on ice and solid sodium bicarbonate (1.89 g, 22.55 mmol) was added. To this mixture, benzyl chloroformate (1.83 g, 10.74 mmol)(63) was added. The reaction mixture was allowed to warm to room temperature and stirred for 10-12 hours under nitrogen. To an ice water slurry (50 mL), the reaction mixture was added. Solid, white precipitate formed immediately and was allowed to stay in the water slurry for 20 minutes. The crude solid was isolated by vacuum filtration and washed with water (10 mL). The crude solid was dissolved in ethyl acetate (20 mL) and washed with water (10 mL). The aqueous layer and filtrate were combined and washed with ethyl acetate (30 mL). The combined organic layers were dried over anhydrous sodium sulfate and evaporated to yield Compound 64 (2.161 g, 89%). Compound 64 was recrystallized from ethyl acetate/hexane.

Compound 66

To a solution of Compound 64 (100 mg, 0.44 mmol) in DMF (2 mL), (S)-(+)-glycidyl butyrate (63.4 mg, 0.44 mmol) (65) was added. Cesium carbonate (287 mg, 0.88 mmol) was added and the reaction mixture was heated to 80-90° C. for 3 hours. The progress of the reaction was monitored by TLC. Upon completion of the reaction, cesium carbonate was filtered out of the reaction mixture. The reaction mixture was taken in water (10 mL) and washed with ethyl acetate (3×15 mL). The combined organic layers were dried over anhydrous sodium sulfate and evaporated to dry to yield the crude compound. The crude compound was purified by column chromatography using 15% ethyl acetate in hexane to yield compound 66 (40 mg, 47%)

Compound 67

To a solution of compound 66 (90 mg, 0.46 mmol) in 1:1 mixture of carbon tetrachloride (2 mL) and acetonitrile (2 mL), a solution of sodium periodate (349 mg, 1.63 mmol) dissolved in ice water (3 mL) was added. To this mixture, ruthenium chloride hydrochloride salt (4.8 mg, 0.023 mmol) was added and allowed to stir for 10-12 hours under nitrogen. The progress of the reaction was monitored by TLC. Upon completion of the reaction, the ruthenium chloride hydrochloride salt was filtered off by vacuum filtration. The filtered solid was washed thoroughly with DCM (10 mL). The filtrate was dried over anhydrous sodium sulfate and evaporated. The crude product was then dissolved in ethyl acetate (5 mL) and washed with saturated sodium bicarbonate solution (2×1 mL). The organic layer was discarded, and the aqueous layer was acidified with conc. HCl and washed with ethyl acetate (3×25 mL). The combined organic layers were dried over anhydrous sodium sulfate and evaporate to dry to yield compound 67 (52 mg, 54%).

Compound 24

To a solution of Compound 58 (50 mg, 0.127 mmol) in DCM (3 mL), dicyclohexylcarbodiimide (DCCI) (24.1 mg, 0.191 mmol) was added, and the mixture was stirred well. Compound 67 (29.0 mg, 0.14 mmol) was added and the reaction was stirred for 10-12 hours at room temperature under nitrogen. The reaction progress was monitored by TLC. Upon completion of the reaction, the reaction mixture was taken in water (10 mL) and washed with DCM (3×15 mL). The combined organic layers were dried with anhydrous sodium sulfate and evaporated to yield the crude compound. Compound 24 was separated by preparatory TLC (7.5% methanol in chloroform).

According to some embodiments, $R^4$=F and $R^5$=H. According to some embodiments, $R^4$=$CF_3$ and $R^5$=H. According to some embodiments, $R^4$=H and $R^5$=$CF_3$. According to some embodiments, $R^4$=$OCH_3$ and $R^5$=H.

According to some embodiments, $R^4$ and $R^5$ each independently is H, a halogen, F, Cl, Br, I, a nitrile (CN), a carboxylic acid (COOH), a carbonyl (CO), a carboxyl group, an aldehyde (—CHO), acyl groups

aliphatic, aromatic or heterocyclic esters, a nitro group ($NO_2$), trifluoromethyl, methoxy, trifluoromethoxy, difluoromethoxy, an alkyl group, an alcohol group, an amino group, an amide, sulphonamide and urea substitution. Generally, a compound incorporating an $R^4$ electron donating group (such as, for example, methoxy) is much more active than a compound incorporating an $R^4$ electron withdrawing group (such as, for example, trifluoromethyl).

Unless defined otherwise, all technical and scientific terms used herein have the same meaning as commonly understood by one of ordinary skill in the art to which this invention belongs. Although any methods and materials similar or equivalent to those described herein also can be used in the practice or testing of the present invention, the preferred methods and materials are now described. All publications mentioned herein are incorporated herein by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention may be embodied in other specific forms without departing from the spirit or essential attributes thereof and, accordingly, reference should be made to the appended claims, rather than to the foregoing specification, as indicating the scope of the invention.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. The examples are set forth primarily for illustrative purposes and any specific contained therein should not be construed as limitations on the inventive concept. Efforts have been made to ensure accuracy with respect to numbers used (e.g., amounts, temperatures, etc.) but some experimental errors and deviations should be accounted for. Unless indicated otherwise, parts are by weight, molecular weight is weight average molecular weight, temperature is in degrees Centigrade, and pressure is at or near atmospheric.

Example 1

In Vitro HIV-1 Protease Assay

Compounds were evaluated for the ability to inhibit the enzymatic activity of HIV-1 protease in an in vitro assay. Protease activity was assessed in reactions catalyzed by purified HIV-1 protease at a concentration of 15 picomolar in buffer (50 mM sodium acetate, pH 5.5, 100 mM NaCl, 1 mg/mL bovine serum albumin) using a peptide substrate with sequence Val-Ser-Gln-Asn-(beta-naphthylalanine)-Pro-Ile- Val at a concentration of 440 micromolar in a final volume of 80 microliters. Compounds in DMSO stock were added to a final DMSO concentration of 2.5% and preincubated with enzyme prior to the initiation of the reaction by addition of substrate. Reactions were incubated at 30° C. for 60 minutes and were then quenched by the addition of 120 microliters 10% $H_3PO_4$. The amount of product formed was determined using high performance liquid chromatography with a Vydac C18 column and fluorescence detection of product. Percent inhibition was determined relative to control reactions without inhibitor, and half maximal inhibitory concentration ($IC_{50}$) values were determined using a standard four parameter fit to the inhibition data. The $IC_{50}$ is a quantitative measure of the effectiveness of a compound in inhibiting biological or biochemical function that indicates how much a particular compound or other substance is needed to inhibit a given biological process (or component of a process) by half.

Table 5 shows the $IC_{50}$ and polarity (as determined by thin layer chromatography) measured for 24 compounds of the described invention. These results demonstrate that when comparing the two diastereoisomers, the more active compounds in the C4 methyl and C4 phenyl series are consistently more polar than the corresponding diastereoisomer. Further, these results demonstrate that compounds having an SRS(S(C3')-R(C2')-S(C4)) configuration are active inhibitors of HIV-1 protease; compounds having an SRR(S(C3')-R(C2')-R(C4)) configuration demonstrated minimal or no inhibition of HIV-1 protease. The data show that the closed ring structure, the nature of the substitutions at R, $R^1$, $R^2$ and $R^3$, and the stereochemistry of the compounds of Formula I affect their biological activity. The compound where R=H is much less active, therefore R is an important constituent for activity. As described above, R, $R^1$, $R^2$ and $R^3$, each independently are:

R=H, alkyl, aryl, aryl alkyl, alkenyl, cycloalkyl, cycloalkenyl, alkylcycloalkyl, heterocycles, and substitutions thereof,

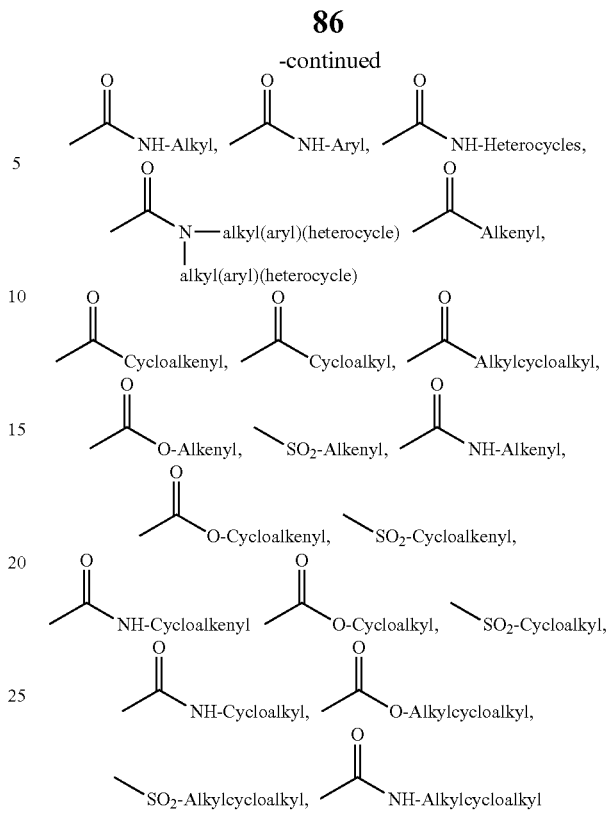

$R^2$ and $R^3$ are each independently H, an electron donating groups, or an electron withdrawing group at some or all the positions on the aromatic ring, halogens (F, Cl, Br, or I); nitriles (CN); carboxylic acids (COOH); carbonyls (CO); carboxyl groups, -aldehydes (—CHO), acyl groups

aliphatic, aromatic or heterocyclic esters, nitro groups ($NO_2$), tetrafluoromethyl, alkyl groups; alcohol groups; methoxy, and amino groups.

TABLE 5

(abbreviations: MW = molecular weight; TLC = thin layer chromatography; IC50 = half maximal inhibitory concentration).

| No. | Compound | Molecular Formula | MW | HIV Protease (IC50 in nM) | Polarity (TLC) |
|---|---|---|---|---|---|
| 1 | 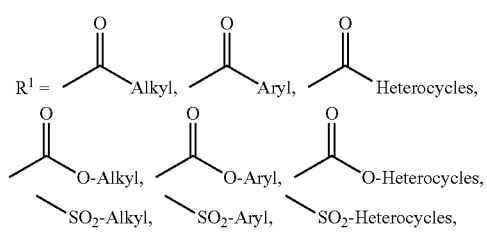 | $C_{24}H_{32}N_2O_5S$ | 460.59 | 2800 3050 | * * * |

TABLE 5-continued
(abbreviations: MW = molecular weight; TLC = thin layer chromatography; IC50 = half maximal inhibitory concentration).
| No. | Compound | Molecular Formula | MW | HIV Protease (IC50 in nM) | Polarity (TLC) |
|---|---|---|---|---|---|
| 2 | 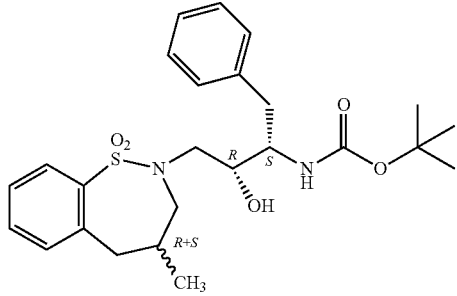 | $C_{25}H_{34}N_2O_5S$ | 474.61 | 240 220 | * * * |
| 3 | 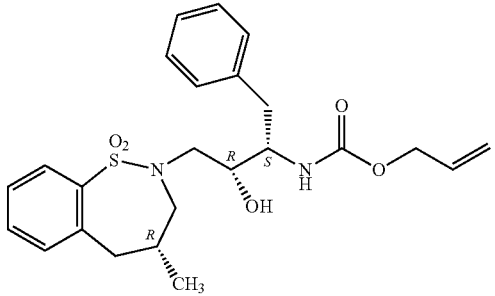 | $C_{24}H_{30}N_3O_5S$ | 458.19 | 5961 | Less polar |
| 4 | 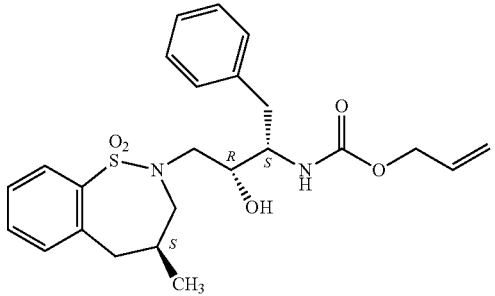 | $C_{24}H_{30}N_2O_5S$ | 458.19 | 157 | More polar |
| 5 | 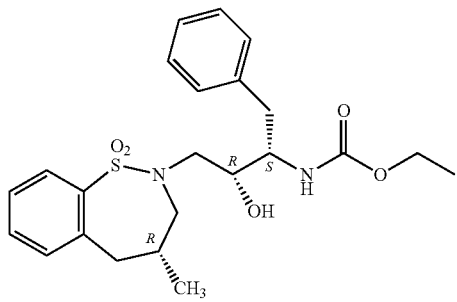 | $C_{23}H_{30}N_2O_5S$ | 446.19 | 10809 | Less polar |

TABLE 5-continued (abbreviations: MW = molecular weight; TLC = thin layer chromatography; IC50 = half maximal inhibitory concentration).

| No. | Compound | Molecular Formula | MW | HIV Protease (IC50 in nM) | Polarity (TLC) |
|---|---|---|---|---|---|
| 6 | | $C_{23}H_{30}N_2O_5S$ | 446.19 | 199 | More polar |
| 7 | | $C_{30}H_{36}N_2O_5S$ | 536.68 | 455 | * * * |
| 8 | | $C_{29}H_{32}N_2O_5S$ | 520.20 | 3257 | Less polar |
| 9 | | $C_{29}H_{32}N_2O_5S$ | 520.20 | 470 | More polar |

TABLE 5-continued (abbreviations: MW = molecular weight; TLC = thin layer chromatography; IC50 = half maximal inhibitory concentration).

| No. | Compound | Molecular Formula | MW | HIV Protease (IC50 in nM) | Polarity (TLC) |
|---|---|---|---|---|---|
| 10 | | $C_{28}H_{32}N_2O_5S$ | 508.20 | 2438 | Less polar |
| 11 | | $C_{28}H_{32}N_2O_5S$ | 508.20 | 864 | More polar |
| 12 | | $C_{25}H_{33}FN_2O_5S$ | 492.60 | 15719.728 | Less polar |
| 13 | | $C_{25}H_{33}FN_2O_5S$ | 492.60 | 119.340 | More polar |

TABLE 5-continued (abbreviations: MW = molecular weight; TLC = thin layer chromatography;
IC50 = half maximal inhibitory concentration).

| No. | Compound | Molecular Formula | MW | HIV Protease (IC50 in nM) | Polarity (TLC) |
|---|---|---|---|---|---|
| 14 | | $C_{25}H_{34}N_2O_5S$ | 474.61 | 5472.010 | Less polar |
| 15 | | $C_{25}H_{34}N_2O_5S$ | 474.61 | 168.809 | More polar |
| 16 | | $C_{27}H_{30}N_2O_5S$ | 494.60 | 20000.000 | Less polar |
| 17 | | $C_{27}H_{30}N_2O_5S$ | 494.60 | 2057.063 | More polar |
| 18 | | $C_{26}H_{33}F_3N_2O_5S$ | 542.61 | 20000.000 | Less polar |

TABLE 5-continued (abbreviations: MW = molecular weight; TLC = thin layer chromatography; IC50 = half maximal inhibitory concentration).

| No. | Compound | Molecular Formula | MW | HIV Protease (IC50 in nM) | Polarity (TLC) |
|---|---|---|---|---|---|
| 19 | | $C_{26}H_{33}F_3N_2O_5S$ | 542.61 | 1118.184 | More polar |
| 20 | | $C_{26}H_{33}F_3N_2O_5S$ | 542.61 | 8296.937 | Less polar |
| 21 | | $C_{26}H_{33}F_3N_2O_5S$ | 542.61 | 611.706 | More polar |
| 22 | | $C_{26}H_{36}N_2O_6S$ | 504.64 | 6100.064 | Less polar |
| 23 | | $C_{26}H_{36}N_2O_6S$ | 504.64 | 106.876 | More polar |

TABLE 5-continued (abbreviations: MW = molecular weight; TLC = thin layer chromatography;
IC50 = half maximal inhibitory concentration).

| No. | Compound | Molecular Formula | MW | HIV Protease (IC50 in nM) | Polarity (TLC) |
|---|---|---|---|---|---|
| 24 |  | $C_{30}H_{32}FN_3O_6S$ | 581.65 | 175.672 | *** |

Sterochemistry: SRS vs. SRR

Compounds of Formula I were synthesized to illustrate the affect of the absolute configuration at the C3' atom, C2' atom and C4 atom on the biological activity of these compounds.

As for Compound 1, compound 1 is a compound of Formula I, where R=H, and R1=tert-butyl.

Compound 2 is a mixture of two diastereomers whereby the chiral center of the C4 atom is of R absolute configuration or S absolute configuration. Even though compound 2 is a mixture of two diastereomers it shows ten-fold greater activity than that of compound 1, where R=H. As for Compounds 14 and 15, where R=$CH_3$, and $R^1$=t-butyl, analysis of Compounds 14 and 15 further illustrated the affect of the absolute configuration at the C4 atom on the biological activity of the compounds. Compound 15, with a stereochemistry of S(C3')-R(C2')-S(C4) (hereafter referred to as "SRS absolute configuration"), demonstrated higher biological activity than that of Compound 14, with a stereochemistry of S(C3')-R(C2')-R(C4) (hereafter referred to as "SRR absolute configuration").

As for Compounds 4 and 5, analysis of these compounds of Formula I, where R=$CH_3$, and where $R^1$=alkenyl, further illustrated the affect of stereochemistry and substitutions on the biological activity of compounds of Formula I. Compound 4, with an SRS(S(C3')-R(C2')-S(C4)) absolute configuration, demonstrated approximately 40-fold higher biological activity than Compound 3, with a SRR(S(C3')-R (C2')-R(C4)) absolute configuration.

As for Compounds 5 and 6, where R=$CH_3$, and $R^1$=alkyl, analysis of Compound 6, with a SRS(S(C3')-R(C2')-S(C4)) absolute configuration, demonstrated approximately 54-fold higher biological activity than Compound 5, with a SRR(S (C3')-R (C2')-R(C4)) absolute configuration.

As for Compounds 16 and 17, where R=$CH_3$, and $R^1$=Ph, analysis of Compound 17, with a SRS(S(C3')-R(C2')-S(C4)) absolute configuration, demonstrated approximately 10-fold higher biological activity than Compound 16, with a SRR(S (C3')-R (C2')-R(C4)) absolute configuration.

These results illustrate that the compounds of Formula I having a S(C3')-R (C2')-S(C4) stereochemistry have higher biological activity than compounds of Formula I having a S(C3')-R(C2')-R(C4) stereochemistry. Further, these results show that biological activity of the compounds of Formula I is affected by the substituent group at the $R^1$ position of the compound. For example, analysis of the S(C3')-R(C2')-R (C4) diasteromers of Compounds 7-11, where R=Ph, and where $R^1$=alkyl or an alkenyl, all demonstrated higher biological activity than the S(C3')-R(C2')-S(C4) diastereomers.

R Position Substitutions

Substitutions at the R position of the compound of Formula I also affected biological activity of the compound. Suitable $R^2$ substitutions may include amines, amides, trichloro, trifluoro, methoxy or other electron donating groups. Compound 7, where R=Ph, showed biological activity higher than that of Compound 1 (where R1=H), and similar to that of Compounds 2 and 3 (R=$CH_3$). Additionally, as for Compounds 8 and 9, where R=Ph and where $R^1$=alkenyl, Compound 9, having a SRR(S(C3')-R(C2')-R(C4)) absolute configuration, demonstrated higher biological activity than that of Compound 3 (where R=$CH_3$ and where $R^1$=alkenyl), while Compound 8, with a SRS(S(C3')-R(C2')-S(C4)) absolute configuration, demonstrated lower biological activity than that of Compound 9, and that of Compound 4 (where R=$CH_3$ and where $R^1$=alkenyl), having a SRS(S(C3')-R(C2')-S(C4)) absolute configuration.

Similarly, in Compounds 10 and 11, R=Ph, and $R^1$=alkyl. Analysis of Compound 11, with a SRR(S(C3')-R(C2')-R (C4)) absolute configuration, demonstrated higher biological activity than that of Compound 10, with a SRS(S(C3')-R (C2')-S(C4)) absolute configuration, but still less than Compound 6 (where R=$CH_3$ and where $R^1$=alkyl), with a SRS(S (C3')-R(C2')-S(C4)) absolute configuration.

For Compounds 16 and 17, where $R^1$=Ph, and R=$CH_3$. Analysis of these compounds illustrated the affect of stereochemistry and substitution on the biological activity of compounds of Formula I. Compound 17, having a SRS(S(C3')-R (C2')-S(C4)) absolute configuration, demonstrated higher activity than Compound 16, having a SRR(S(C3')-R(C2')-R (C4)) absolute configuration, but still less than that of compounds where R=alkenyl (Compound 4), t-butyl (Compound 15), or alkyl (Compound 6).

These results suggest that the biological activity of a compound of Formula I is influenced by the substituent as well as the stereochemistry of the compound at the R position and at the $R^1$ position.

$R^2$ Position Substitutions:

For Compound 12 and Compound 13, $R^2$=a halogen. Compound 13, with a SRS (S(C3')-R(C2')-S(C4)) absolute configuration, demonstrated an approximate 132-fold higher biological activity than Compound 12, with a SRR(S(C3')-R (C2')-R(C4)) absolute configuration. It may have advantages in metabolism. Further, analysis of Compound 13 also had higher biological activity than Compound 15.

For Compound 18 and Compound 19, $R^2$ is an electron withdrawing $CF_3$ group. Compound 19, with a SRS(S(C3')-R(C2')-S(C4)) absolute configuration, demonstrated an approximate 18-fold higher biological activity than Compound 18, with a SRR(S(C3')-R(C2')-R(C4)) absolute configuration. However, even SRS(S(C3')-R(C2')-S(C4)) conformation is not very active when compared to a compound where $R^2$=H.

For Compound 22 and Compound 23, $R^2$ is electron donating group methoxy. Compound 22 with SRR(S(C3')-R(C2')-R(C4)) stereochemistry is not active while compound 23, with SRS(S(C3')-R(C2')-S(C4)) geometry, has excellent activity. Compound 23, with a SRS(S(C3')-R(C2')-S(C4)) absolute configuration, demonstrated an approximate 57-fold higher biological activity than did Compound 22, with a SRR(S(C3')-R(C2')-R(C4)) absolute configuration.

These results show that a different substitution at $R^2$ may provide a more beneficial affect than when compared to hydrogen substitution.

$R^3$ Position Substitutions: Electron-Withdrawing Groups

Activities of Compounds 20 and 21 show the effect of moving electron withdrawing group from $R^2$ to $R^3$. For Compound 20 and Compound 21, $R^3$ is an electron withdrawing group $CF_3$. Compound 21, with a SRS(S(C3')-R(C2')-S(C4)) absolute configuration, showed an approximate 14-fold higher biological activity than Compound 20, with a SRR(S(C3')-R(C2')-R(C4)) absolute configuration. These results show that an electron withdrawing group ($CF_3$) at $R^3$, improves the biological activity of a compound of Formula I relative to the activity of compounds 18 and 19.

$R^1$ Position Substitution: Amide

Compound 24 is an SRSS compound (stereochemistry of S(C3')-R(C2')-S(C4)-S(C5')). This compound was highly active. These results suggest additional $R^1$ substitutions on the aromatic ring, such as, but not limited to, substituted aromatics and heterocycles may improve biological activity of compounds of Formula I.

We claim:
1. A compound of formula

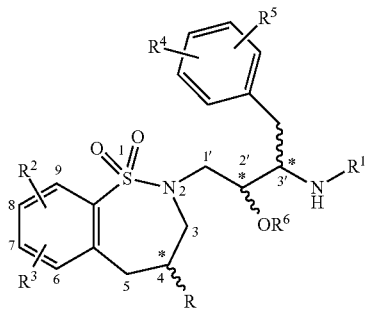

wherein R, $R^1$, $R^2$, $R^3$, $R^4$, $R^5$ and $R^6$ each independently are:

R=H, an alkyl, wherein the alkyl is a straight or branched hydrocarbon chain having from 1 to 25 of carbon atoms, an aryl, wherein the aryl is a substituted benzene ring, system fused to one or more substituted benzene ring an aryl alkyl, a heterocycle, wherein the heterocycle is a three to twelve-membered heterocyclic ring optionally possessing one or more degrees of unsaturation, and containing one or more heteroatomic substitutions selected from the group consisting of —S—, —SO—, —SO$_2$—, —O—, or —N—, a substitution of the alkyl, wherein one or more carbon atoms of the straight or branched hydrocarbon chain are substituted with a substituent selected from the group consisting of alkoxy, alkylsulfanyl, alkylsulfenyl, alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, and perfluoroalkyl;

a substitution of the aryl, wherein one or more carbon atoms of the one or more substituted benzene ring are substituted with a substituent selected from the group consisting of alkyl, alkoxy, alkylsulfanyl, alkylsulfenyl, alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, and perfluoroalkyl; and a substitution of the heterocycle, wherein one or more carbon atoms of the heterocyclic ring are substituted with a substituent selected from the group consisting of alkyl, alkoxy, alkylsulfanyl, alkylsulfenyl, alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, and perfluoroalkyl;

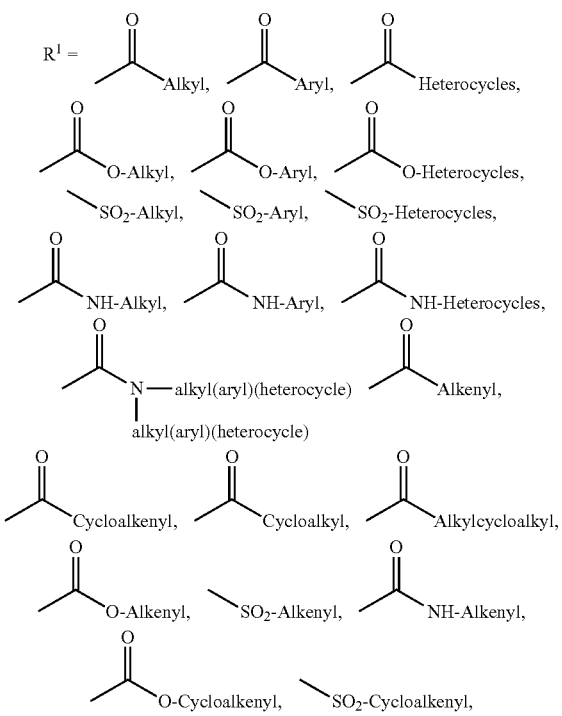

101

-continued

NH-Cycloalkenyl, O-Cycloalkyl, SO₂-Cycloalkyl,

NH-Cycloalkyl, O-Alkylcycloalkyl,

SO₂-Alkylcycloalkyl, NH-Alkylcycloalkyl,

[oxazolidinone structure with R⁷ on phenyl]

where R⁷=H, an electron donating group, or an electron withdrawing group at some or all the positions on the aromatic ring;

R², R³, R⁴, and R⁵ are each independently H, an electron donating group, or an electron withdrawing group at some or all the positions on the aromatic ring, wherein the electron donating group is selected from the group consisting of an alkyl group, an alcohol group, an alkoxy group, an amino group, and a phenolic group, and wherein the electron withdrawing group is selected from the group consisting of a halogen, a nitrile, a carboxylic acid, a carbonyl, a carboxylic group, and an aldehyde;

R⁶ is H, a phosphate or amino acid ester(s) or salt(s) thereof;

and where "*" represents a chiral center.

2. The compound according to claim 1, wherein the C4 carbon is of a S absolute configuration.

3. The compound according to claim 1, wherein the C2' carbon is of a R absolute configuration.

4. The compound according to claim 1, wherein the C3' carbon is of a S absolute configuration.

5. The compound according to claim 1, wherein the compound is

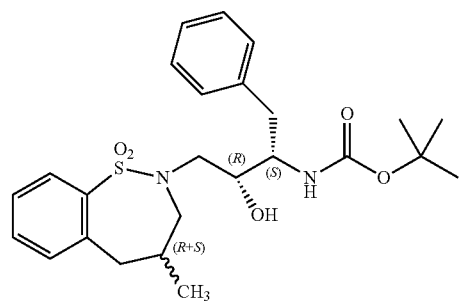

wherein the compound has stereochemistry of S(C3')-R(C2')-R+S(C4).

102

6. The compound according to claim 1, wherein the compound is

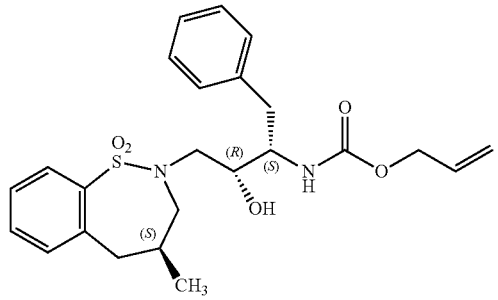

wherein the C3' carbon is of a S absolute configuration, the C2' carbon is of a R absolute configuration, and the C4 carbon is of a S absolute configuration.

7. The compound according to claim 1, wherein the compound is

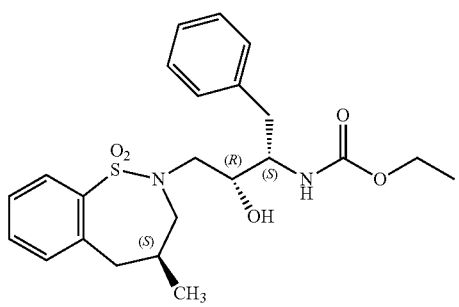

wherein the C3' carbon is of a S absolute configuration, the C2' carbon is of a R absolute configuration, and the C4 carbon is of a S absolute configuration.

8. The compound according to claim 1, wherein the compound is

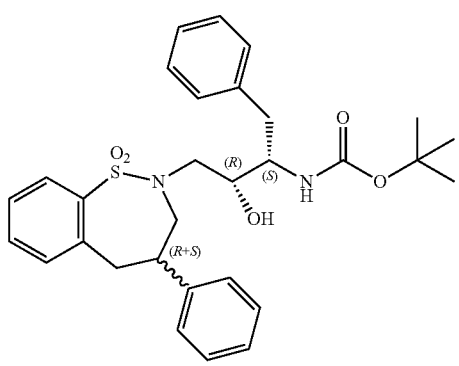

wherein the C3' carbon is of a S absolute configuration, the C2' carbon is of a R absolute configuration, and the C4 carbon is of a R absolute configuration or S absolute configuration.

9. The compound according to claim 1, wherein the compound is

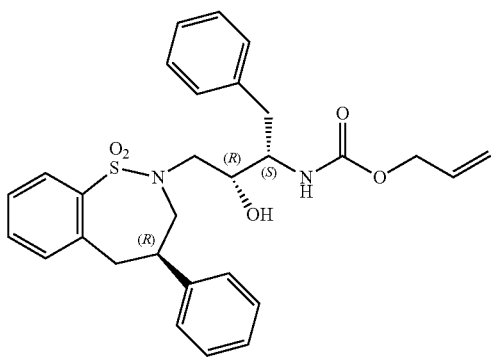

wherein the C3' carbon is of a S absolute configuration, the C2' carbon is of a R absolute configuration, and the C4 carbon is of a R absolute configuration.

10. The compound according to claim 1, wherein the compound is

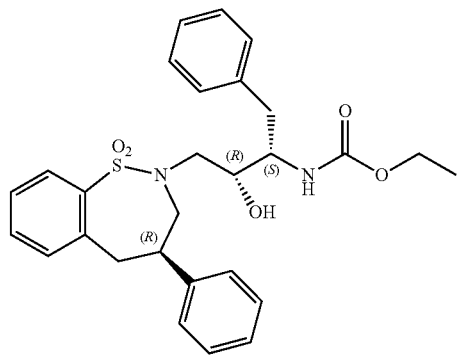

wherein the C3' carbon is of a S absolute configuration, the C2' carbon is of a R absolute configuration, and the C4 carbon is of a R absolute configuration.

11. The compound according to claim 1, wherein the compound is

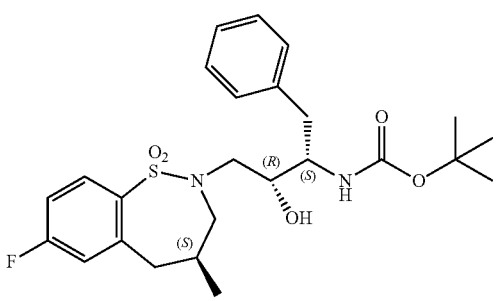

wherein the C3' carbon is of a S absolute configuration, the C2' carbon is of a R absolute configuration, and the C4 carbon is of a S absolute configuration.

12. The compound according to claim 1, wherein the compound is

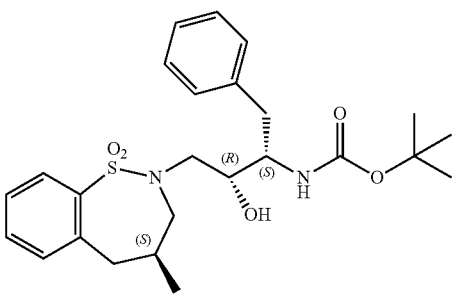

wherein the C3' carbon is of a S absolute configuration, the C2' carbon is of a R absolute configuration, and the C4 carbon is of a S absolute configuration.

13. The compound according to claim 1, wherein the compound is

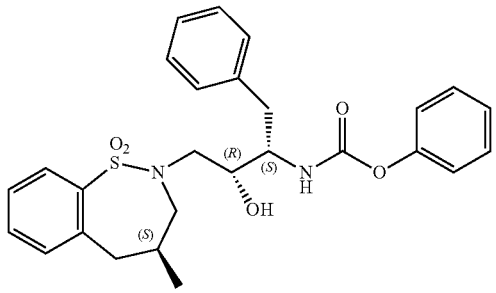

wherein the C3' carbon is of a S absolute configuration, the C2' carbon is of a R absolute configuration, and the C4 carbon is of a S absolute configuration.

14. The compound according to claim 1, wherein the compound is

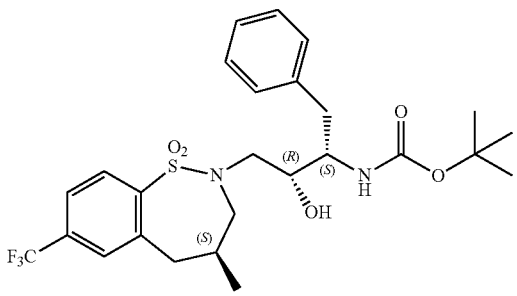

wherein the C3' carbon is of a S absolute configuration, the C2' carbon is of a R absolute configuration, and the C4 carbon is of a S absolute configuration.

15. The compound according to claim 1, wherein the compound is

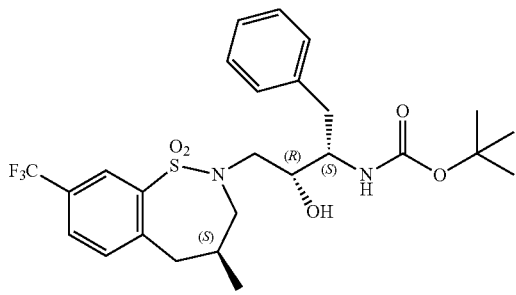

wherein the C3' carbon is of a S absolute configuration, the C2' carbon is of a R absolute configuration, and the C4 carbon is of a S absolute configuration.

16. The compound according to claim 1, wherein the compound is

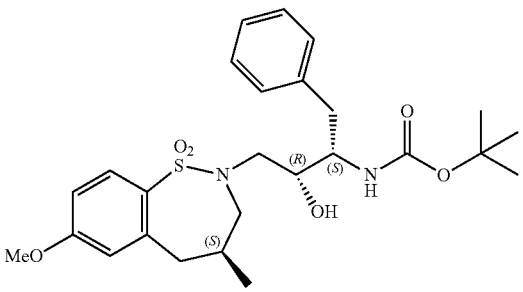

wherein the C3' carbon is of a S absolute configuration, the C2' carbon is of a R absolute configuration, and the C4 carbon is of a S absolute configuration.

17. The compound according to claim 1, wherein the compound is

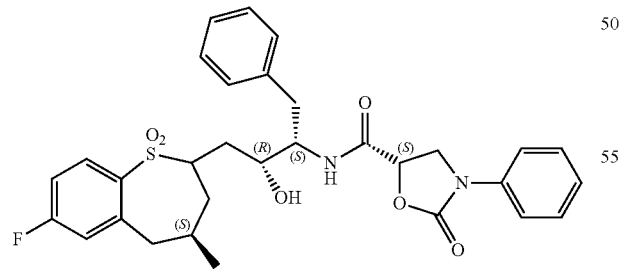

wherein the C3' carbon is of a S absolute configuration, the C2' carbon is of a R absolute configuration, the C4 carbon is of a S absolute configuration, and C5' carbon is of a S absolute configuration.

18. A composition for inhibiting HIV protease, the composition comprising a compound of formula

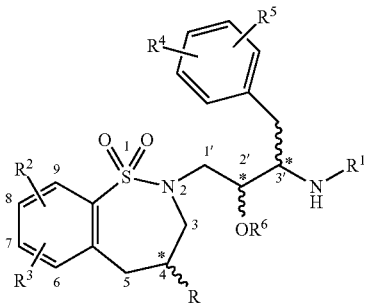

wherein R, $R^1$, $R^2$, $R^3$, $R^4$, $R^5$ and $R^6$ each independently are:

R=H, an alkyl, wherein the alkyl is a straight or branched hydrocarbon chain having from 1 to 25 of carbon atoms, an aryl, wherein the aryl is a substituted benzene ring, system fused to one or more substituted benzene ring an aryl alkyl, a heterocycle, wherein the heterocycle is a three to twelve-membered heterocyclic ring optionally possessing one or more degrees of unsaturation, and containing one or more heteroatomic substitutions selected from the group consisting of —S—, —SO—, —SO$_2$—, —O—, or —N—, a substitution of the alkyl, wherein one or more carbon atoms of the straight or branched hydrocarbon chain are substituted with a substituent selected from the group consisting of alkoxy, alkylsulfanyl, alkylsulfenyl, alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, and perfluoroalkyl;

a substitution of the aryl, wherein one or more carbon atoms of the one or more substituted benzene ring are substituted with a substituent selected from the group consisting of alkyl, alkoxy, alkylsulfanyl, alkylsulfenyl, alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, and perfluoroalkyl; and a substitution of the heterocycle, wherein one or more carbon atoms of the heterocyclic ring are substituted with a substituent selected from the group consisting of alkyl, alkoxy, alkylsulfanyl, alkylsulfenyl, alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, and perfluoroalkyl;

$R^1 =$ Alkyl, Aryl, Heterocycles,

-continued

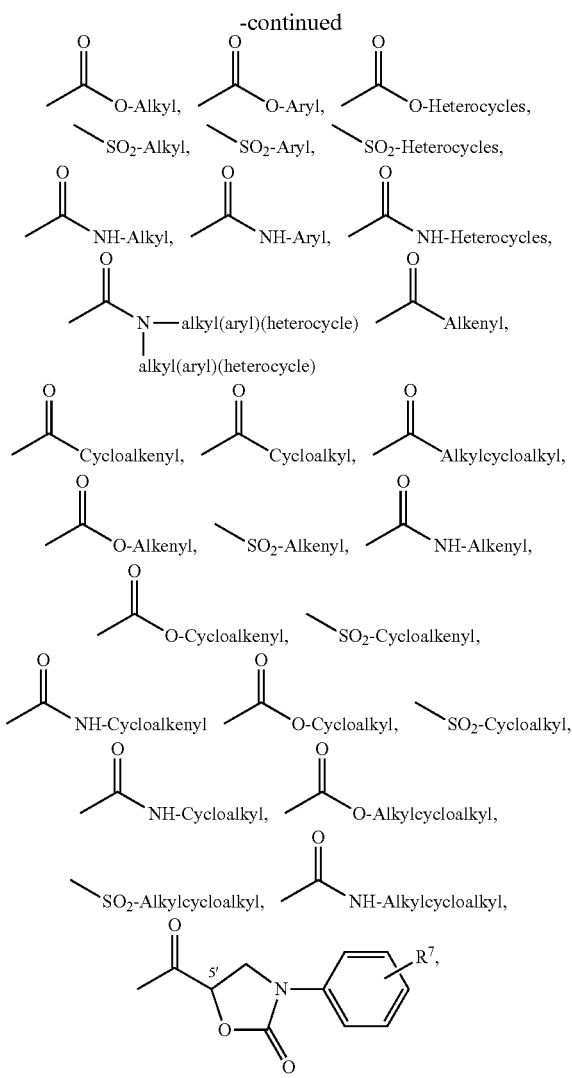

where R⁷=H, an electron donating group, or an electron withdrawing group at some or all the positions on the aromatic ring;

R², R³, R⁴, and R⁵ are each independently H, an electron donating group, or an electron withdrawing group at some or all the positions on the aromatic ring, wherein the electron donating group is selected from the group consisting of an alkyl group, an alcohol group, an alkoxy group, an amino group, and a phenolic group, and wherein the electron withdrawing group is selected from the group consisting of a halogen, a nitrile, a carboxylic acid, a carbonyl, a carboxylic group, and an aldehyde;

R⁶ is H, a phosphate or amino acid ester(s) or salt(s) thereof;

wherein "*" represents a chiral center, and a pharmaceutically acceptable carrier.

19. The composition according to claim 18, wherein the C4 carbon is of a S absolute configuration.

20. The composition according to claim 18, wherein the C2' carbon is of a R absolute configuration.

21. The composition according to claim 18, wherein the C3' carbon is of a S absolute configuration.

22. The composition according to claim 18, wherein the compound is

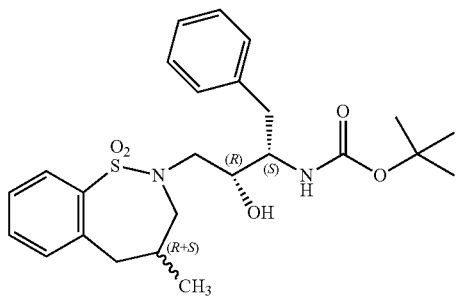

wherein the C3' carbon is of a S absolute configuration, the C2' carbon is of a R absolute configuration, and the C4 carbon is of a R absolute configuration or a S absolute configuration.

23. The composition according to claim 18, wherein the compound is

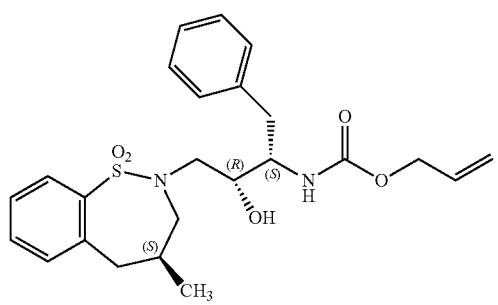

wherein the C3' carbon is of a S absolute configuration, the C2' carbon is of a R absolute configuration, and the C4 carbon is of a S absolute configuration.

24. The composition according to claim 18, wherein the compound is

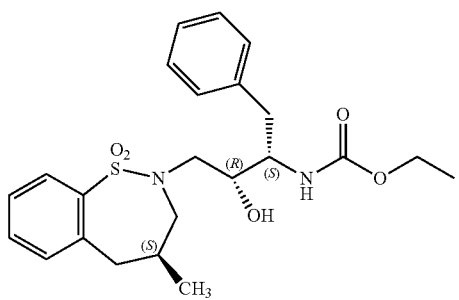

wherein the C3' carbon is of a S absolute configuration, the C2' carbon is of a R absolute configuration, and the C4 carbon is of a S absolute configuration.

25. The composition according to claim 18, wherein the compound is

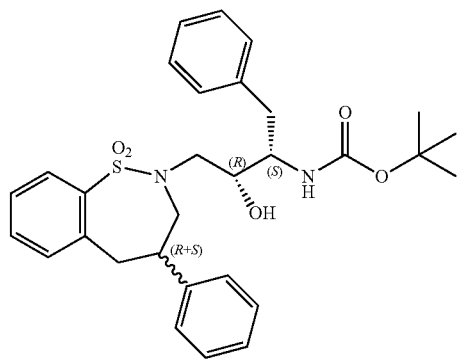

wherein the C3' carbon is of a S absolute configuration, the C2' carbon is of a R absolute configuration, and the C4 carbon is of a R absolute configuration or a S absolute configuration.

26. The composition according to claim 18, wherein the compound is

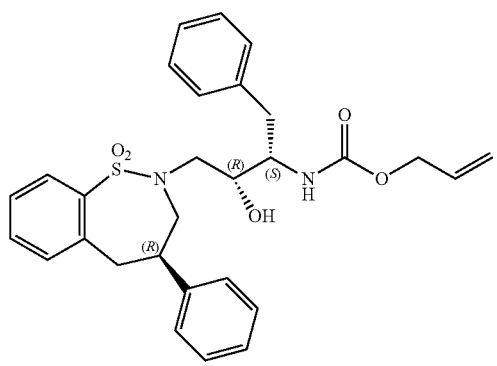

wherein the C3' carbon is of a S absolute configuration, the C2' carbon is of a R absolute configuration, and the C4 carbon is of a R absolute configuration.

27. The composition according to claim 18, wherein the compound is

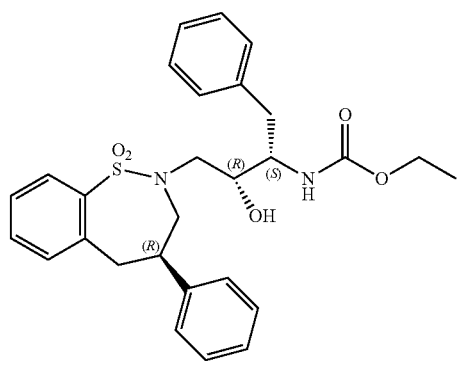

wherein the C3' carbon is of a S absolute configuration, the C2' carbon is of a R absolute configuration, and the C4 carbon is of a R absolute configuration.

28. The composition according to claim 18, wherein the compound is

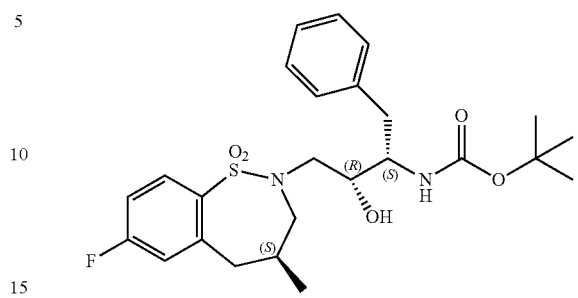

wherein the C3' carbon is of a S absolute configuration, the C2' carbon is of a R absolute configuration, and the C4 carbon is of a S absolute configuration.

29. The composition according to claim 18, wherein the compound is

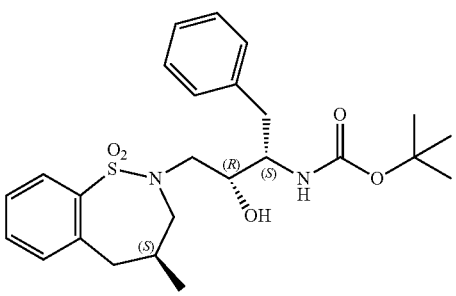

wherein the C3' carbon is of a S absolute configuration, the C2' carbon is of a R absolute configuration, and the C4 carbon is of a S absolute configuration.

30. The composition according to claim 18, wherein the compound is

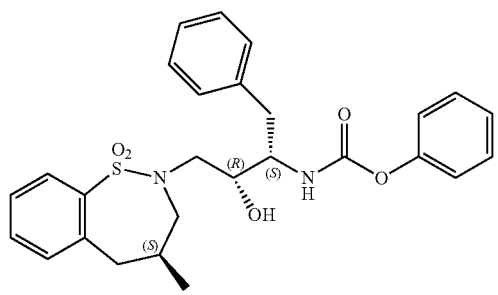

wherein the C3' carbon is of a S absolute configuration, the C2' carbon is of a R absolute configuration, and the C4 carbon is of a S absolute configuration.

31. The composition according to claim 18, wherein the compound is

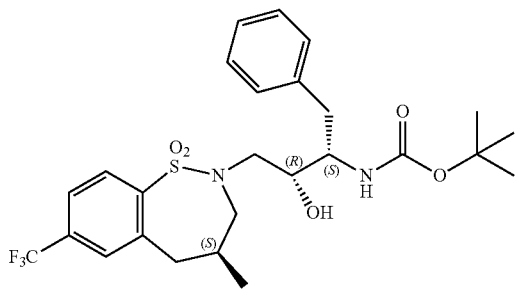

wherein the C3' carbon is of a S absolute configuration, the C2' carbon is of a R absolute configuration, and the C4 carbon is of a S absolute configuration.

32. The composition according to claim 18, wherein the compound is

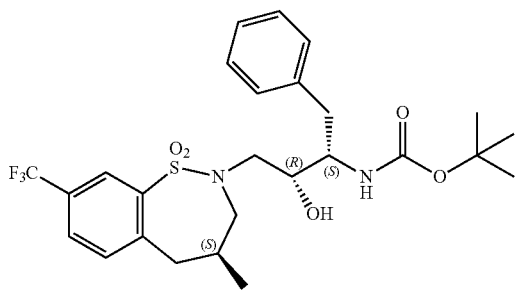

wherein the C3' carbon is of a S absolute configuration, the C2' carbon is of a R absolute configuration, and the C4 carbon is of a S absolute configuration.

33. The composition according to claim 18, wherein the compound is

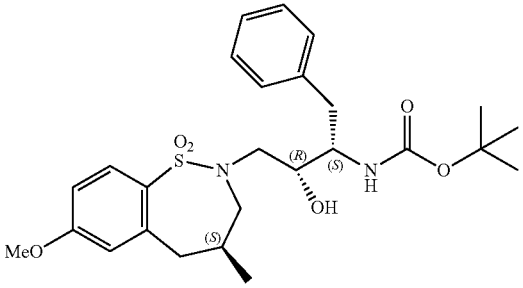

wherein the C3' carbon is of a S absolute configuration, the C2' carbon is of a R absolute configuration, and the C4 carbon is of a S absolute configuration.

34. The composition according to claim 18, wherein the compound is

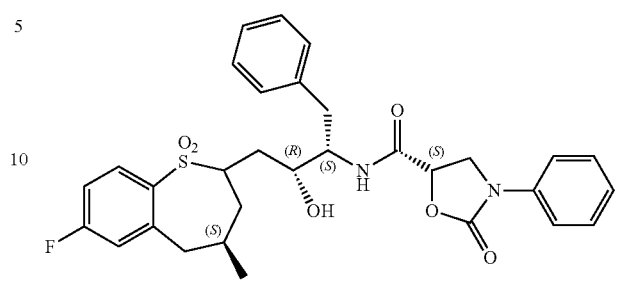

wherein the C3' carbon is of a S absolute configuration, the C2' carbon is of a R absolute configuration, the C4 carbon is of a S absolute configuration, and the C5' carbon is of a S absolute configuration.

35. A method for inhibiting a HIV protease in a subject, the method comprising steps:
(a) administering to a subject in need thereof a pharmaceutical composition comprising
(i) a therapeutically effective amount of a compound of formula:

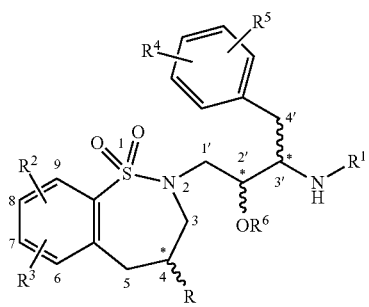

wherein R, $R^1$, $R^2$, $R^3$, $R^4$, $R^5$ and $R^6$ each independently are:

R═H, an alkyl, wherein the alkyl is a straight or branched hydrocarbon chain having from 1 to 25 of carbon atoms, an aryl, wherein the aryl is a substituted benzene ring system fused to one or more substituted benzene ring; an aryl alkyl, a heterocycle, wherein the heterocycle is a three to twelve-membered heterocyclic ring optionally possessing one or more degrees of unsaturation, and containing one or more heteroatomic substitutions selected from the group consisting of —S—, —SO—, —SO$_2$—, —O—, or —N—,
a substitution of the alkyl, wherein one or more carbon atoms of the straight or branched hydrocarbon chain are substituted with a substituent selected from the group consisting of alkoxy, alkylsulfanyl, alkylsulfenyl, alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, and perfluoroalkyl;
a substitution of the aryl, wherein one or more carbon atoms of the one or more substituted benzene ring are substituted with a substituent selected from the group consisting of alkyl, alkoxy, alkylsulfanyl, alkylsulfenyl, alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, and perfluoroalkyl; and a substitution of the heterocycle, wherein one or more carbon atoms of the heterocyclic ring are substituted with a substituent selected from the group consisting of alkyl, alkoxy, alkylsulfanyl, alkylsulfenyl, alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, and perfluoroalkyl;

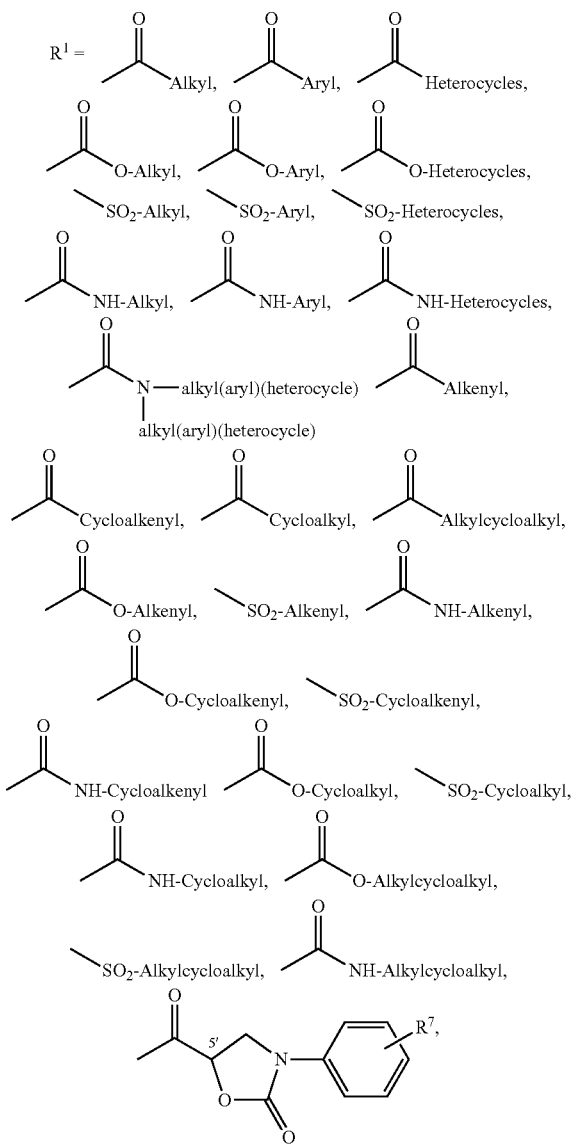

where $R^7$=H, an electron donating group, or an electron withdrawing group at some or all the positions on the aromatic ring;

$R^2$, $R^3$, $R^4$, and $R^5$ are each independently H, an electron donating group, or an electron withdrawing group at some or all the positions on the aromatic ring;

wherein the electron donating group is selected from the group consisting of an alkyl group, an alcohol group, an alkoxy group, an amino group, trifluoromethoxy, difluoromethoxy, amide, substituted amide, urea, substituted urea, sulphonamide, substituted sulphonamide, and a phenolic group, and wherein the electron withdrawing group is selected from the group consisting of a halogen, a nitrile, a carboxylic acid, a carbonyl, a carboxylic group, a nitro group, trifluoromethyl, difluoromethyl, nitro, sulphone, sulphonamide, amide, N-substituted amide, and an aldehyde;

$R^6$ is H, a phosphate or amino acid ester(s) or salt(s) thereof;

wherein "*" represents a chiral center, and (ii) a pharmaceutically acceptable carrier;

thereby reducing the enzymatic activity of a HIV protease.

36. The method according to claim 35, wherein the C4 carbon is of a S absolute configuration.

37. The method according to claim 35, wherein the C2' carbon is of a R absolute configuration.

38. The method according to claim 35, wherein the C3' carbon is of a S absolute configuration.

39. The method according to claim 35, wherein the compound is

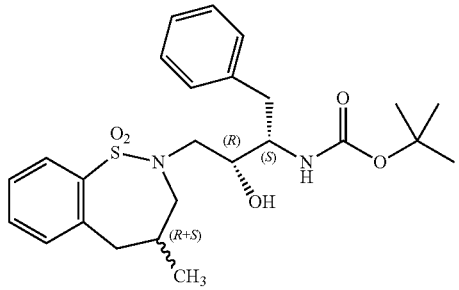

wherein the C3' carbon is of a S absolute configuration, the C2' carbon is of a R absolute configuration, and the C4 carbon is of a R absolute configuration or a S absolute configuration.

40. The method according to claim 35, wherein the compound is

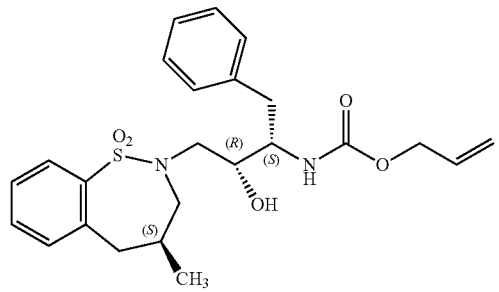

wherein the C3' carbon is of a S absolute configuration, the C2' carbon is of a R absolute configuration, and the C4 carbon is of a S absolute configuration.

41. The method according to claim 35, wherein the compound is

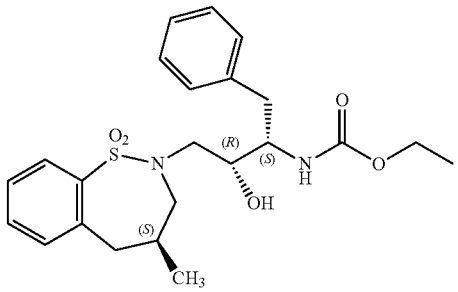

wherein the C3' carbon is of a S absolute configuration, the C2' carbon is of a R absolute configuration, and the C4 carbon is of a S absolute configuration.

42. The method according to claim 35, wherein the compound is

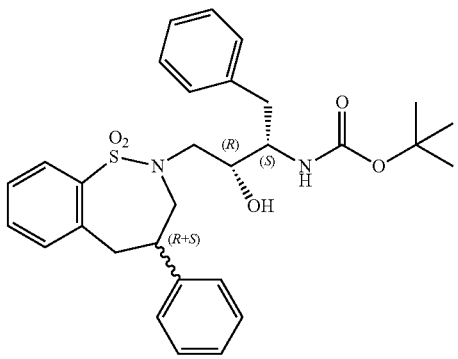

wherein the C3' carbon is of a S absolute configuration, the C2' carbon is of a R absolute configuration, and the C4 carbon is of a R absolute configuration or S absolute configuration.

43. The method according to claim 35, wherein the compound is

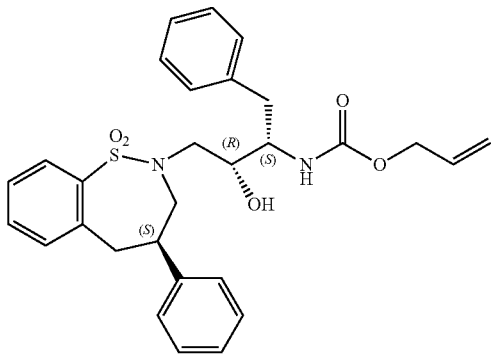

wherein the C3' carbon is of a S absolute configuration, the C2' carbon is of a R absolute configuration, and the C4 carbon is of a R absolute configuration.

44. The method according to claim 35, wherein the compound is

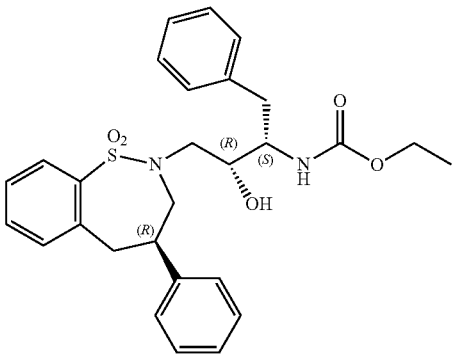

wherein the C3' carbon is of a S absolute configuration, the C2' carbon is of a R absolute configuration, and the C4 carbon is of a R absolute configuration.

45. The method according to claim 35, wherein the compound is

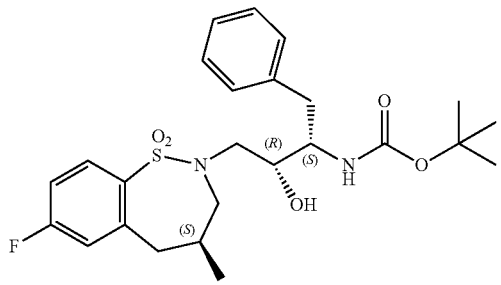

wherein the C3' carbon is of a S absolute configuration, the C2' carbon is of a R absolute configuration, and the C4 carbon is of a S absolute configuration.

46. The method according to claim 35, wherein the compound is

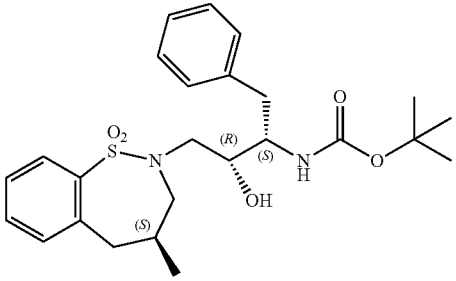

wherein the C3' carbon is of a S absolute configuration, the C2' carbon is of a R absolute configuration, and the C4 carbon is of a S absolute configuration.

47. The method according to claim 35, wherein the compound is

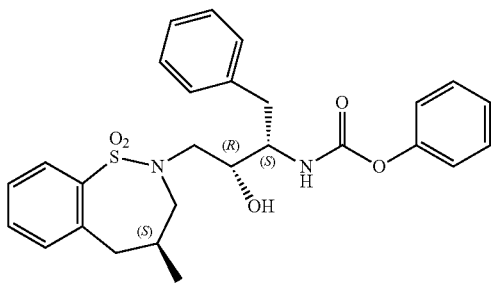

wherein the C3' carbon is of a S absolute configuration, the C2' carbon is of a R absolute configuration, and the C4 carbon is of a S absolute configuration.

48. The method according to claim 35, wherein the compound is

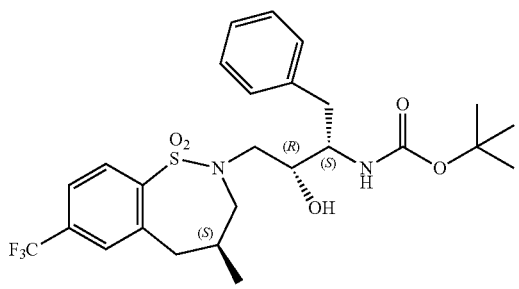

wherein the C3' carbon is of a S absolute configuration, the C2' carbon is of a R absolute configuration, and the C4 carbon is of a S absolute configuration.

49. The method according to claim 35, wherein the compound is

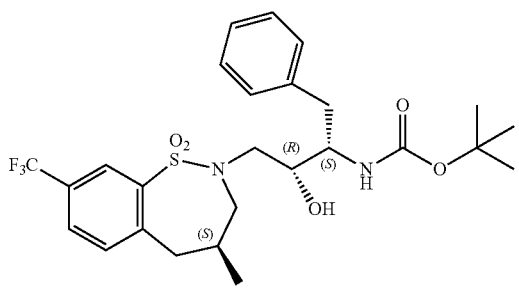

wherein the C3' carbon is of a S absolute configuration, the C2' carbon is of a R absolute configuration, and the C4 carbon is of a S absolute configuration.

50. The method according to claim 35, wherein the compound is

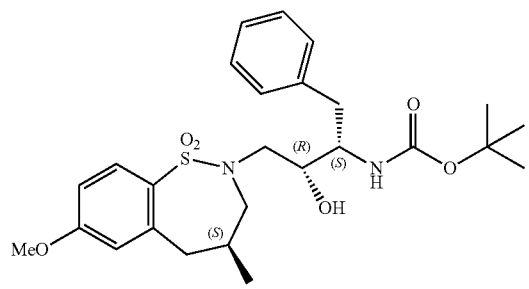

wherein the C3' carbon is of a S absolute configuration, the C2' carbon is of a R absolute configuration, and the C4 carbon is of a S absolute configuration.

51. The method according to claim 35, wherein the compound is

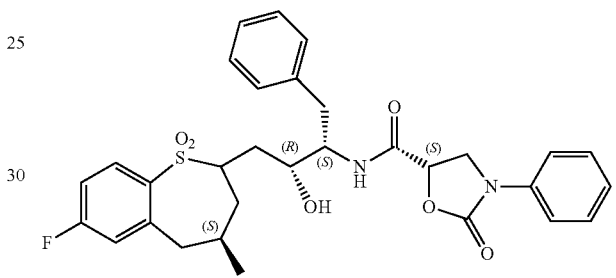

wherein the C3' carbon is of a S absolute configuration, the C2' carbon is of a R absolute configuration, the C4 carbon is of a S absolute configuration, and the C5' carbon is of a S absolute configuration.

52. The method according to claim 35, wherein the HIV protease is HIV-1 protease.

53. The method according to claim 35, wherein the HIV protease is HIV-2 protease.

54. The method according to claim 35, wherein the therapeutically effective amount is from about 0.000001 mg/kg body weight to about 10 g/kg body weight.

55. The method according to claim 35, wherein the composition further comprises a therapeutically effective amount of an additional therapeutic agent.

56. The method according to claim 55, wherein the additional therapeutic agent is selected from the group consisting of an antibiotic agent, an antifungal agent, an antiviral agent, an antiprotozoal agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, or a hormone.

57. The method according to claim 35, wherein the electron withdrawing group is a halogen.

58. The method according to claim 35, wherein the electron withdrawing group is nitrile.

59. The method according to claim 35, wherein the electron withdrawing group is a carboxylic acid.

60. The method according to claim 35, wherein the electron withdrawing group is a carbonyl, alkyl sulphone, aryl sulphone, sulphonamides, amides and N-substituted amides.

61. The method according to claim 35, wherein the electron withdrawing group is an aldehyde.

62. The method according to claim 35, wherein the electron withdrawing group is an acetaldehyde.

63. The method according to claim 35, wherein the electron withdrawing group is a nitro group.

64. The method according to claim 35, wherein the electron withdrawing group is selected from the group consisting of a trifluoromethyl, a difluoromethyl, a nitrile, a nitro, a sulphone, a sulphonamide, an amide and an N-substituted amide.

65. The method according to claim 35, wherein the electron donating group is an alkyl group.

66. The method according to claim 35, wherein the electron donating group is an alcohol group.

67. The method according to claim 35, wherein the electron donating group is selected from the group consisting of an alkoxy, a trifluoromethoxy, and a difluoromethoxy.

68. The method according to claim 35, wherein the electron donating group is selected from the group consisting of an amino group, an amide, a substituted amide, an urea, a substituted urea, a sulphonamide and a substituted sulphonamide.

* * * * *